US011930837B2

(12) United States Patent
Diaz-De-Durana et al.

(10) Patent No.: US 11,930,837 B2
(45) Date of Patent: Mar. 19, 2024

(54) ANTIBODY-CYTOKINE ENGRAFTED PROTEINS AND METHODS OF USE FOR IMMUNE RELATED DISORDERS

(71) Applicant: NOVARTIS AG, Basel (CH)

(72) Inventors: Yaiza Diaz-De-Durana, San Diego, CA (US); Michael DiDonato, San Diego, CA (US); Christophe Filippi, Studio City, CA (US); Shelly Meeusen, Rancho Santa Fe, CA (US); Glen Spraggon, San Diego, CA (US)

(73) Assignee: NOVARTIS AG, Basel (CH)

( * ) Notice: Subject to any disclaimer, the term of this patent is extended or adjusted under 35 U.S.C. 154(b) by 130 days.

(21) Appl. No.: 17/403,710

(22) Filed: Aug. 16, 2021

(65) Prior Publication Data

US 2022/0039441 A1 Feb. 10, 2022

Related U.S. Application Data

(62) Division of application No. 16/616,138, filed as application No. PCT/IB2018/053622 on May 22, 2018, now Pat. No. 11,122,825.

(60) Provisional application No. 62/510,514, filed on May 24, 2017.

(51) Int. Cl.
| | |
|---|---|
| A61K 38/20 | (2006.01) |
| A23L 7/10 | (2016.01) |
| A23L 7/104 | (2016.01) |
| B02B 1/04 | (2006.01) |
| B02C 4/06 | (2006.01) |
| B02C 4/16 | (2006.01) |
| B02C 9/00 | (2006.01) |
| B02C 23/18 | (2006.01) |
| B02C 23/40 | (2006.01) |
| C07K 16/46 | (2006.01) |
| B02C 15/14 | (2006.01) |

(52) U.S. Cl.
CPC ............. *A23L 7/197* (2016.08); *A23L 7/104* (2016.08); *A61K 38/2013* (2013.01); *B02B 1/04* (2013.01); *B02C 4/06* (2013.01); *B02C 4/16* (2013.01); *B02C 9/00* (2013.01); *B02C 23/18* (2013.01); *B02C 23/40* (2013.01); *C07K 16/46* (2013.01); *A23V 2002/00* (2013.01); *B02C 15/14* (2013.01)

(58) Field of Classification Search
CPC .................................................. A61K 38/2013
See application file for complete search history.

(56) References Cited

U.S. PATENT DOCUMENTS 7,279,462 B1 10/2007 Zanetti

FOREIGN PATENT DOCUMENTS

| WO | 9618412 A1 | 6/1996 |
|---|---|---|
| WO | 9943713 A1 | 9/1999 |
| WO | 99/060128 A1 | 11/1999 |
| WO | 0244197 A2 | 6/2002 |
| WO | 0246238 A2 | 6/2002 |
| WO | 2002/060919 A2 | 8/2002 |
| WO | 2003048334 A2 | 6/2003 |
| WO | 03085086 A2 | 10/2003 |
| WO | 2004/050017 A2 | 6/2004 |
| WO | 2004050017 A2 | 6/2004 |
| WO | 2004108078 A2 | 12/2004 |
| WO | 2005060642 A2 | 7/2005 |
| WO | 2005087797 A1 | 9/2005 |
| WO | 2006/050166 A2 | 5/2006 |
| WO | 2006082052 A1 | 8/2006 |
| WO | 2007149875 A2 | 12/2007 |
| WO | 2009088805 A2 | 7/2009 |
| WO | 2010099019 A1 | 9/2010 |
| WO | 2011020783 A2 | 2/2011 |
| WO | 2012009705 A1 | 1/2012 |
| WO | 2012045334 A1 | 4/2012 |
| WO | 2012107416 A2 | 8/2012 |
| WO | 2012107417 A1 | 8/2012 |
| WO | 2012146628 A1 | 11/2012 |
| WO | 2013106485 A2 | 7/2013 |
| WO | 2013106489 A1 | 7/2013 |
| WO | 2014023673 A1 | 2/2014 |
| WO | 2014023679 A1 | 2/2014 |
| WO | 2014023752 A1 | 2/2014 |
| WO | 2014110368 A1 | 7/2014 |
| WO | 2014/153063 A1 | 9/2014 |
| WO | 2014138725 A1 | 9/2014 |
| WO | 2015006736 A2 | 1/2015 |
| WO | 2015006744 A1 | 1/2015 |
| WO | 2015010100 A2 | 1/2015 |
| WO | 2015017146 A2 | 2/2015 |
| WO | 2015/118016 A1 | 8/2015 |
| WO | 2016030350 A1 | 3/2016 |
| WO | 2017093947 A1 | 6/2017 |

(Continued)

OTHER PUBLICATIONS

Neri, et al., "Immunocytokines for cancer treatment: past, present and future", Current Opinion in Immunology, Apr. 6, 2016, vol. 40, pp. 96-102, Elsevier Ltd.

(Continued)

*Primary Examiner* — Prema M Mertz
(74) *Attorney, Agent, or Firm* — Erin M. Foley

(57) ABSTRACT

The present disclosure provides antibody cytokine engrafted proteins that bind to and stimulate intracellular signaling through a high affinity interleukin receptor. The antibody cytokine engrafted proteins find use in enhancing anti-inflammatory cell responses, and reducing pro-inflammatory effects in the treatment, amelioration and prevention of immune related disorders such as Type 1 Diabetes.

7 Claims, 22 Drawing Sheets

Specification includes a Sequence Listing.

(56) References Cited

FOREIGN PATENT DOCUMENTS

WO     2017127514 A1    7/2017

OTHER PUBLICATIONS

Liu, et al., "Functional human antibody CDR fusions as long-acting therapeutic endocrine agonists", Proceedings of the National Academy of Sciences, Jan. 20, 2015, vol. 112, No. 5, pp. 1356-1361.
Laurent, et al., "T-cell activation by treatment of cancer patients with EMD 521873 (Selectikine), an IL-2/anti-DNA fusion protein", Journal of Translational Medicine, Jan. 7, 2013, vol. 11, No. 1, pp. 1-12, Biomed Central.
Arenas-Ramirez, et al., "Interleukin-2: Biology, Design and Application", Trends in Immunology, Nov. 10, 2015, vol. 36, No. 12, pp. 763-777, Elsevier, Ltd.
Wang, et al., "Structure of the Quaternary Complex of Interleukin-2 with its α, β, and γc Receptors", Science, Nov. 18, 2005, vol. 319, No. 5751, pp. 1159-1163.
Kontermann et al., "Bispecific antibodies", Drug Discovery Today, Jul. 2015, Issue 7, No. 20, pp. 838-847, Fig.1.
Acchione et al., "Impact of linker and conjugation chemistry on antigen binding, Fc receptor binding and thermal stability of model antibody-drug conjugates", mAbs, Apr. 26, 2012, vol. 4, No. 3, pp. 362-372, DOI: 10.4161/mabs.19449.
Torres et al., "The immunoglobulin constant region contributes to affinity and specificity", Trends in Immunology, 2008, vol. 29, No. 2, pp. 91-97.
Tokuriki et al., "Stability effects of mutations and protein evolvability", Current Opinion Structural Biology, 2009, vol. 19, pp. 596-604.
Rudikoff et al., "Single amino acid substitution altering antigen-binding specificity", Proc. Natl. Acad. Sci. USA, Immunology, Mar. 1982, vol. 79, pp. 1979-1983.
Halin et al., "Synergistic therapeutic effects of a tumor targeting antibody fragment, fused to interleukin 12 and to tumor necrosis factor alpha", Cancer Research, Jun. 2003, vol. 63, issue 12, pp. 3202-3210.
Frankel et al., "Characterization of diphtheria fusion proteins targeted to the human interleukin-3 receptor", Protein Engineering, 2000, vol. 13, No. 8, pp. 575-581.
Arnau et al., "Current strategies for the use of affinity tags and tag removal for the purification of recombinant proteins", Protein Expression and Purification, Jul. 2006, vol. 48, Issue 1, pp. 1-13.
Chen et al., "Fusion protein linkers: property, design and functionality", Advanced Drug Delivery Reviews, Oct. 15, 2013, vol. 65, No. 10, pp. 1357-1369, doi: 10.1016/j.addr.2012.09.039.
Maeda et al., "Engineering of functional chimeric protein G-Vargula Luciferase", Analytical Biochemistry, Jul. 1, 1997, vol. 249, issue 2, pp. 147-152.
Berry et al., "Substitution of cysteine for selenocysteine in type I iodothyronine deiodinase reduces the catalytic efficiency of the protein but enhances its translation", Endocrinology, Oct. 1, 1992, vol. 131, issue 4, pp. 1848-1852.
Gasser et al., "Antibody production with yeasts and filamentous fungi: on the road to large scale?", Biotechnology Letters, Nov. 22, 2006, vol. 29, pp. 201-212.
Burns et al., "A high molecular weight-melanoma associated antigen-specific chimeric antigen receptor redirects lymphocytes to target human melanomas", Cancer Research, Apr. 15, 2010, vol. 70, No. 8, pp. 3027-3033.
Muller et al., "Spliceosomal peptide P140 for immunotherapy of systemic lupus erythematosus: results of an early phase II clinical trial", Arthritis & Rheumatism: American College of Rheumatology, Dec. 2008, vol. 58, No. 12, pp. 3873-3883, DOI 10.1002/art.24027.
Zhang et al., "Functional Antibody CDR3 Fusion Proteins with Enhanced Pharmacological Properties", Angewandte Chemie International Edition, Aug. 5, 2013, vol. 52, No. 32, pp. 8295-8298, Wiley-VCH Verlag Gmbh & Co. KGaA, Weinheim.
Zhang et al., "An Antibody CDR3-Erythropoietin Fusion Protein", ACS Chemical Biology, vol. 8, No. 10, Oct. 18, 2013, pp. 2117-2121.
Liu et al., "Rational Design of CXCR4 Specific Antibodies with Elongated CDRs", Journal of the American Chemical Society, Jul. 30, 2014, vol. 136, No. 30, pp. 10557-10560.
Wang et al., "Reshaping Antibody Diversity", Cell, Jun. 6, 2013, vol. 153, pp. 1379-1393.
Zhang et al., "Rational design of humanized dual-agonist antibodies", Journal of the American Chemical Society, 2015, vol. 137, pp. 38-41.

FIGURE 1

| Name | Yield (mg/L) | Aggreg. (%) | Tm | LAL (EU/mg) | Format | Treg (fold expan.) | NK (fold expan.) | CD8 Teff (fold expan.) | IL-2Rαβγ (EC50 vs. IL-2) | IL-2Rβγ (EC50 vs. IL-2) |
|---|---|---|---|---|---|---|---|---|---|---|
| rhIL-2 Proleukin | N/A | N/A | N/A | N/A | Non-grafted | 1.5 | 2.4 | 1.9 | 1 | 1 |
| IgG.IL2D49A.H1 | 4 | 0.1 | 70.4/72.9 | 1.11 | D20A in H1 | 1.2 | 1.3 | 1.2 | 40 | 4400 |
| GFTX3b-IL2-H1 | 9.6 | 1.8 | 68.6 | 0.95 | H1 | 1.5 | 0.8 | 2.1 | 1 | 0.3 |
| GFTX3b-IL2-H2 | 6.6 | 1.6 | 67.4 | 0.76 | H2 | 0.9 | 0.9 | 2.2 | 6 | 1 |
| GFTX3b-IL2-H3 | 6.8 | 2.3 | 67 | 0.96 | H3 | 1.1 | 1.2 | 1.3 | 250 | 3400 |
| GFTX3b-IL2-L1 | 3.4 | 1.9 | 63.7/76.5 | 1.04 | L1 | 0.9 | 0.5 | 2 | 1 | 0.5 |
| GFTX3b-IL2-L2 | - | - | - | - | L2 | - | - | - | - | - |
| GFTX3b-IL2-L3 | 3.6 | 3.6 | 69.3 | 0.98 | L3 | 1.5 | 0.7 | 4.1 | 4 | 4 |
| GFTX3b_LALA-IL2-nH1 | 7.7 | 3.2 | 64.9 | 0.64 | Nt-shifted in H1 | 1.6 | 1 | 3.3 | 0.3 | 2 |
| GFTX3b_LALA-IL2-cH1 | 8.9 | 1.6 | 63.4/67 | 0.15 | Ct-shifted in H1 | 1.7 | 1 | 2.2 | 1 | 70 |
| GFTX3b_LALA-IL2-nH2 | - | - | - | - | Nt-shifted in H2 | - | - | - | - | - |
| GFTX3b_LALA-IL2-cH2 | 4.2 | 1.1 | 67.8 | 0.69 | Ct-shifted in H2 | 1.4 | 0.6 | 3.1 | 0.1 | 3 |

FIGURE 2

Antibody cytokine fusion protein shows greater activity on Treg cells and increased half-life

| Construct | IL-2R stimulation (STAT5 phosphorylation in human primary cells) | | | PK (T1/2 extension) | PD (cellular expansion in mouse *in vivo*) | | |
|---|---|---|---|---|---|---|---|
| | Treg | Teff | NK | | Treg | Teff | NK |
| rhIL-2 (Proleukin®) | ++ | + | + | - | + | + | + |
| IgG.IL2D49A.H1 | ++ | - | - | + | +++ | - | - |
| GFTX3b_IL2-L3 | + | + | - | + | ++ | +/- | - |

FIGURE 3

Antibody cytokine fusion protein shows greater activity on Treg cells

*Dose of 7mg/kg antibody cytokine fusion protein vs equimolar dose of 0.6 mg/kg IL2

| Construct | Dose* | Fold $T_{reg}$ | Fold NK | Fold $CD8_{eff}$ | Fold $CD4_{eff}$ | $T_{reg}$ : NK | $T_{reg}$ : $CD8_{eff}$ | $T_{reg}$ : $CD4_{eff}$ |
|---|---|---|---|---|---|---|---|---|
| IgG.IL2D49A.H1 | 7 mg/kg | 5.9 | 0.7 | 0.7 | 2.1 | 9.4 | 11.7 | 2.9 |
| GFTX3b_IL2-H1-D113A | 7 mg/kg | 1.7 | 0.7 | 2.9 | 1.3 | 2.0 | 1.0 | 1.3 |
| GFTX3b_IL2-L3 | 7 mg/kg | 1.7 | 0.7 | 3.2 | 0.9 | 0.7 | 0.6 | 2.0 |
| GFTX3b_IL2-H2 | 7 mg/kg | 1.3 | 0.8 | 1.2 | 1.0 | 1.6 | 1.4 | 1.3 |
| GFTX3b_IL2-H1 | 7 mg/kg | 1.2 | 0.9 | 1.6 | 1.2 | 1.6 | 1.2 | 1.1 |
| IL-2 (Proleukin) | 0.6 mg/kg | 1.0 | 0.7 | 0.6 | 0.9 | 1.6 | 1.6 | 1.1 |
| IL-2 (Proleukin) | 3 mg/kg | 1.4 | 1.4 | 2.8 | 2.2 | 1.0 | 0.5 | 1.0 |

IL-2R signaling potency is reduced in CD4 Tcon and CD8 Teff but not in Tregs in vitro

IgG.IL2D49A.H1 expands functional and stable Tregs in vitro

Potency on IL-2R signaling reduced in human NKs in vitro with IgG.IL2D49A.H1

Evaluation of the pharmacokinetic (PK), pharmacodynamics (PD), and toxicological effects of IgG.IL2D49A.H1 when administered subcutaneously to female Cyno monkeys.

Antibody cytokine engrafted protein shows a half-life of 12-14 hours compared to an IL2 half-life of 4 hours

Human T<sub>regs</sub> expand but not T<sub>eff</sub> or NKs in mice with xeno-GvHD

IgG.IL2D49A.H1 ameliorates body weight loss in mice with xeno-GvHD

IgG.IL2D49A.H1 prevents Type 1 Diabetes development in NOD mice

IgG.IL2D49A.H1 versus low dose Proleukin in pre-diabetic NOD mice

Pharmacokinetics of efficacious dose of IgG.IL2D49A.H1 in the NOD mouse model

Pharmacokinetics of efficacious dose of IgG.IL2D49A.H1 in the NOD mouse model

FIGURE 14

Dose range finding in pre-diabetic NOD mice

| Dose | IgG.IL2D49A H1 (spleen, blood) | | Proleukin (spleen, blood) | | Tolerability (deaths) |
|---|---|---|---|---|---|
| | Treg/CD4 Tcon | Treg/CD8Teff | Treg/CD4 Tcon | Treg/CD8Teff | |
| 0.01 | 3, 2 | 2 | 1, 0.4 | 1 | |
| 0.03 | 1.10.45 | 1.4 | 0.9, 0.45 | 1.2 | |
| 0.1 | 1.25, 0.6 | 2 | 1, 0.5 | 1.1 | |
| 0.3 | 6 | 6 | 2 | 1 | |
| 1 | 3, 3 | 3.5 | 1.5, 0.6 | 1.5 | |
| 3 | 10, 5 | 6 | 2, 1 | 2 | Proleukin |
| 9 | 10, 5 | 6 | 2, 1 | 2 | Proleukin, all |

IgG.IL2D49A.H1 and Proleukin® signaling profiles in vitiligo patient PBMCs

IgG.IL2D49A.H1 and Proleukin® signaling profiles in T1D patient PBMCs

FIGURE 16

IL2 antibody cytokine engrafted proteins have binding to RSV

Treg expansion in cynomolgus monkey after a single dose of IgG.IL2D49A.H1

FIGURE 18

Increasing concentrations of a crosslinker anti-human IgG antibody does not interfere with the selective activities of GFTX3b_IL- Selective signaling preserved in different autoimmune patients PBMC with GFTX3b_IL-2-H1-D49A
pSTAT5 in vitro signaling assay

FIGURE 20

GFTX3b_IL-2-H1-D49A has higher selectivity than Proleukin for signaling in Tregs over T effector cells in human PBMC pSTAT5 in vitro signaling assay

| GFTX3b_IL-2-H1-D49A specificity over Proleukin for signaling in Tregs over T effectors | |
|---|---|
| T regulatory cells vs CD4 T effectors | 5,000-fold |
| T regulatory cells vs CD8 T effectors | 500-fold |
| T regulatory cells vs CD8 Teff/mem | 500-fold |

ANTIBODY-CYTOKINE ENGRAFTED PROTEINS AND METHODS OF USE FOR IMMUNE RELATED DISORDERS

CROSS-REFERENCE TO RELATED APPLICATIONS

This application is a divisional of U.S. application Ser. No. 16/616,138 filed 22 Nov. 2019; which is a U.S. 371 national stage entry of International Application Number PCT/IB2018/053622, filed 22 May 2018; which claims the benefit of priority to U.S. Provisional Patent Application No. 62/510,514, filed 24 May 2017, the content of which is hereby incorporated by reference in its entirety.

FIELD

The present disclosure relates to antibody-cytokine engrafted proteins that bind to interleukin-2 (IL2) high affinity receptor, and methods of treating autoimmune and immune related disorders.

SEQUENCE LISTING

The instant application contains a Sequence Listing which has been submitted electronically in ASCII format and is hereby incorporated by reference in its entirety. Said ASCII copy, created on Mar. 30, 2018, is named PAT056491-WO-PCT_SL.txt and is 115,255 bytes in size.

BACKGROUND

IL2 was first cloned in 1983 (Taniguchi et al., Nature 1983, 302:305-310, Devos et al., Nucleic Acid Res. 1983, 11(13):4307-4323, Maeda et al., Biochem. Biophys. Res. Comm. 1983, 115:1040-1047). The IL2 protein has a length of 153 amino acids with a signal peptide from amino acids 1-20 and folds into a structure of 4 anti-parallel, amphipathic alpha-helices (Smith K.A., Science 1988, 240:1169-1176).

IL2 mediates its biological effect by signalling through a high affinity or low affinity receptor (Kreig et al., PNAS 2010, 107(26)11906-11911). The high affinity receptor is trimeric, consisting of IL2-Rα (CD25) IL2-Rβ (CD122) and IL2-Rγ (CD132). The low affinity receptor is dimeric, consisting only of the IL2-Rβ(CD122) and IL2-Rγ(CD132) chains. The low affinity receptor binds IL2, but with 10-100 times less affinity than the trimeric, high affinity receptor, indicating that IL2-Rα (CD25) is important for the increase in affinity, but is not a signalling component (Kreig et al., supra). The expression of the IL2 receptors is also distinct. The high affinity IL2 receptor is expressed on activated T cells and CD4+/Foxp3+ T regulatory cells (Treg). In contrast, the low affinity IL2 receptor is found on CD8+ T memory cells, T convention cells (Tcon) and natural killer cells (NK).

Recombinant IL2 (rhIL2) was initially approved for clinical use in 1992 (Coventry et al., Cancer Mgt Res. 2012 4:215-221). Proleukin® (Aldesleukin) is a modified IL2 that is aglycosylated, lacks an N-terminal alanine and has a serine substituted for cysteine at amino acid 125 (C125S). Proleukin® was initially indicated as a therapy for malignant melanoma and renal cell carcinoma, but has been used for other cancer types such as colorectal, breast, lung and mesothelioma (Coventry et al., supra). A study spanning 259 renal cell carcinoma patients from 1986 to 2006, found that 23 patients has a complete response and 30 had a partial response (Klapper et al., Cancer 2008 113(2):293-301). This accounted for an overall objective response rate of 20%, with complete tumor regression in 7% of the patients with renal cell cancer (Klapper et al., supra).

However, IL2 treatment of cancer was not without adverse effects. The 259 patient study noted capillary/vascular leakage, vasodilation and oliguria. There were also Grade 3 and Grade 4 infections, both of catheters and general infection, attributed to neutrophil dysfunction (Klapper et al., supra). Proleukin® literature notes that Proleukin® has been associated with exacerbation of autoimmune diseases and immune related disorders such as Crohn's Disease, scleroderma, thyroiditis, inflammatory arthritis, diabetes mellitus, oculo-bulbar myasthenia gravis, crescentic IgA glomerulonephritis, cholecystitis, cerebral vasculitis, Stevens-Johnson syndrome and bullous pemphigoid.

The discovery that Treg cells constitutively expressed the high affinity IL2 receptor and were dependent on IL2 for survival and function lead to work focusing on IL2 as a way to simulate Treg cells (D'Cruz et al., Nat. Immuno. 2005, 6:1152-1159). Low dose IL2 was shown to be a safe and effective treatment for patients with Type I diabetes (Hartemann et al., Lancet Diabetes Endocrinol. 2013, 1:295-305). Hepatitis C Virus induced vasculitis (Saadoun et al., N. Eng. J. Med. 2011, 365:2067-2077) and chronic Graft versus Host Disease (Koreth et al., N. Eng. J. Med. 2011 365:2055-2066). However, IL2 has a very short half life in the body, requiring multiple administrations. This illustrates the need for IL2 therapeutics with selectivity for stimulating Tregs via the high affinity receptor with reduced activity on the IL2 low receptor and improved pharmacokinetics.

DESCRIPTION

The present disclosure provides for antibody cytokine engrafted proteins having an IL2 molecule engrafted into the CDR sequences of an antibody having preferred therapeutic profiles over molecules known and used in the clinic. In particular, the provided antibody cytokine engrafted proteins increase or maintain Tregs activity without increasing the activity of CD8+ T cells, Tcons or NK cells. Additionally, provided compositions convey improved half-life, stability and produceability over recombinant human IL2 formulations such as Proleukin®. The preferred properties of these compositions result in preferable therapeutic compositions over those previously used in the clinic or described in the literature. For example, some embodiments disclosed herein provide antibody cytokine engrafted proteins that preferably bind to and promote signaling through the IL2 high affinity receptor versus the IL2 low affinity receptor. Some embodiments disclosed herein provide antibody cytokine engrafted proteins that preferably activate Tregs versus CD8+ T cells, Tcons or NK cells.

Embodiments of the present disclosure provide antibody-cytokine engrafted proteins comprising:
(a) a heavy chain variable region (VH), comprising Complementarity Determining Regions (CDR) HCDR1, HCDR2, HCDR3; and
(b) a light chain variable region (VL), comprising LCDR1, LCDR2, LCDR3; and
(c) an Interleukin 2 (IL2) molecule engrafted into a CDR of the VH or the VL.

The antibody cytokine engrafted protein, comprising an IL2 molecule engrafted into a heavy chain CDR.

The antibody cytokine engrafted protein, wherein the IL2 molecule is engrafted into a region selected from complementarity determining region 1 (HCDR1), complementarity determining region 2 (HCDR2) or complementarity determining region 3 (HCDR3).

The antibody cytokine engrafted protein, comprising an IL2 molecule engrafted into a HCDR1.

The antibody cytokine engrafted protein, comprising an IL2 molecule engrafted into a light chain CDR.

The antibody cytokine engrafted protein, wherein the IL2 molecule is engrafted into a region selected from complementarity determining region 1 (LCDR1), complementarity determining region 2 (LCDR2), and complementarity determining region 3 (LCDR3).

The antibody cytokine engrafted protein, comprising an IL2 molecule containing a mutation that reduces the affinity of the IL2 molecule to the low affinity IL2 receptor.

The antibody cytokine engrafted protein, where the antibody cytokine engrafted protein stimulates Treg cell proliferation greater than native IL2 or Proleukin®.

The antibody cytokine engrafted protein, where the antibody cytokine engrafted protein stimulates CD8 T effector proliferation less than native IL2 or Proleukin®.

The antibody cytokine engrafted protein, where the antibody cytokine engrafted protein has a longer half life than native IL2 or Proleukin®.

The antibody cytokine engrafted protein, wherein the IL2 molecule consists of SEQ ID NO:4.

The antibody cytokine engrafted protein, wherein the IL2 molecule consists of SEQ ID NO:6.

The antibody cytokine engrafted protein, comprising an IgG class antibody heavy chain.

The antibody cytokine engrafted protein, wherein the IgG class antibody heavy chain is selected from IgG1, IgG2, or IgG4.

The antibody cytokine engrafted protein, wherein the binding specificity of the antibody CDRs is reduced by the engrafted IL2 molecule.

The antibody cytokine engrafted protein, wherein the binding specificity of the antibody CDRs is retained in the presence of the engrafted IL2 molecule.

The antibody cytokine engrafted protein, wherein the binding specificity of the antibody CDRs is distinct from the binding specificity of the IL2 molecule.

The antibody cytokine engrafted protein, wherein the binding specificity of the antibody variable domain is to a non-human antigen.

The antibody cytokine engrafted protein, wherein the non-human antigen is a virus.

The antibody cytokine engrafted protein, wherein the virus is respiratory syncytial virus (RSV).

The antibody cytokine engrafted protein, wherein the RSV is selected from RSV subgroup A and RSV subgroup B.

The antibody cytokine engrafted protein, wherein the antibody scaffold portion of the antibody cytokine engrafted protein is humanized or human.

Embodiments of the present disclosure provide antibody cytokine engrafted proteins comprising:
(i) a heavy chain variable region that comprises (a) a HCDR1 of SEQ ID NO: 17, (b) a HCDR2 of SEQ ID NO:18, (c) a HCDR3 of SEQ ID NO:19 and a light chain variable region that comprises: (d) a LCDR1 of SEQ ID NO:30, (e) a LCDR2 of SEQ ID NO:31, and (f) a LCDR3 of SEQ ID NO:32;
(ii) a heavy chain variable region that comprises (a) a HCDR1 of SEQ ID NO:43, (b) a HCDR2 of SEQ ID NO:44, (c) a HCDR3 of SEQ ID NO:45; and a light chain variable region that comprises: (d) a LCDR1 of SEQ ID NO:56, (e) a LCDR2 of SEQ ID NO:57, and (f) a LCDR3 of SEQ ID NO:58;
(iii) a heavy chain variable region that comprises (a) a HCDR1 of SEQ ID NO:69, (b) a HCDR2 of SEQ ID NO:70, (c) a HCDR3 of SEQ ID NO:71; and a light chain variable region that comprises: (d) a LCDR1 of SEQ ID NO:82, (e) a LCDR2 of SEQ ID NO:83, and (f) a LCDR3 of SEQ ID NO:84; or
(iv) a heavy chain variable region that comprises (a) a HCDR1 of SEQ ID NO:95, (b) a HCDR2 of SEQ ID NO:96, (c) a HCDR3 of SEQ ID NO:97; and a light chain variable region that comprises: (d) a LCDR1 of SEQ ID NO:108, (e) a LCDR2 of SEQ ID NO:109, and (f) a LCDR3 of SEQ ID NO:110.

Embodiments of the present disclosure provide antibody cytokine engrafted proteins comprising:
(i) a heavy chain variable region (VH) that comprises SEQ ID NO:20, and a light chain variable region (VL) that comprises SEQ ID NO: 33;
(ii) a heavy chain variable region (VH) that comprises SEQ ID NO: 46, and a light chain variable region (VL) that comprises SEQ ID NO: 59;
(iii) a heavy chain variable region (VH) that comprises SEQ ID NO:72, and a light chain variable region (VL) that comprises SEQ ID NO:85; or
(iv) a heavy chain variable region (VH) that comprises SEQ ID NO:98, and a light chain variable region (VL) that comprises SEQ ID NO:111.

The antibody cytokine engrafted protein, wherein the antibody comprises a modified Fc region corresponding with reduced effector function.

The antibody cytokine engrafted protein, wherein the modified Fc region comprises a mutation selected from one or more of D265A, P329A, P329G, N297A, L234A, and L235A.

The antibody cytokine engrafted protein, wherein the modified Fc region comprises a combination of mutations selected from one or more of D265A/P329A, D265A/N297A, L234/L235A, P329A/L234A/L235A, and P329G/L234A/L235A.

Embodiments of the present disclosure provide antibody cytokine engrafted proteins comprising a HCDR1 of SEQ ID NO: 17, a HCDR2 of SEQ ID NO:18, a HCDR3 of SEQ ID NO:19, a LCDR1 of SEQ ID NO:30, a LCDR2 of SEQ ID NO:31, a LCDR3 of SEQ ID NO:32, a modified Fc region containing the mutation D265A/P329A, wherein the antibody cytokine engrafted protein has greater activation of Treg cells when compared to Proleukin®.

Embodiments of the present disclosure provide antibody cytokine engrafted proteins comprising a HCDR1 of SEQ ID NO:43, a HCDR2 of SEQ ID NO:44, a HCDR3 of SEQ ID NO:45, a LCDR1 of SEQ ID NO:56, a LCDR2 of SEQ ID NO:57, a LCDR3 of SEQ ID NO:58, a modified Fc region containing the mutation D265A/P329A, wherein the antibody cytokine engrafted protein has greater activation of Treg cells when compared to Proleukin®.

Embodiments of the present disclosure provide antibody cytokine engrafted proteins comprising a HCDR1 of SEQ ID NO:69, a HCDR2 of SEQ ID NO:70, a HCDR3 of SEQ ID NO:71, a LCDR1 of SEQ ID NO:82, a LCDR2 of SEQ ID NO:83, a LCDR3 of SEQ ID NO:84, a modified Fc region containing the mutation D265A/P329A, wherein the antibody cytokine engrafted protein has greater activation of Treg cells when compared to Proleukin®.

Embodiments of the present disclosure provide antibody cytokine engrafted proteins comprising a HCDR1 of SEQ ID NO:95, a HCDR2 of SEQ ID NO:96, a HCDR3 of SEQ ID NO:97, a LCDR1 of SEQ ID NO:108, a LCDR2 of SEQ ID NO:109, a LCDR3 of SEQ ID NO:110, a modified Fc region containing the mutation D265A/P329A, wherein the antibody cytokine engrafted protein has greater activation of Treg cells when compared to Proleukin®.

Embodiments of the present disclosure provide isolated nucleic acids encoding an antibody cytokine engrafted protein comprising:
(i) a heavy chain of SEQ ID NO:23 and a light chain of SEQ ID NO:36;
(ii) a heavy chain of SEQ ID NO:49 and a light chain of SEQ ID NO:62;
(iii) a heavy chain of SEQ ID NO:75 and a light chain of SEQ ID NO:88; or
(iv) a heavy chain of SEQ ID NO:101 and a light chain of SEQ ID NO:114.

Embodiments of the present disclosure provide recombinant host cells suitable for the production of an antibody cytokine engrafted protein, comprising the nucleic acids disclosed herein encoding the heavy and light chain polypeptides of the protein, and optionally, a secretion signal.

The recombinant host cell which is a mammalian cell line.

Embodiments of the present disclosure provide pharmaceutical compositions comprising the antibody cytokine engrafted protein and one or more pharmaceutically acceptable carrier.

Embodiments of the present disclosure provide methods of treating an immune related disorder in an individual in need thereof, comprising administering to the individual a therapeutically effective amount of the antibody cytokine engrafted proteins or pharmaceutical compositions disclosed herein.

The method wherein said immune related disorder is selected from the group consisting of: Type 1 diabetes, System Lupus Erythematosus, Vitiligo, chronic graft versus host disease (cGvHD), prophylactic acute graft versus host disease (pGvHD), HIV-induced vasculitis, Alopecia areata, Systemic sclerosis morphoea, and primary anti-phospholipid syndrome.

The method wherein the antibody cytokine engrafted protein or pharmaceutical composition is administered in combination with another therapeutic agent.

The method wherein the therapeutic agent is another antibody cytokine engrafted protein.

Embodiments of the present disclosure provide methods of expanding Treg cells in a patient in need thereof, comprising administering an antibody cytokine engrafted protein or pharmaceutical composition to the patient.

The method wherein the Treg cells are expanded and CD8 T effector cells are not expanded.

The method wherein the Treg cells are expanded and NK cells are not expanded.

The method wherein the antibody cytokine engrafted protein or pharmaceutical composition is administered in combination with another therapeutic agent.

The method wherein the therapeutic agent is another antibody cytokine engrafted protein.

Embodiments of the present disclosure provide antibody cytokine engrafted proteins for use as a therapeutic agent.

The use wherein the antibody cytokine engrafted protein comprises: (i) a heavy chain variable region that comprises (a) a HCDR1 of SEQ ID NO: 17, (b) a HCDR2 of SEQ ID NO:18, (c) a HCDR3 of SEQ ID NO:19 and a light chain variable region that comprises: (d) a LCDR1 of SEQ ID NO:30, (e) a LCDR2 of SEQ ID NO:31, and (f) a LCDR3 of SEQ ID NO:32; and (ii) a heavy chain variable region that comprises (a) a HCDR1 of SEQ ID NO:43, (b) a HCDR2 of SEQ ID NO:44, (c) a HCDR3 of SEQ ID NO:45; and a light chain variable region that comprises: (d) a LCDR1 of SEQ ID NO:56, (e) a LCDR2 of SEQ ID NO:57, and (f) a LCDR3 of SEQ ID NO:58, in the treatment of immune related disorders.

The use wherein the immune related disorder is selected from the group consisting of Type 1 diabetes, System Lupus Erythematosus, Vitiligo, chronic graft versus host disease (cGvHD), prophylactic acute graft versus host disease (pGvHD), HIV-induced vasculitis, Alopecia areata, Systemic sclerosis morphoea, and primary anti-phospholipid syndrome.

The use wherein the antibody cytokine engrafted protein is administered in combination with another therapeutic agent.

Embodiments of the present disclosure provide uses of an antibody cytokine engrafted protein disclosed herein for the manufacture of a medicament for the treatment of immune related disorder in an individual in need thereof.

The use wherein the immune related disorder is selected from the group consisting of: Type 1 diabetes, System Lupus Erythematosus, Vitiligo, chronic graft versus host disease (cGvHD), prophylactic acute graft versus host disease (pGvHD), HIV-induced vasculitis, Alopecia areata, Systemic sclerosis morphoea, and primary anti-phospholipid syndrome.

In certain embodiments, the antibody cytokine engrafted protein comprises an IgG class antibody Fc region. In particular embodiments, the immunoglobulin is selected from IgG1, IgG2, or IgG4 subclass Fc region. The antibody, antibody fragment, or antigen binding molecule optionally contains at least one modification that modulates (i.e., increases or decreases) binding of the antibody or antibody fragment to an Fc receptor. The immunoglobulin heavy chain may optionally comprise a modification conferring modified effector function. In particular embodiments the immunoglobulin heavy chain may comprise a mutation conferring reduced effector function selected from any of D265A, P329A, P329G, N297A, D265A/P329A, D265A/N297A, L234/L235A, P329A/L234A/L235A, and P329G/L234A/L235A.

The antibody cytokine engrafted protein also comprises variations in the IL2 portion of the molecule. The variations can be single amino acid changes, single amino acid deletions, multiple amino acid changes and multiple amino acid deletions. These changes in the IL2 cytokine portion of the molecule can decrease the affinity of the cytokine engrafted protein for the low-affinity IL2 receptor.

Furthermore, the disclosure provides polynucleotides encoding at least a heavy chain and/or a light chain protein of an antibody cytokine engrafted protein as described herein. In another related aspect, the disclosure further provides host cells suitable for the production of an antibody cytokine engrafted protein as described herein. In particular embodiments, host cells comprise nucleic acids encoding a light chain and/or heavy chain polypeptide of the antibody cytokine engrafted protein. In still another aspect, methods for producing antibody cytokine engrafted proteins are provided, comprising culturing provided host cells as described herein under conditions suitable for expression, formation, and secretion of the antibody cytokine engrafted protein and recovering the antibody cytokine engrafted protein from the culture. In a further aspect, the disclosure further provides kits comprising an antibody cytokine engrafted protein, as described herein.

In another related aspect, the disclosure further provides compositions comprising an antibody cytokine engrafted protein, as described herein, and a pharmaceutically acceptable carrier. In some embodiments, the disclosure provides pharmaceutical compositions comprising an antibody cytokine engrafted protein for administering to an individual.

In another aspect, the disclosure provides methods of treating an immune related disorder in an individual in need thereof, comprising administering to the individual a therapeutically effective amount of an antibody cytokine engrafted protein, as described herein. In a further aspect, the disclosure provides an antibody cytokine engrafted protein for use in treatment or prophylaxis of an immune related disorder in an individual.

In some embodiments, the patient has an immune related disorder, for example, Type 1 diabetes, System Lupus Erythematosus, Vitiligo, chronic graft versus host disease (cGvHD), prophylactic acute graft versus host disease (pGvHD), HIV-induced vasculitis, Alopecia areata, Systemic sclerosis morphoea and primary anti-phospholipid syndrome. For some indications, the antibody cytokine engrafted protein is co-administered with a steroid (e.g., methylprednisolone, hydrocortisone, prednisone, prednisolone, budesonide, dexamethasone).

DEFINITIONS

An "antibody" refers to a molecule of the immunoglobulin family comprising a tetrameric structural unit. Each tetramer is composed of two identical pairs of polypeptide chains, each pair having one "light" chain (about 25 kD) and one "heavy" chain (about 50-70 kD), connected through a disulfide bond. Recognized immunoglobulin genes include the $\lambda$, $\alpha$, $\gamma$, $\delta$, $\varepsilon$, and $\mu$ constant region genes, as well as the myriad immunoglobulin variable region genes. Light chains are classified as either $\kappa$ or $\lambda$. Heavy chains are classified as $\gamma$, $\mu$, $\alpha$, $\delta$, or $\varepsilon$, which in turn define the immunoglobulin classes, IgG, IgM, IgA, IgD, and IgE, respectively. Antibodies can be of any isotype/class (e.g., IgG, IgM, IgA, IgD, and IgE), or any subclass (e.g., IgG1, IgG2, IgG3, IgG4, IgA1, IgA2).

Both the light and heavy chains are divided into regions of structural and functional homology. The terms "constant" and "variable" are used structurally and functionally. The N-terminus of each chain defines a variable (V) region or domain of about 100 to 110 or more amino acids primarily responsible for antigen recognition. The terms variable light chain ($V_L$) and variable heavy chain ($V_H$) refer to these regions of light and heavy chains respectively. The pairing of a VH and VL together forms a single antigen-binding site. In addition to V regions, both heavy chains and light chains contain a constant (C) region or domain. A secreted form of a immunoglobulin C region is made up of three C domains, CH1, CH2, CH3, optionally CH4 (C$\mu$), and a hinge region. A membrane-bound form of an immunoglobulin C region also has membrane and intracellular domains. Each light chain has a VL at the N-terminus followed by a constant domain (C) at its other end. The constant domains of the light chain (CL) and the heavy chain (CH1, CH2 or CH3) confer important biological properties such as secretion, transplacental mobility, Fc receptor binding, complement binding, and the like. By convention, the numbering of the constant region domains increases as they become more distal from the antigen binding site or amino-terminus of the antibody. The N-terminus is a variable region and at the C-terminus is a constant region; the CH3 and CL domains actually comprise the carboxy-terminal domains of the heavy and light chain, respectively. The VL is aligned with the VH and the CL is aligned with the first constant domain of the heavy chain. As used herein, an "antibody" encompasses conventional antibody structures and variations of antibodies. Thus, within the scope of this concept are antibody cytokine engrafted proteins, full length antibodies, chimeric antibodies, humanized antibodies, human antibodies, and antibody fragments thereof.

Antibodies exist as intact immunoglobulin chains or as a number of well-characterized antibody fragments produced by digestion with various peptidases. The term "antibody fragment," as used herein, refers to one or more portions of an antibody that retains six CDRs. Thus, for example, pepsin digests an antibody below the disulfide linkages in the hinge region to produce F(ab)'$_2$, a dimer of Fab' which itself is a light chain joined to $V_H$-$C_H$1 by a disulfide bond. The F(ab)'$_2$ may be reduced under mild conditions to break the disulfide linkage in the hinge region, thereby converting the F(ab)'2 dimer into an Fab' monomer. The Fab' monomer is essentially a Fab with a portion of the hinge region (Paul et al., *Fundamental Immunology* 3d ed. (1993)). While various antibody fragments are defined in terms of the digestion of an intact antibody, one of skill will appreciate that such fragments may be synthesized de novo either chemically or by using recombinant DNA methodology. As used herein, an "antibody fragment" refers to one or more portions of an antibody, either produced by the modification of whole antibodies, or those synthesized de novo using recombinant DNA methodologies, that retain binding specificity and functional activity. Examples of antibody fragments include Fv fragments, single chain antibodies (ScFv), Fab, Fab', Fd (Vh and CH1 domains), dAb (Vh and an isolated CDR); and multimeric versions of these fragments (e.g., F(ab')2,) with the same binding specificity. Antibody cytokine engrafted proteins can also comprise antibody fragments necessary to achieve the desired binding specificity and activity.

A "Fab" domain as used in the context comprises a heavy chain variable domain, a constant region CH1 domain, a light chain variable domain, and a light chain constant region CL domain. The interaction of the domains is stabilized by a disulfide bond between the CH1 and CL domains. In some embodiments, the heavy chain domains of the Fab are in the order, from N-terminus to C-terminus, VH-CH and the light chain domains of a Fab are in the order, from N-terminus to C-terminus, VL-CL. In some embodiments, the heavy chain domains of the Fab are in the order, from N-terminus to C-terminus, CH-VH and the light chain domains of the Fab are in the order CL-VL. Although the Fab fragment was historically identified by papain digestion of an intact immunoglobulin, a "Fab" is typically produced recombinantly by any method. Each Fab fragment is monovalent with respect to antigen binding, i.e., it has a single antigen-binding site.

"Complementarity-determining domains" or "complementary-determining regions" ("CDRs") interchangeably refer to the hypervariable regions of $V_L$ and $V_H$. CDRs are the target protein-binding site of antibody chains that harbor specificity for such target protein. There are three CDRs (CDR1-3, numbered sequentially from the N-terminus) in each human $V_L$ or $V_H$, constituting about 15-20% of the variable domains. CDRs are structurally complementary to the epitope of the target protein and are thus directly responsible for the binding specificity. The remaining stretches of the $V_L$ or $V_H$, the so-called framework regions (FR), exhibit less variation in amino acid sequence (Kuby, Immunology, 4th ed., Chapter 4. W. H. Freeman & Co., New York, 2000).

Positions of CDRs and framework regions can be determined using various well known definitions in the art, e.g., Kabat, Chothia, and AbM (see, e.g., Kabat et al. 1991 Sequences of Proteins of Immunological Interest, Fifth Edition, U.S. Department of Health and Human Services, NIH Publication No. 91-3242, Johnson et al., Nucleic Acids Res., 29:205-206 (2001); Chothia and Lesk, J. Mol. Biol., 196:901-917 (1987); Chothia et al., Nature, 342:877-883 (1989); Chothia et al., J. Mol. Biol., 227:799-817 (1992); Al-Lazikani et al., J.Mol.Biol., 273:927-748 (1997)). Definitions of antigen combining sites are also described in the following: Ruiz et al., Nucleic Acids Res., 28:219-221 (2000); and Lefranc, M.P., Nucleic Acids Res., 29:207-209 (2001); (ImMunoGenTics (IMGT) numbering) Lefranc, M.-P., The Immunologist, 7, 132-136 (1999); Lefranc, M.-P. et al., Dev. Comp. Immunol., 27, 55-77 (2003); MacCallum et al., J. Mol. Biol., 262:732-745 (1996); and Martin et al., Proc. Natl. Acad. Sci. USA, 86:9268-9272 (1989); Martin et al., Methods Enzymol., 203:121-153 (1991); and Rees et al., In Sternberg M. J. E. (ed.), Protein Structure Prediction, Oxford University Press, Oxford, 141-172 (1996).

Under Kabat, CDR amino acid residues in the $V_H$ are numbered 31-35 (HCDR1), 50-65 (HCDR2), and 95-102 (HCDR3); and the CDR amino acid residues in the $V_L$ are numbered 24-34 (LCDR1), 50-56 (LCDR2), and 89-97 (LCDR3). Under Chothia, CDR amino acids in the $V_H$ are numbered 26-32 (HCDR1), 52-56 (HCDR2), and 95-102 (HCDR3); and the amino acid residues in $V_L$ are numbered 26-32 (LCDR1), 50-52 (LCDR2), and 91-96 (LCDR3). By combining the CDR definitions of both Kabat and Chothia, the CDRs consist of amino acid residues 26-35 (HCDR1), 50-65 (HCDR2), and 95-102 (HCDR3) in human VH and amino acid residues 24-34 (LCDR1), 50-56 (LCDR2), and 89-97 (LCDR3) in human VL.

An "antibody variable light chain" or an "antibody variable heavy chain" as used herein refers to a polypeptide comprising the $V_L$ or $V_H$, respectively. The endogenous $V_L$ is encoded by the gene segments V (variable) and J (junctional), and the endogenous $V_H$ by V, D (diversity), and J. Each of $V_L$ or $V_H$ includes the CDRs as well as the framework regions (FR). The term "variable region" or "V-region" interchangeably refer to a heavy or light chain comprising FR1-CDR1-FR2-CDR2-FR3-CDR3-FR4. A V-region can be naturally occurring, recombinant or synthetic. In this application, antibody light chains and/or antibody heavy chains can be collectively referred to as "antibody chains." As provided and further described herein, an "antibody variable light chain" or an "antibody variable heavy chain" and/or a "variable region" and/or an "antibody chain" optionally comprises a cytokine polypeptide sequence incorporated into a CDR.

The C-terminal portion of an immunoglobulin heavy chain herein, comprising, e.g., CH2 and CH3 domains, is the "Fc" domain. An "Fc region" as used herein refers to the constant region of an antibody excluding the first constant region (CH1) immunoglobulin domain. Fc refers to the last two constant region immunoglobulin domains of IgA, IgD, and IgG, and the last three constant region immunoglobulin domains of IgE and IgM, and the flexible hinge N-terminal to these domains. For IgA and IgM Fc may include the J chain. For IgG, Fc comprises immunoglobulin domains Cγ2 and Cγ3 and the hinge between Cγ1 and Cγ. It is understood in the art that boundaries of the Fc region may vary, however, the human IgG heavy chain Fc region is usually defined to comprise residues C226 or P230 to its carboxyl-terminus, using the numbering is according to the EU index as in Kabat et al. (1991, NIH Publication 91-3242, National Technical Information Service, Springfield, Va.). "Fc region" may refer to this region in isolation or this region in the context of an antibody or antibody fragment. "Fc region" includes naturally occurring allelic variants of the Fc region, e.g., in the CH2 and CH3 region, including, e.g., modifications that modulate effector function. Fc regions also include variants that don't result in alterations to biological function. For example, one or more amino acids are deleted from the N-terminus or C-terminus of the Fc region of an immunoglobulin without substantial loss of biological function. For example, in certain embodiments a C-terminal lysine is modified replaced or removed. In particular embodiments one or more C-terminal residues in the Fc region is altered or removed. In certain embodiments one or more C-terminal residues in the Fc (e.g., a terminal lysine) is deleted. In certain other embodiments one or more C-terminal residues in the Fc is substituted with an alternate amino acid (e.g., a terminal lysine is replaced). Such variants are selected according to general rules known in the art so as to have minimal effect on activity (see, e.g., Bowie, et al., Science 247:306-1310, 1990). The Fc domain is the portion of the immunoglobulin (Ig) recognized by cell receptors, such as the FcR, and to which the complement-activating protein, C1 q, binds. The lower hinge region, which is encoded in the 5' portion of the CH2 exon, provides flexibility within the antibody for binding to FcR receptors.

A "chimeric antibody" is an antibody molecule in which (a) the constant region, or a portion thereof, is altered, replaced or exchanged so that the antigen binding site (variable region) is linked to a constant region of a different or altered class, effector function and/or species, or an entirely different molecule which confers new properties to the chimeric antibody, e.g., an enzyme, toxin, hormone, growth factor, and drug; or (b) the variable region, or a portion thereof, is altered, replaced or exchanged with a variable region having a different or altered antigen specificity.

A "humanized" antibody is an antibody that retains the reactivity (e.g., binding specificity, activity) of a non-human antibody while being less immunogenic in humans. This can be achieved, for instance, by retaining non-human CDR regions and replacing remaining parts of an antibody with human counterparts. See, e.g., Morrison et al., Proc. Natl. Acad. Sci. USA, 81:6851-6855 (1984); Morrison and Oi, Adv. Immunol., 44:65-92 (1988); Verhoeyen et al., Science, 239:1534-1536 (1988); Padlan, Molec. Immun., 28:489-498 (1991); Padlan, Molec. Immun., 31(3):169-217 (1994).

A "human antibody" includes antibodies having variable regions in which both the framework and CDR regions are derived from sequences of human origin. Furthermore, if an antibody contains a constant region, the constant region also is derived from such human sequences, e.g., human germline sequences, or mutated versions of human germline sequences or antibody containing consensus framework sequences derived from human framework sequences analysis, for example, as described in Knappik et al., J. Mol. Biol. 296:57-86, 2000). Human antibodies may include amino acid residues not encoded by human sequences (e.g., mutations introduced by random or site-specific mutagenesis in vitro or by somatic mutation in vivo, or a conservative substitution to promote stability or manufacturing).

The term "corresponding human germline sequence" refers to a nucleic acid sequence encoding a human variable region amino acid sequence or subsequence that shares the highest determined amino acid sequence identity with a reference variable region amino acid sequence or subsequence in comparison to all other all other known variable region amino acid sequences encoded by human germline immunoglobulin variable region sequences. A corresponding human germline sequence can also refer to the human variable region amino acid sequence or subsequence with the highest amino acid sequence identity with a reference variable region amino acid sequence or subsequence in comparison to all other evaluated variable region amino acid sequences. A corresponding human germline sequence can be framework regions only, complementary determining regions only, framework and complementary determining regions, a variable segment (as defined above), or other combinations of sequences or subsequences that comprise a variable region. Sequence identity can be determined using the methods described herein, for example, aligning two sequences using BLAST, ALIGN, or another alignment algorithm known in the art. The corresponding human germline nucleic acid or amino acid sequence can have at least about 90%, 91%, 92%, 93%, 94%, 95%, 96%, 97%, 98%, 99%, or 100% sequence identity with the reference variable region nucleic acid or amino acid sequence.

The term "valency" as used herein refers to the number of potential target binding sites in a polypeptide. Each target binding site specifically binds one target molecule or a specific site on a target molecule. When a polypeptide comprises more than one target binding site, each target binding site may specifically bind the same or different molecules (e.g., may bind to different molecules, e.g., different antigens, or different epitopes on the same molecule). A conventional antibody, for example, has two binding sites and is bivalent; "trivalent" and "tetravalent" refer to the presence of three binding sites and four binding sites, respectively, in an antibody molecule. The antibody cytokine engrafted proteins can be monovalent (i.e., bind one target molecule), bivalent, or multivalent (i.e., bind more than one target molecule).

The phrase "specifically binds" or "binding specificity" when used in the context of describing the interaction between a target (e.g., a protein) and an antibody cytokine engrafted protein, refers to a binding reaction that is determinative of the presence of the target in a heterogeneous population of proteins and other biologics, e.g., in a biological sample, e.g., a blood, serum, plasma or tissue sample. Thus, under certain designated conditions, an antibody cytokine engrafted protein with a particular binding specificity binds to a particular target at least two times the background and does not substantially bind in a significant amount to other targets present in the sample. In one embodiment, under designated conditions, an antibody cytokine engrafted protein with a particular binding specificity binds to a particular antigen at least ten (10) times the background and does not substantially bind in a significant amount to other targets present in the sample. Specific binding to an antibody cytokine engrafted protein under such conditions can require an antibody cytokine engrafted protein to have been selected for its specificity for a particular target protein. As used herein, specific binding includes antibody cytokine engrafted proteins that selectively bind to human IL2 high affinity receptor and do not include antibody cytokine engrafted proteins that cross-react with, e.g., other cytokine receptor superfamily members. In some embodiments, antibody cytokine engrafted proteins are selected that selectively bind to human IL2 high affinity receptor and cross-react with non-human primate IL2R (e.g., cynomolgus IL2R). In some embodiments, antibody engrafted proteins are selected that selectively bind to human IL2 high affinity receptor and react with an additional target antigen. A variety of formats may be used to select antibody cytokine engrafted proteins that are specifically reactive with a particular target antigen protein. For example, solid-phase ELISA immunoassays are routinely used to select antibodies specifically immunoreactive with a protein (see, e.g., Harlow & Lane, Using Antibodies, A Laboratory Manual (1998), for a description of immunoassay formats and conditions that can be used to determine specific immunoreactivity). Typically a specific or selective binding reaction will produce a signal at least twice over the background signal and more typically at least than 10 to 100 times over the background.

The term "equilibrium dissociation constant ($K_D$, M)" refers to the dissociation rate constant ($k_d$, time$^{-1}$) divided by the association rate constant ($k_a$, time$^{-1}$, M$^{-1}$). Equilibrium dissociation constants can be measured using any known method in the art. The antibody cytokine engrafted proteins generally will have an equilibrium dissociation constant of less than about $10^{-7}$ or $10^{-8}$ M, for example, less than about $10^{-9}$ M or $10^{-19}$ M, in some embodiments, less than about $10^{-11}$ $^M$, $10^{-12}$ M or $10^{-13}$ M.

As used herein, the term "epitope" or "binding region" refers to a domain in the antigen protein that is responsible for the specific binding between the antibody CDRs and the antigen protein.

As used herein, the term "receptor-cytokine binding region" refers to a domain in the engrafted cytokine portion of the antibody cytokine engrafted protein that is responsible for the specific binding between the engrafted cytokine and its receptor (e.g. the IL2 high affinity receptor). There is at least one such receptor-cytokine binding region present in each antibody cytokine engrafted protein, and each of the binding regions can be identical or different from the others.

The term "agonist" interchangeably refer to an antibody capable of activating a receptor to induce a full or partial receptor-mediated response. For example, an agonist of the IL2 high affinity receptor binds to the IL2 high affinity receptor and induces IL2-mediated intracellular signaling, cell activation and/or proliferation of Treg cells. The antibody cytokine engrafted protein agonist stimulates signaling through the IL2 high affinity receptor similarly in some respects to the native IL2 ligand. The binding of IL2 to the IL2 high affinity receptor induces Jak1 and Jak2 activation which results in STAT5 phosphorylation. In some embodiments, an antibody cytokine engrafted protein agonist can be identified by its ability to bind IL2 high affinity receptor and induce STAT5 phosphorylation, and/or proliferation of Treg cells.

The term "IL2" or "IL-2" or "interleukin 2" or "interleukin-2", interchangeably, refer to an alpha helical cytokine family member wherein the native protein functions in the regulation and maintenance of inflammatory processes. A property of IL2 is that the N and C-termini are close to each other in space, which makes the IL2 cytokine protein suitable for antibody grafting. IL2 comprising residues 21-153 of full length native human is utilized in the context of the agonist antibody cytokine engrafted proteins. The human IL2 as disclosed herein has over its full length at least about 90%, 91%, 92%, 93%, 94%, 95%, 96%, 97%, 98%, 99%, or 100% sequence identity with the amino acid SEQ ID NO:2, and retains preferential agonist activity of the antibody cytokine engrafted proteins as described herein and has been published as GenBank Accession No: NP_000577. SEQ ID NO:1 is the human IL2 cDNA sequence. The human IL2 nucleic acid encoding for the IL2 protein as disclosed herein has over its full length at least about 90%, 91%, 92%, 93%, 94%, 95%, 96%, 97%, 98%, 99%, or 100% sequence identity with the nucleic acid sequence of SEQ ID NO:1, and was published under GenBank Accession No: NM_000586.

The term "antibody cytokine engrafted protein" or "antibody cytokine graft" or "engrafted" means that at least one cytokine is incorporated directly within a CDR of the antibody, interrupting the sequence of the CDR. The cytokine can be incorporated within HCDR1, HCDR2, HCDR3, LCDR1, LCDR2 or LCDR3. The cytokine can be incorporated within HCDR1, HCDR2, HCDR3, LCDR1, LCDR2 or LCDR3 and incorporated toward the N-terminal sequence of the CDR or toward the C-terminal sequence of the CDR. The cytokine incorporated within a CDR can reduce the specific binding of the antibody portion to the original target protein or the antibody cytokine engrafted protein can retain its specific binding to its target protein. Exemplary cytokines include, but are not limited to; IL-1α, IL-1β, IL-2, IL-3, IL-4, IL-5, IL-6, IL-7, IL-8, IL-12, IFN-α, IFN-β, IFN-γ, GM-CSF, MIP-1α, MIP-1β, TGF-β, TNF-α, and TNF-β. It is also possible to engraft a cytokine into a specific CDR of one "arm" of the antibody and to engraft another, different cytokine into a CDR of the other "arm" of the antibody. For example, engrafting IL2 into the HCDR1 of one "arm" of the antibody and engrafting IL-7 into the LCDR1 of the other "arm" of the antibody cytokine engrafted protein, can create a dual function antibody cytokine engrafted protein.

The term "isolated," when applied to a nucleic acid or protein, denotes that the nucleic acid or protein is essentially free of other cellular components with which it is associated in the natural state. It is preferably in a homogeneous state. It can be in either a dry or aqueous solution. Purity and homogeneity are typically determined using analytical chemistry techniques such as polyacrylamide gel electrophoresis or high performance liquid chromatography. A protein that is the predominant species present in a preparation is substantially purified. In particular, an isolated gene is separated from open reading frames that flank the gene and encode a protein other than the gene of interest. The term "purified" denotes that a nucleic acid or protein gives rise to essentially one band in an electrophoretic gel. Particularly, it means that the nucleic acid or protein is at least 85% pure, more preferably at least 95% pure, and most preferably at least 99% pure.

The term "nucleic acid" or "polynucleotide" refers to deoxyribonucleic acids (DNA) or ribonucleic acids (RNA) and polymers thereof in either single- or double-stranded form. Unless specifically limited, the term encompasses nucleic acids containing known analogues of natural nucleotides that have similar binding properties as the reference nucleic acid and are metabolized in a manner similar to naturally occurring nucleotides. Unless otherwise indicated, a particular nucleic acid sequence also implicitly encompasses conservatively modified variants thereof (e.g., degenerate codon substitutions), alleles, orthologs, SNPs, and complementary sequences as well as the sequence explicitly indicated. Specifically, degenerate codon substitutions may be achieved by generating sequences in which the third position of one or more selected (or all) codons is substituted with mixed-base and/or deoxyinosine residues (Batzer et al., Nucleic Acid Res. 19:5081 (1991); Ohtsuka et al., J. Biol. Chem. 260:2605-2608 (1985); and Rossolini et al., Mol. Cell. Probes 8:91-98 (1994)).

The terms "polypeptide," "peptide," and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymer.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refer to compounds that have the same basic chemical structure as a naturally occurring amino acid, i.e., an α-carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions in a manner similar to a naturally occurring amino acid.

"Conservatively modified variants" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG, and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid that encodes a polypeptide is implicit in each described sequence.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles. The following eight groups each contain amino acids that are conservative substitutions for one another: 1) Alanine (A), Glycine (G); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); 6) Phenylalanine (F), Tyrosine (Y), Tryptophan (W); 7) Serine (S), Threonine (T); and 8) Cysteine (C), Methionine (M) (see, e.g., Creighton, Proteins (1984)).

"Percentage of sequence identity" is determined by comparing two optimally aligned sequences over a comparison window, wherein the portion of the polynucleotide sequence in the comparison window may comprise additions or deletions (i.e., gaps) as compared to the reference sequence (e.g., a polypeptide), which does not comprise additions or deletions, for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

The terms "identical" or percent "identity," in the context of two or more nucleic acids or polypeptide sequences, refer to two or more sequences or subsequences that are the same sequences. Two sequences are "substantially identical" if two sequences have a specified percentage of amino acid residues or nucleotides that are the same (i.e., at least 85%, 90%, 91%, 92%, 93%, 94%, 95%, 96%, 97%, 98%, 99% or 100% sequence identity over a specified region, or, when not specified, over the entire sequence of a reference sequence), when compared and aligned for maximum correspondence over a comparison window, or designated region as measured using one of the following sequence comparison algorithms or by manual alignment and visual inspection. The disclosure provides polypeptides or polynucleotides that are substantially identical to the polypeptides or polynucleotides, respectively, exemplified herein (e.g., the variable regions exemplified in any one of SEQ ID NO:20, SEQ ID NO:33, SEQ ID NO:46, SEQ ID NO:59, SEQ ID NO:72, SEQ ID NO:85, SEQ ID NO:98, or SEQ ID NO:111. The identity exists over a region that is at least about 15, 25 or 50 nucleotides in length, or more preferably over a region that is 100 to 500 or 1000 or more nucleotides in length, or over the full length of the reference sequence. With respect to amino acid sequences, identity or substantial identity can exist over a region that is at least 5, 10, 15 or 20 amino acids in length, optionally at least about 25, 30, 35, 40, 50, 75 or 100 amino acids in length, optionally at least about 150, 200 or 250 amino acids in length, or over the full length of the reference sequence. With respect to shorter amino acid sequences, e.g., amino acid sequences of 20 or fewer amino acids, substantial identity exists when one or two amino acid residues are conservatively substituted, according to the conservative substitutions defined herein.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

A "comparison window," as used herein, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well known in the art. Optimal alignment of sequences for comparison can be conducted, e.g., by the local homology algorithm of Smith and Waterman (1970) *Adv. Appl. Math.* 2:482c, by the homology alignment algorithm of Needleman and Wunsch (1970) *J. Mol. Biol.* 48:443, by the search for similarity method of Pearson and Lipman (1988) *Proc. Nat'l. Acad. Sci. USA* 85:2444, by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., Ausubel et al., *Current Protocols in Molecular Biology* (1995 supplement)).

Two examples of algorithms that are suitable for determining percent sequence identity and sequence similarity are the BLAST and BLAST 2.0 algorithms, which are described in Altschul et al. (1977) *Nuc. Acids Res.* 25:3389-3402, and Altschul et al. (1990) *J. Mol. Biol.* 215:403-410, respectively. Software for performing BLAST analyses is publicly available through the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always>0) and N (penalty score for mismatching residues; always<0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) or 10, M=5, N=−4 and a comparison of both strands. For amino acid sequences, the BLASTP program uses as defaults a wordlength of 3, and expectation (E) of 10, and the BLOSUM62 scoring matrix (see Henikoff and Henikoff (1989) *Proc. Natl. Acad. Sci. USA* 89:10915) alignments (B) of 50, expectation (E) of 10, M=5, N=−4, and a comparison of both strands.

The BLAST algorithm also performs a statistical analysis of the similarity between two sequences (see, e.g., Karlin and Altschul (1993) *Proc. Natl. Acad. Sci. USA* 90:5873-5787). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01, and most preferably less than about 0.001.

An indication that two nucleic acid sequences or polypeptides are substantially identical is that the polypeptide encoded by the first nucleic acid is immunologically cross reactive with the antibodies raised against the polypeptide encoded by the second nucleic acid, as described below. Thus, a polypeptide is typically substantially identical to a second polypeptide, for example, where the two peptides differ only by conservative substitutions. Another indication that two nucleic acid sequences are substantially identical is that the two molecules or their complements hybridize to each other under stringent conditions, as described below. Yet another indication that two nucleic acid sequences are substantially identical is that the same primers can be used to amplify the sequence.

The term "link," when used in the context of describing how the binding regions are connected within an antibody cytokine engrafted protein, encompasses all possible means for physically joining the regions. The multitude of binding regions are frequently joined by chemical bonds such as a covalent bond (e.g., a peptide bond or a disulfide bond) or a non-covalent bond, which can be either a direct bond (i.e., without a linker between two binding regions) or indirect bond (i.e., with the aid of at least one linker molecule between two or more binding regions).

An "immune related disorder" or "immune disease" refers to a dysfunction of the immune system, in which the body's own immune system attacks healthy tissue. The dysfunction can be in components of the immune cells, and includes both overactive and underactive immune systems.

The terms "subject," "patient," and "individual" interchangeably refer to a mammal, for example, a human or a non-human primate mammal. The mammal can also be a laboratory mammal, e.g., mouse, rat, rabbit, hamster. In some embodiments, the mammal can be an agricultural mammal (e.g., equine, ovine, bovine, porcine, camelid) or domestic mammal (e.g., canine, feline).

As used herein, the terms "treat," "treating," or "treatment" of any disease or disorder refer in one embodiment, to ameliorating the disease or disorder (i.e., slowing or arresting or reducing the development of the disease or at least one of the clinical symptoms thereof). In another embodiment, "treat," "treating," or "treatment" refers to alleviating or ameliorating at least one physical parameter including those which may not be discernible by the patient. In yet another embodiment, "treat," "treating," or "treatment" refers to modulating the disease or disorder, either physically, (e.g., stabilization of a discernible symptom), physiologically, (e.g., stabilization of a physical parameter), or both. In yet another embodiment, "treat," "treating," or "treatment" refers to preventing or delaying the onset or development or progression of a disease or disorder.

The term "therapeutically acceptable amount" or "therapeutically effective dose" interchangeably refer to an amount sufficient to effect the desired result (i.e., a reduction in inflammation, inhibition of pain, prevention of inflammation, inhibition or prevention of inflammatory response). In some embodiments, a therapeutically acceptable amount does not induce or cause undesirable side effects. A therapeutically acceptable amount can be determined by first administering a low dose, and then incrementally increasing that dose until the desired effect is achieved. A "prophylactically effective dosage," and a "therapeutically effective dosage," of an IL2 antibody cytokine engrafted protein can prevent the onset of, or result in a decrease in severity of, respectively, disease symptoms, including symptoms associated with immune related disorders.

The term "co-administer" refers to the simultaneous presence of two (or more) active agents in an individual. Active agents that are co-administered can be concurrently or sequentially delivered.

As used herein, the phrase "consisting essentially of" refers to the genera or species of active pharmaceutical agents included in a method or composition, as well as any inactive carrier or excipients for the intended purpose of the methods or compositions. In some embodiments, the phrase "consisting essentially of" expressly excludes the inclusion of one or more additional active agents other than an IL2 antibody cytokine engrafted protein. In some embodiments, the phrase "consisting essentially of" expressly excludes the inclusion of more additional active agents other than an IL2 antibody cytokine engrafted protein and a second co-administered agent.

The terms "a," "an," and "the" include plural referents, unless the context clearly indicates otherwise.

BRIEF DESCRIPTION OF THE DRAWINGS

FIG. 1 is a table of antibody cytokine engrafted constructs, showing that IgG.IL2D49A.H1 preferentially expands Tregs in comparison to recombinant IL2 (Proleukin®).

FIG. 2 is a table comparing antibody cytokine engrafted proteins with recombinant IL2 (Proleukin®). Note that the IgG.IL2D49A.H1 molecule stimulates the IL2 receptor on Treg cells, but not on T effector cells (Teff) or NK cells as measured by STAT5 phosphorylation. This molecule also has a longer half-life than Proleukin® and causes greater expansion of Treg cells in vivo.

FIG. 3 is a table of the fold changes in a panel of different immunomodulatory cell types when equimolar doses of antibody cytokine engrafted proteins are compared to Proleukin®.

FIG. 14 is a table of dose ranges used in the pre-diabetic NOD mouse model, and compares equimolar amounts of Proleukin®.

FIG. 16 shows a graph of ELISA data showing that when IL2 is engrafted into CDRH1 of an anti-RSV antibody, RSV binding is maintained. However, binding to RSV is reduced when IL2 is engrafted into CDRL3. When IL2 is engrafted into a different antibody backbone (Xolair), there is no binding to RSV.

FIG. 18 shows experimental data on effects of increasing concentrations of a crosslinker anti-human IgG antibody on the selective activities of GFTX3b_IL-2-H1-D49A.

FIG. 20 shows experimental data on GFTX3b_IL-2-H1-D49A having higher selectivity than Proleukin for signaling in Tregs over T effector cells in human PBMC.

ANTIBODY CYTOKINE ENGRAFTED PROTEINS TARGETING THE IL2 HIGH AFFINITY RECEPTOR

Figure 4:
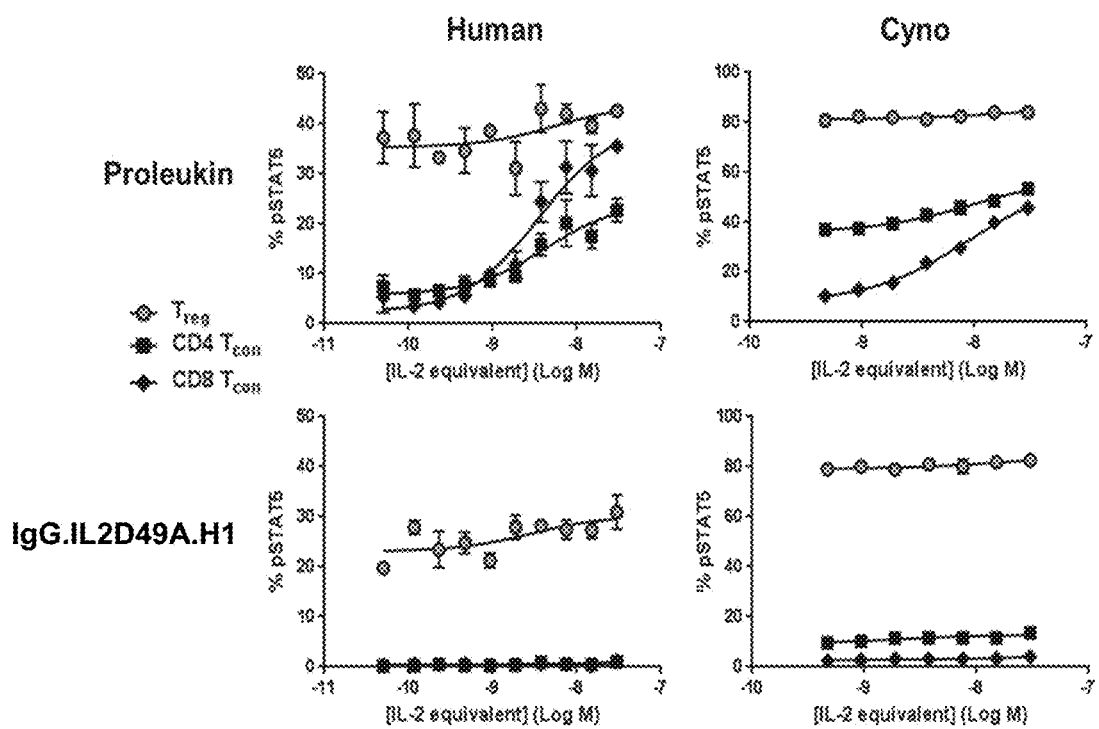
FIG. 4 shows experimental data on differential activation of the IL2 low affinity or high affinity receptor by antibody cytokine engrafted protein as compared to Proleukin® and as measured by STAT5 phosphorylation. Note that the IgG.IL2D49A.H1 stimulates the high affinity IL2 receptors expressed on Treg cells but not on CD4+ or CD8+ Tcon cells.

Provided herein are protein constructs comprising IL2 engrafted to into the complementarity determining region (CDR) of an antibody. The antibody cytokine engrafted proteins show suitable properties to be used in human patients, for example, they retain immunostimulatory activity similar to that of native or recombinant human IL2. However, the negative effects are diminished, for example stimulation of NK cells. Other activities and characteristics are also demonstrated throughout the specification. Thus, provided are antibody cytokine engrafted proteins having an improved therapeutic profile over previously known IL2 and modified IL2 therapeutic agents, such as Proleukin®, and methods of use of the provided antibody cytokine engrafted proteins in therapy.

Accordingly, the present disclosure provides antibody cytokine engrafted proteins that are agonists of the IL2 high affinity receptor, with selective activity profiles. Provided antibody cytokine engrafted proteins comprising an immunoglobulin heavy chain sequence and an immunoglobulin light chain sequence. Each immunoglobulin heavy chain sequence comprises a heavy chain variable region (VH) and a heavy chain constant region (CH), wherein the heavy chain constant region consists of CH1, CH2, and CH3 constant regions. Each immunoglobulin light chain sequence comprises a light chain variable region (VL) and a light chain constant region (CL). In each antibody cytokine engrafted protein an IL2 molecule is incorporated into a complementarity determining region (CDR) of the VH or VL of the antibody.

In some embodiments, the antibody cytokine engrafted protein comprises an IL2 molecule incorporated into a heavy chain CDR. In certain embodiments the IL2 molecule is incorporated into heavy chain complementarity determining region 1 (HCDR1). In certain embodiments the IL2 molecule is incorporated into heavy chain complementarity determining region 2 (HCDR2). In certain embodiments the IL2 molecule is incorporated into heavy chain complementarity determining region 3 (HCDR3).

In some embodiments, the antibody cytokine engrafted protein comprises an IL2 molecule incorporated into a light chain CDR. In certain embodiments the IL2 molecule is incorporated into light chain complementarity determining region 1 (LCDR1). In certain embodiments the IL2 molecule is incorporated into light chain complementarity determining region 2 (LCDR2). In certain embodiments the IL2 molecule is incorporated into light chain complementarity determining region 3 (LCDR3).

In some embodiments, the antibody cytokine engrafted comprises an IL2 sequence incorporated into a CDR, whereby the IL2 sequence is inserted into the CDR sequence. The insertion can be at or near the N-terminal region of the CDR, in the middle region of the CDR or at or near the C-terminal region of the CDR. In other embodiments, the antibody cytokine engrafted comprises an IL2 molecule incorporated into a CDR, whereby the IL2 sequence replaces all or part of a CDR sequence. A replacement can be the N-terminal region of the CDR, in the middle region of the CDR or at or near the C-terminal region the CDR. A replacement can be as few as one or two amino acids of a CDR sequence, or the entire CDR sequence.

In some embodiments the IL2 molecule is engrafted directly into a CDR without a peptide linker, with no additional amino acids between the CDR sequence and the IL2 sequence.

In some embodiments antibody cytokine engrafted proteins comprise immunoglobulin heavy chains of an IgG class antibody heavy chain. In certain embodiments an IgG heavy chain is any one of an IgG1, an IgG2 or an IgG4 subclass.

In some embodiments antibody cytokine engrafted proteins comprise heavy and light chain immunoglobulin sequences selected from a known, clinically utilized immunoglobulin sequence. In certain embodiments antibody cytokine engrafted proteins comprise heavy and light chain immunoglobulin sequences which are humanized sequences. In other certain embodiments antibody cytokine engrafted proteins comprise heavy and light chain immunoglobulin sequences which are human sequences.

In some embodiments antibody cytokine engrafted proteins comprise heavy and light chain immunoglobulin sequences selected from germline immunoglobulin sequences.

In some embodiments antibody cytokine engrafted proteins comprise heavy and light chain immunoglobulin sequences having binding specificity of the immunoglobulin variable domains to a target distinct from the binding specificity of the IL2 molecule. In some embodiments the binding specificity of the immunoglobulin variable domain to its target is retained by 10%, 20%, 30%, 40%, 50%, 60%, 70%, 80%, 90%, 95%, 98%, 99%, or 100%, in the presence of the engrafted cytokine. In certain embodiments the retained binding specificity is to a non-human target. In certain embodiments the retained binding specificity it to a virus, for example, RSV. In other embodiments the binding specificity is to a human target having therapeutic utility in conjunction with an IL2 therapy. In certain embodiments, targeting the binding specificity of the immunoglobulin conveys additional therapeutic benefit to the IL2 component. In certain embodiments the binding specificity of the immunoglobulin to its target conveys synergistic activity with IL2.

In still other embodiments, the binding specificity of the immunoglobulin to its target is reduced 10%, 20%, 30%, 40%, 50%, 60%, 70%, 80%, 90%, 95%, 98%, 99%, or 100% by the engrafting of the IL2 molecule.

Provided antibody cytokine engrafted proteins comprise an IL2 molecule incorporated into a complementarity determining region (CDR) of the VH or VL of the antibody cytokine engrafted protein. In some embodiments, the IL2 sequence has at least 85%, 90%, 91%, 92%, 93%, 94%, 95%, 96%, 97%, 98%, 99% or 100% sequence identity to the amino acid sequence of SEQ ID NO:4. In some embodiments, the IL2 molecule comprises the sequence of SEQ ID NO:4. In some embodiments, the IL2 molecule consists of the sequence of SEQ ID NO:4. Provided antibody cytokine engrafted proteins comprise an IL2 molecule incorporated into a complementarity determining region (CDR) of the VH or VL of the antibody cytokine engrafted protein. In some embodiments, the IL2 sequence has at least 85%, 90%, 91%, 92%, 93%, 94%, 95%, 96%, 97%, 98%, 99% or 100% sequence identity to the amino acid sequence of SEQ ID NO:4. In some embodiments, the IL2 molecule comprises the sequence of SEQ ID NO:4. In some embodiments, the IL2 molecule consists of the sequence of SEQ ID NO:4.

Provided antibody cytokine engrafted proteins comprise an IL2 molecule incorporated into a complementarity determining region (CDR) of the VH or VL of the antibody cytokine engrafted protein. In some embodiments, the IL2 sequence has at least 85%, 90%, 91%, 92%, 93%, 94%, 95%, 96%, 97%, 98%, 99% or 100% sequence identity to the amino acid sequence of SEQ ID NO:6. In some embodiments, the IL2 molecule comprises the sequence of SEQ ID NO:6. In some embodiments, the IL2 molecule consists of the sequence of SEQ ID NO:6. Provided antibody cytokine engrafted proteins comprise an IL2 molecule incorporated into a complementarity determining region (CDR) of the VH or VL of the antibody cytokine engrafted protein. In some embodiments, the IL2 sequence has at least 85%, 90%, 91%, 92%, 93%, 94%, 95%, 96%, 97%, 98%, 99% or 100% sequence identity to the amino acid sequence of SEQ ID NO:6. In some embodiments, the IL2 molecule comprises the sequence of SEQ ID NO:6. In some embodiments, the IL2 molecule consists of the sequence of SEQ ID NO:6.

In some embodiments, the antibody cytokine engrafted confers anti-inflammatory properties superior to human IL2, recombinant human IL2 or Proleukin®. In some embodiments, the antibody cytokine engrafted proteins disclosed herein confer increased activity on Treg cells while providing reduced proportional pro-inflammatory activity as compared to human IL2, recombinant human IL2 or Proleukin®. In some embodiments, the antibody cytokine engrafted proteins disclosed herein provide preferential stimulation of the high affinity IL2 receptor®. In some embodiments, the antibody cytokine engrafted proteins disclosed herein provide preferential activation of Treg cells over Teff cells, Tcon cells, and/or NK cells. In some embodiments, the antibody cytokine engrafted proteins disclosed herein provide preferential expansion of Treg cells over Teff cells, Tcon cells, and/or NK cells. In some embodiments, the antibody cytokine engrafted proteins disclosed herein provide increased expansion of Treg cells without expansion of CD8 T effector cells or NK cells. In some embodiments, the antibody cytokine engrafted proteins disclosed herein provide a ratio of expansion of Treg cells : NK cells that is, is about, is greater than, 1, 2, 3, 4, 5, 6, 7, 8, 9, 10. In some embodiments, the antibody cytokine engrafted proteins disclosed herein provide a ratio of expansion of Treg cells : CD8 T effector cells that is, is about, is greater than, 1, 2, 3, 4, 5, 6, 7, 8, 9, 10. In some embodiments, the antibody cytokine engrafted proteins disclosed herein provide a ratio of expansion of Treg cells : CD4 Tcon cells that is, is about, is greater than, 1, 2, 3, 4, 5, 6, 7, 8, 9, 10.

In some embodiments, the antibody cytokine engrafted proteins disclosed herein provide IL-2R signalling potency that is reduced in CD4 Tcon cells in comparison to human IL2, recombinant human IL2 or Proleukin®. In some embodiments, the antibody cytokine engrafted proteins disclosed herein provide IL-2R signalling potency that is reduced in CD8 Teff cells in comparison to human IL2, recombinant human IL2 or Proleukin®. In some embodiments, the antibody cytokine engrafted proteins disclosed herein provide IL-2R signalling potency that is reduced in NK cells in comparison to human IL2, recombinant human IL2 or Proleukin®. In some embodiments, the antibody cytokine engrafted proteins disclosed herein provide specific activation of Treg cells over CD4 T effector cells that is about 1,000 fold, about 2,000 fold, about 3,000 fold, about 4,000 fold, about 5,000 fold, about 6,000 fold, about 7,000 fold, about 8,000 fold, about 9,000 fold, about 10,000 fold, or more, higher than human IL2, recombinant human IL2 or Proleukin®. In some embodiments, the antibody cytokine engrafted proteins disclosed herein provide specific activation of Treg cells over CD8 T effector cells that is about 100 fold, about 200 fold, about 300 fold, about 400 fold, about 500 fold, about 600 fold, about 700 fold, about 800 fold, about 900 fold, about 1,000 fold, or more, higher than human IL2, recombinant human IL2 or Proleukin®. In some embodiments, the antibody cytokine engrafted proteins disclosed herein provide specific activation of Treg cells over CD8 T effector/memory cells that is about 100 fold, about 200 fold, about 300 fold, about 400 fold, about 500 fold, about 600 fold, about 700 fold, about 800 fold, about 900 fold, about 1,000 fold, or more, higher than human IL2, recombinant human IL2 or Proleukin®.

In some embodiments, the antibody cytokine engrafted proteins disclosed herein provide reduced toxicity, such as expansion of eosinophilia, in comparison to human IL2, recombinant human IL2 or Proleukin®. In some embodiments, the antibody cytokine engrafted proteins disclosed herein provide increased half life, such as more than 4 hours, more than 6 hours, more than 8 hours, more than 12 hours, more than 24 hours, more than 48 hours, in comparison to human IL2, recombinant human IL2 or Proleukin®. In some embodiments, the antibody cytokine engrafted proteins disclosed herein provide reduced body weight loss, such as in graft versus host disease (GvHD) patients, in comparison to human IL2, recombinant human IL2 or Proleukin®. In some embodiments, the antibody cytokine engrafted proteins disclosed herein provide better protection against type 1 diabetes development in comparison to human IL2, recombinant human IL2 or Proleukin®.

In some embodiments, the antibody cytokine engrafted proteins comprise a modified immunoglobulin IgG having a modified Fc conferring modified effector function. In certain embodiments the modified Fc region comprises a mutation selected from one or more of D265A, P329A, P329G, N297A, L234A, and L235A. In particular embodiments the immunoglobulin heavy chain may comprise a mutation or combination of mutations conferring reduced effector function selected from any of D265A, P329A, P329G, N297A, D265A/P329A, D265A/N297A, L234/L235A, P329A/L234A/L235A, and P329G/L234A/L235A.

In some embodiments, the antibody cytokine engrafted proteins comprise (i) a heavy chain variable region having at least 85%, 89%, 90%, 91%, 92%, 93%, 94%, 95%, 96%, 97%, 98%, 99%, or 100% amino acid sequence identity to a heavy chain variable region of SEQ ID NO:20 and (ii) a light chain variable region having at least 85%, 89%, 90%, 91%, 92%, 93%, 94%, 95%, 96%, 97%, 98%, 99%, or 100% amino acid sequence identity to a light chain variable region of SEQ ID NO:33. The immunoglobulin chain is an IgG class selected from IgG1, IgG2, or IgG4. In certain embodiments the immunoglobulin optionally comprises a mutation or combination of mutations conferring reduced effector function selected from any of D265A, P329A, P329G, N297A, D265A/P329A, D265A/N297A, L234/L235A, P329A/L234A/L235A, and P329G/L234A/L235A.

In some embodiments, the antibody cytokine engrafted proteins comprise (i) a heavy chain variable region having at least 85%, 89%, 90%, 91%, 92%, 93%, 94%, 95%, 96%, 97%, 98%, 99%, or 100% amino acid sequence identity to a heavy chain variable region of SEQ ID NO:46 and (ii) a light chain variable region having at least 85%, 89%, 90%, 91%, 92%, 93%, 94%, 95%, 96%, 97%, 98%, 99%, or 100% amino acid sequence identity to a light chain variable region of SEQ ID NO:58. The immunoglobulin chain is an IgG class selected from IgG1, IgG2, or IgG4. In certain embodiments the immunoglobulin optionally comprises a mutation or combination of mutations conferring reduced effector function selected from any of D265A, P329A, P329G, N297A, D265A/P329A, D265A/N297A, L234/L235A, P329A/L234A/L235A, and P329G/L234A/L235A.

In some embodiments, the antibody cytokine engrafted proteins comprise (i) a heavy chain variable region having at least 85%, 89%, 90%, 91%, 92%, 93%, 94%, 95%, 96%, 97%, 98%, 99%, or 100% amino acid sequence identity to a heavy chain variable region of SEQ ID NO:71 and (ii) a light chain variable region having at least 85%, 89%, 90%, 91%, 92%, 93%, 94%, 95%, 96%, 97%, 98%, 99%, or 100% amino acid sequence identity to a light chain variable region of SEQ ID NO:84. The immunoglobulin chain is an IgG class selected from IgG1, IgG2, or IgG4. In certain embodiments the immunoglobulin optionally comprises a mutation or combination of mutations conferring reduced effector function selected from any of D265A, P329A, P329G, N297A, D265A/P329A, D265A/N297A, L234/L235A, P329A/L234A/L235A, and P329G/L234A/L235A.

In some embodiments, the antibody cytokine engrafted proteins comprise (i) a heavy chain variable region having at least 85%, 89%, 90%, 91%, 92%, 93%, 94%, 95%, 96%, 97%, 98%, 99%, or 100% amino acid sequence identity to a heavy chain variable region of SEQ ID NO:97 and (ii) a light chain variable region having at least 85%, 89%, 90%, 91%, 92%, 93%, 94%, 95%, 96%, 97%, 98%, 99%, or 100% amino acid sequence identity to a light chain variable region of SEQ ID NO:110. The immunoglobulin chain is an IgG class selected from IgG1, IgG2, or IgG4. In certain embodiments the immunoglobulin optionally comprises a mutation or combination of mutations conferring reduced effector function selected from any of D265A, P329A, P329G, N297A, D265A/P329A, D265A/N297A, L234/L235A, P329A/L234A/L235A, and P329G/L234A/L235A.

Engineered and Modified Antibody Cytokine Engrafted Proteins

In certain aspects, antibody cytokine engrafted proteins are generated by engrafting an IL2 sequence into a CDR region of an immunoglobulin scaffold. Both heavy and light chain immunoglobulin chains are produced to generate final antibody engrafted proteins. Antibody cytokine engrafted proteins confer preferred therapeutic activity on Treg cells, however, the antibody cytokine engrafted proteins have reduced pro-inflammatory activity as compared with native or recombinant human IL2 (rhIL2 or Proleukin®).

To engineer antibody cytokine engrafted proteins, IL2 sequences containing specific muteins (SEQ ID NO:4 or SEQ ID NO:6), are inserted into a CDR loop of an immunoglobulin chain scaffold protein. Engrafted constructs can be prepared using any of a variety of known immunoglobulin sequences which have been utilized in clinical settings, known immunoglobulin sequences which are in current discovery and/or clinical development, human germline antibody sequences, as well as sequences of novel antibody immunoglobulin chains. Constructs are produced using standard molecular biology methodology utilizing recombinant DNA encoding relevant sequences. Sequences of IL2 in an exemplary scaffold, referred to as GFTX3b, are depicted in TABLE 2. Insertion points were selected to be the mid-point of the loop based on available structural or homology model data, however, insertion points can be adjusted toward the N or C-terminal end of the CDR loop.

Thus the present disclosure provides for antibody cytokine engrafted proteins that specifically bind to the high affinity IL2 receptor comprising an IL2 protein recombinantly inserted into a heterologous antibody protein or polypeptide to generate antibody cytokine engrafted proteins. In particular, the disclosure provides antibody cytokine engrafted proteins comprising an antibody or antigen-binding fragment of an antibody described herein or any other relevant scaffold antibody polypeptide (e.g., a full antibody immunoglobulin protein, a Fab fragment, Fc fragment, Fv fragment, F(ab)2 fragment, a VH domain, a VH CDR, a VL domain, a VL CDR, etc.) and a heterologous cytokine protein, polypeptide, or peptide, e.g., IL2. Methods for fusing or conjugating proteins, polypeptides, or peptides to an antibody or an antibody fragment are known in the art. See, e.g., U.S. Pat. Nos. 5,336,603, 5,622,929, 5,359,046, 5,349,053, 5,447,851, and 5,112,946; European Patent Nos. EP 307,434 and EP 367,166; International Publication Nos. WO 96/04388 and WO 91/06570; Ashkenazi et al., 1991, Proc. Natl. Acad. Sci. USA 88: 10535-10539; Zheng et al., 1995, J. Immunol. 154:5590-5600; and Vil et al., 1992, Proc. Natl. Acad. Sci. USA 89:11337-11341. Additionally, antibody cytokine engrafted proteins can be generated through the techniques of gene-shuffling, motif-shuffling, exon-shuffling, and/or codon-shuffling (collectively referred to as "DNA shuffling"). DNA shuffling may be employed to prepare antibody cytokine engrafted proteins and/or to alter the activities of antibodies or fragments thereof (e.g., antibodies or fragments thereof with higher affinities and lower dissociation rates). See, generally, U.S. Patent Nos. 5,605,793, 5,811,238, 5,830,721, 5,834,252, and 5,837,458; Patten et al., 1997, Curr. Opinion Biotechnol. 8:724-33; Harayama, 1998, Trends Biotechnol. 16(2):76-82; Hansson, et al., 1999, J. Mol. Biol. 287:265-76; and Lorenzo and Blasco, 1998, Biotechniques 24(2):308-313 (each of these patents and publications are hereby incorporated by reference in its entirety). Antibodies or fragments thereof, or the encoded antibodies or fragments thereof, can be altered by being subjected to random mutagenesis by error-prone PCR, random nucleotide insertion or other methods prior to recombination. A polynucleotide encoding an antibody or fragment thereof that specifically binds to an antigen protein of interest may be recombined with one or more components, motifs, sections, parts, domains, fragments, etc. of one or more heterologous cytokine molecules, e.g., IL2, for preparation of antibody cytokine engrafted proteins as provided herein.

An antibody Fab contains six CDR loops, 3 in the light chain (CDRL1, CDRL2, CDRL3) and 3 in the heavy chain (CDRH1, CDRH2, CDRH3) which can serve as potential insertion sites for a cytokine protein. Structural and functional considerations are taken into account in order to determine which CDR loop(s) to insert the cytokine. As a CDR loop size and conformation vary greatly across different antibodies, the optimal CDR for insertion may be determined empirically for each particular antibody/protein combination. Additionally, since a cytokine protein will be inserted into a CDR loop, this can put additional constraints on the structure of the cytokine protein. For example, the amino and carboxy terminal of the cytokine protein should allow for possibility to be constrained relatively close in space (~25 Å). Additionally, an antibody cytokine engrafted protein should not rely on oligomerization for biological activity. An analysis of available protein database structures indicates that many cytokine proteins, including IL2, fall into this category.

CDRs of immunoglobulin chains are determined by well known numbering systems known in the art, including those described herein. For example, CDRs have been identified and defined by (1) using the numbering system described in Kabat et al. (1991), "Sequences of Proteins of Immunological Interest," 5th Ed. Public Health Service, National Institutes of Health, Bethesda, Md. ("Kabat" numbering scheme), NIH publication No. 91-3242; and (2) Chothia, see Al-Lazikani et al., (1997) "Standard conformations for the canonical structures of immunoglobulins," J.Mol.Biol. 273: 927-948. For identified CDR amino acid sequences less than 20 amino acids in length, one or two conservative amino acid residue substitutions can be tolerated while still retaining the desired specific binding and/or agonist activity.

An antibody cytokine engrafted protein further can be prepared using an antibody having one or more of the CDRs and/or VH and/or VL sequences shown herein (e.g., TABLE 2) as starting material to engineer a modified antibody cytokine engrafted protein, which may have altered properties from the starting antibody engrafted protein. Alternatively any known antibody sequences may be utilized as a scaffold to engineer modified antibody cytokine engrafted protein. For example, any known, clinically utilized antibody may be utilized as a starting materials scaffold for preparation of antibody engrafted protein. Known antibodies and corresponding immunoglobulin sequences include, e.g., palivizumab, alirocumab, mepolizumab, necitumumab, nivolumab, dinutuximab, secukinumab, evolocumab, blinatumomab, pembrolizumab, ramucirumab, vedolizumab, siltuximab, obinutuzumab, trastuzumab, raxibacumab, pertuzumab, belimumab, ipilimumab, denosumab, tocilizumab, ofatumumab, canakinumab, golimumab, ustekinumab, certolizumab, catumaxomab, eculizumab, ranibizumab, panitumumab, natalizumab, bevacizumab, cetuximab, efalizumab, omalizumab, tositumomab, ibritumomab tiuxetan, adalimumab, alemtuzumab, gemtuzumab, infliximab, basiliximab, daclizumab, rituximab, abciximab, muromonab, or modifications thereof. Known antibodies and immunoglobulin sequences also include germline antibody sequences. Framework sequences can be obtained from public DNA databases or published references that include germline antibody gene sequences. For example, germline DNA sequences for human heavy and light chain variable region genes can be found in the "VBase" human germline sequence database as well as in Kabat, E. A., et al., 1991 Sequences of Proteins of Immunological Interest, Fifth Edition, U.S. Department of Health and Human Services, NIH Publication No. 91-3242; Tomlinson, I. M., et al., 1992 J. fol. Biol. 227:776-798; and Cox, J. P. L. et al., 1994 Eur. J Immunol. 24:827-836. In still other examples, antibody and corresponding immunoglobulin sequences from other known entities which may be in early discovery and/or drug development can be similarly adapted as starting material to engineer a modified antibody cytokine engrafted protein.

A wide variety of antibody/immunoglobulin frameworks or scaffolds can be employed so long as the resulting polypeptide includes at least one binding region which accommodates incorporation of a cytokine (e.g., IL2). Such frameworks or scaffolds include the 5 main idiotypes of human immunoglobulins, or fragments thereof, and include immunoglobulins of other animal species, preferably having humanized and/or human aspects. Novel antibodies, frameworks, scaffolds and fragments continue to be discovered and developed by those skilled in the art.

Antibodies can be generated using methods that are known in the art. For preparation of monoclonal antibodies, any technique known in the art can be used (see, e.g., Kohler & Milstein, *Nature* 256:495-497 (1975); Kozbor et al., *Immunology Today* 4:72 (1983); Cole et al., Monoclonal Antibodies and Cancer Therapy, pp. 77-96. Alan R. Liss, Inc. 1985). Techniques for the production of single chain antibodies (U.S. Pat. No. 4,946,778) can be adapted to produce antibodies for use in antibody cytokine engrafted proteins. Also, transgenic mice, or other organisms such as other mammals, may be used to express and identify primatized or humanized or human antibodies. Alternatively, phage display technology can be used to identify antibodies and heteromeric Fab fragments that specifically bind to selected antigens for use in antibody cytokine engrafted proteins (see, e.g., McCafferty et al., supra; Marks et al., *Biotechnology*, 10:779-783, (1992)).

Methods for primatizing or humanizing non-human antibodies are well known in the art. Generally, a primatized or humanized antibody has one or more amino acid residues introduced into it from a source which is non-primate or non-human. Such non-primate or non-human amino acid residues are often referred to as import residues, which are typically taken from an import variable domain. Humanization can be essentially performed following the method of Winter and co-workers (see, e.g., Jones et al., *Nature* 321: 522-525 (1986); Riechmann et al., *Nature* 332:323-327 (1988); Verhoeyen et al., *Science* 239:1534-1536 (1988) and Presta, *Curr. Op. Struct. Biol.* 2:593-596 (1992)), by substituting rodent CDRs or CDR sequences for the corresponding sequences of a human antibody. Accordingly, such humanized antibodies are chimeric antibodies (U.S. Pat. No. 4,816,567), wherein substantially less than an intact human variable domain has been substituted by the corresponding sequence from a non-human species. In practice, primatized or humanized antibodies are typically primate or human antibodies in which some complementary determining region ("CDR") residues and possibly some framework ("FR") residues are substituted by residues from analogous sites in an originating species (e.g., rodent antibodies) to confer binding specificity.

Alternatively or additionally, an in vivo method for replacing a nonhuman antibody variable region with a human variable region in an antibody while maintaining the same or providing better binding characteristics relative to that of the nonhuman antibody may be utilized to convert non-human antibodies into engineered human antibodies. See, e.g., U.S. Patent Publication No. 20050008625, U.S. Patent Publication No. 2005/0255552. Alternatively, human V segment libraries can be generated by sequential cassette replacement in which only part of the reference antibody V segment is initially replaced by a library of human sequences; and identified human "cassettes" supporting binding in the context of residual reference antibody amino acid sequences are then recombined in a second library screen to generate completely human V segments (see, U.S. Patent Publication No. 2006/0134098).

Various antibodies or antigen-binding fragments for use in preparation of antibody cytokine engrafted proteins can be produced by enzymatic or chemical modification of the intact antibodies, or synthesized de novo using recombinant DNA methodologies (e.g., single chain Fv), or identified using phage display libraries (see, e.g., McCafferty et al., Nature 348:552-554, 1990). For example, minibodies can be generated using methods described in the art, e.g., Vaughan and Sollazzo, Comb Chem High Throughput Screen. 4:417-30 2001. Bispecific antibodies can be produced by a variety of methods including engrafted of hybridomas or linking of Fab' fragments. See, e.g., Songsivilai & Lachmann, Clin. Exp. Immunol. 79:315-321 (1990); Kostelny et al., J. Immunol. 148, 1547-1553 (1992). Single chain antibodies can be identified using phage display libraries or ribosome display libraries, gene shuffled libraries. Such libraries can be constructed from synthetic, semi-synthetic or native and immunocompetent sources. Selected immunoglobulin sequences may thus be utilized in preparation of antibody cytokine engrafted protein constructs as provided herein.

Antibodies, antigen-binding molecules or antibody cytokine engrafted molecules of the present disclosure further include bispecific antibodies. A bispecific or bifunctional antibody is an artificial hybrid antibody having two different heavy/light chain pairs and two different binding sites. Other antigen-binding fragments or antibody portions include bivalent scFv (diabody), bispecific scFv antibodies where the antibody molecule recognizes two different epitopes, single binding domains (dAbs), and minibodies. Selected immunoglobulin sequences can thus be utilized in preparation of antibody cytokine engrafted protein constructs as provided herein.

Antigen-binding fragments of antibodies e.g., a Fab fragment, scFv, can be used as building blocks to construct antibody cytokine engrafted proteins, and may optionally include multivalent formats. In some embodiments, such multivalent molecules comprise a constant region of an antibody (e.g., Fc).

Antibody cytokine engrafted proteins can be engineered by modifying one or more residues within one or both variable regions (i.e., VH and/or VL) of an antibody, for example within one or more CDR regions, and such adapted VH and/or VL region sequences utilized for engrafting a cytokine or for preparation of cytokine engrafting. Antibodies interact with target antigens predominantly through amino acid residues that are located in the six heavy and light chain complementarity determining regions (CDRs). For this reason, the amino acid sequences within CDRs are more diverse between individual antibodies than sequences outside of CDRs. CDR sequences are responsible for most antibody-antigen interactions, it is possible to express recombinant antibodies that mimic the properties of a specific antibody by constructing expression vectors that include CDR sequences from a specific antibody grafted onto framework sequences from a different antibody with different properties (see, e.g., Riechmann, L. et al., 1998 Nature 332:323-327; Jones, P. et al., 1986 Nature 321:522-525; Queen, C. et al., 1989 Proc. Natl. Acad., U.S.A. 86:10029-10033; U.S. Pat. No. 5,225,539 to Winter, and U.S. Pat. Nos. 5,530,101; 5,585,089; 5,693,762 and 6,180,370 to Queen et al.). In certain instances it is beneficial to mutate residues within the framework regions to maintain or enhance the antigen binding ability of the antibody (see e.g., U.S. Pat. Nos. 5,530,101; 5,585,089; 5,693,762 and 6,180,370 to Queen et al).

In some aspects mutation of amino acid residues within the VH and/or VL CDR1, CDR2, and/or CDR3 regions to thereby improve one or more binding properties (e.g., affinity) of the antibody of interest, known as "affinity maturation," can be beneficial, e.g., to optimize antigen binding of an antibody in conjunction with the context of the cytokine engrafted protein. Site-directed mutagenesis or PCR-mediated mutagenesis can be performed to introduce the mutation(s) and the effect on antibody binding, or other functional property of interest, can be evaluated in in vitro or in vivo assays as described herein and provided in the Examples and/or alternative or additional assays known in the art. Conservative modifications can be introduced. The mutations may be amino acid substitutions, additions or deletions. Moreover, typically no more than one, two, three, four or five residues within a CDR region are altered.

Engineered antibodies or antibody fragments include those in which modifications have been made to framework residues within VH and/or VL, e.g. to improve the properties of the antibody. In some embodiments such framework modifications are made to decrease immunogenicity of the antibody. For example, one approach is to change one or more framework residues to the corresponding germline sequence. More specifically, an antibody that has undergone somatic mutation may contain framework residues that differ from germline sequence from which the antibody is derived. Such residues can be identified by comparing the antibody framework sequences to the germline sequences from which the antibody is derived. To return the framework region sequences to their germline configuration, the somatic mutations can be "backmutated" to the germline sequence by, for example, site-directed mutagenesis. Additional framework modification involves mutating one or more residues within the framework region, or even within one or more CDR regions, to remove T cell epitopes to thereby reduce the potential immunogenicity of the antibody. This approach is also referred to as "deimmunization" and is described in further detail in U.S. Patent Publication No. 20030153043 by Carr et al.

Constant regions of the antibodies or antibody fragments utilized for preparation of the antibody cytokine engrafted protein can be any type or subtype, as appropriate, and can be selected to be from the species of the subject to be treated by the present methods (e.g., human, non-human primate or other mammal, for example, agricultural mammal (e.g., equine, ovine, bovine, porcine, camelid), domestic mammal (e.g., canine, feline) or rodent (e.g., rat, mouse, hamster, rabbit). In some embodiments antibodies utilized in antibody cytokine engrafted proteins are engineered to generate humanized or Humaneered® antibodies. In some embodiments antibodies utilized in antibody cytokine engrafted proteins are human antibodies. In some embodiments, antibody constant region isotype is IgG, for example, IgG1, IgG2, IgG3, IgG4. In certain embodiments the constant region isotype is IgGi. In some embodiments, antibody cytokine engrafted proteins comprise an IgG. In some embodiments, antibody cytokine engrafted proteins comprise an IgG1 Fc. In some embodiments, antibody cytokine engrafted proteins comprise an IgG2 Fc.

In addition or alternative to modifications made within framework or CDR regions, antibodies or antibody fragments utilized in preparation of antibody cytokine engrafted proteins may be engineered to include modifications within an Fc region, typically to alter one or more functional properties of the antibody, such as, e.g., serum half-life, complement fixation, Fc receptor binding, and/or antigen-dependent cellular cytotoxicity. Furthermore, an antibody, antibody fragment, or antibody cytokine engrafted protein can be chemically modified (e.g., one or more chemical moieties can be attached to the antibody) or be modified to alter its glycosylation, again to alter one or more functional properties of the antibody cytokine engrafted protein.

In one embodiment, a hinge region of CH1 is modified such that the number of cysteine residues in the hinge region is altered, e.g., increased or decreased. For example, by the approach is described further in U.S. Pat. No. 5,677,425 by Bodmer et al. wherein the number of cysteine residues in the hinge region of CH1 is altered to, for example, facilitate assembly of the light and heavy chains or to increase or decrease the stability of the antibody cytokine engrafted protein. In another embodiment, an Fc hinge region of an antibody is mutated to alter the biological half-life of the antibody cytokine engrafted protein. More specifically, one or more amino acid mutations are introduced into the CH2-CH3 domain interface region of the Fc-hinge fragment such that the antibody cytokine engrafted protein has impaired Staphylococcyl protein A (SpA) binding relative to native Fc-hinge domain SpA binding. This approach is described in further detail in U.S. Pat. No. 6,165,745 by Ward et al.

The present disclosure provides for antibody cytokine engrafted proteins that specifically bind to the IL2 high affinity receptor which have an extended half-life in vivo. In another embodiment, an antibody cytokine engrafted protein is modified to increase its biological half-life. Various approaches are possible. Antibody cytokine engrafted proteins having an increased half-life in vivo can also be generated introducing one or more amino acid modifications (i.e., substitutions, insertions or deletions) into an IgG constant domain, or FcRn binding fragment thereof (preferably a Fc or hinge Fc domain fragment). For example, one or more of the following mutations can be introduced: T252L, T254S, T256F, as described in U.S. Pat. No. 6,277,375 to Ward. See, e.g., International Publication No. WO 98/23289; International Publication No. WO 97/34631; and U.S. Pat. No. 6,277,375. Alternatively, to increase the biological half-life, the antibody cytokine engrafted protein is altered within the CH1 or CL region to contain a salvage receptor binding epitope taken from two loops of a CH2 domain of an Fc region of an IgG, as described in U.S. Pat. Nos. 5,869,046 and 6,121,022 by Presta et al. In yet other embodiments, the Fc region is altered by replacing at least one amino acid residue with a different amino acid residue to alter the effector functions of the antibody cytokine engrafted protein. For example, one or more amino acids can be replaced with a different amino acid residue such that the antibody cytokine engrafted protein has an altered affinity for an effector ligand but retains antigen-binding ability of the parent antibody. The effector ligand to which affinity is altered can be, for example, an Fc receptor (FcR) or the C1 component of complement. This approach is described in further detail in U.S. Pat. Nos. 5,624,821 and 5,648,260, both by Winter et al.

In another embodiment, one or more amino acids selected from amino acid residues can be replaced with a different amino acid residue such that the antibody cytokine engrafted protein has altered C1q binding and/or reduced or abolished complement dependent cytotoxicity (CDC). This approach is described in further detail in U.S. Pat. Nos. 6,194,551 by Idusogie et al.

Antibody cytokine engrafted proteins containing such mutations mediate reduced or no antibody-dependent cellular cytotoxicity (ADCC) or complement-dependent cytotoxicity (CDC). In some embodiments, amino acid residues L234 and L235 of the IgG1 constant region are substituted to Ala234 and Ala235. In some embodiments, amino acid residue N267 of the IgG1 constant region is substituted to Ala267.

In another embodiment, one or more amino acid residues are altered to thereby alter the ability of the antibody cytokine engrafted protein to fix complement. This approach is described further in PCT Publication WO 94/29351 by Bodmer et al.

In yet another embodiment, an Fc region is modified to increase the ability of the antibody to mediate antibody dependent cellular cytotoxicity (ADCC) and/or to increase the affinity of the antibody cytokine engrafted protein for an Fcγ receptor by modifying one or more amino acids. This approach is described further in PCT Publication WO 00/42072 by Presta. Moreover, binding sites on human IgG1 for FcγR1, FcγRII, FcγRIII and FcRn have been mapped and variants with improved binding have been described (see Shields, R. L. et al., 2001 J. Biol. Chen. 276:6591-6604).

In still another embodiment, glycosylation of an antibody cytokine engrafted protein is modified. For example, an aglycoslated antibody cytokine engrafted protein can be made (i.e., the antibody cytokine engrafted protein lacks glycosylation). Glycosylation can be altered to, for example, increase the affinity of the antibody for "antigen." Such carbohydrate modifications can be accomplished by, for example, altering one or more sites of glycosylation within the antibody sequence. For example, one or more amino acid substitutions can be made that result in elimination of one or more variable region framework glycosylation sites to thereby eliminate glycosylation at that site. Such aglycosylation may increase the affinity of the antibody for antigen. Such an approach is described in further detail in U.S. Pat. Nos. 5,714,350 and 6,350,861 by Co et al.

Additionally or alternatively, an antibody cytokine engrafted protein can be made that has an altered type of glycosylation, such as a hypofucosylated antibody cytokine engrafted protein having reduced amounts of fucosyl residues or an antibody having increased bisecting GlcNac structures. Such altered glycosylation patterns have been demonstrated to increase the antibody dependent cellular cytotoxicity (ADCC) ability of antibodies. Such carbohydrate modifications can be accomplished by, for example, expressing the antibody cytokine engrafted protein in a host cell with altered glycosylation machinery. Cells with altered glycosylation machinery have been described in the art and can be used as host cells in which to express recombinant antibody cytokine engrafted proteins to thereby produce an antibody cytokine engrafted protein with altered glycosylation. For example, EP 1,176,195 by Hang et al. describes a cell line with a functionally disrupted FUT8 gene, which encodes a fucosyl transferase, such that antibody cytokine engrafted proteins expressed in such a cell line exhibit hypofucosylation. PCT Publication WO 03/035835 by Presta describes a variant CHO cell line, Lec13 cells, with reduced ability to attach fucose to Asn(297)-linked carbohydrates, also resulting in hypofucosylation of antibody cytokine engrafted proteins expressed in that host cell (see also Shields, R. L. et al., 2002 J. Biol. Chem. 277:26733-26740). PCT Publication WO 99/54342 by Umana et al. describes cell lines engineered to express glycoprotein-modifying glycosyl transferases (e.g., beta(1,4)-N acetylglucosaminyltransferase III (GnTIII)) such that antibody cytokine engrafted proteins expressed in the engineered cell lines exhibit increased bisecting GlcNac structures which results in increased ADCC activity of the antibodies (see also Umana et al., 1999 Nat. Biotech. 17:176-180).

In some embodiments, one or more domains, or regions, of an antibody cytokine engrafted protein are connected via a linker, for example, a peptide linker, such as those that are well known in the art (see e.g., Holliger, P., et al. (1993) Proc. Natl. Acad. Sci. USA 90:6444-6448; Poljak, RJ., et al. (1994) Structure 2:1121-1123). A peptide linker may vary in length, e.g., a linker can be 1-100 amino acids in length, typically a linker is from five to 50 amino acids in length, e.g., 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 amino acids in length.

In some embodiments IL2 is engrafted into the CDR sequence optionally with one or more peptide linker sequences. In certain embodiments one or more peptide linkers is independently selected from a $(Gly_n\text{-}Ser)_m$ sequence (SEQ ID NO: 115), a $(Gly_n\text{-}Ala)_m$ sequence (SEQ ID NO: 116), or any combination of a $(Gly_n\text{-}Ser)_m/(Gly_n\text{-}Ala)_m$ sequence (SEQ ID NOS 115 and 116, respectively), wherein each n is independently an integer from 1 to 5 and each m is independently an integer from 0 to 10. Examples of linkers include, but are not limited to, glycine-based linkers or gly/ser linkers G/S such as $(G_mS)_n$ wherein n is a positive integer equal to 1, 2, 3, 4, 5, 6, 7, 8, 9, or 10 and m is an integer equal to 0, 1, 2, 3, 4, 5, 6, 7, 8, 9, or 10 (SEQ ID NO: 117). In certain embodiments one or more linkers include $G_4S$ repeats (SEQ ID NO: 118), e.g., the Gly-Ser linker $(G_4S)_n$ wherein n is a positive integer equal to or greater than 1 (SEQ ID NO: 118). For example, n=1, n=2, n=3. n=4, n=5 and n=6, n=7, n=8, n=9 and n=10. In some embodiments, Ser can be replaced with Ala e.g., linkers G/A such as $(G_mA)_n$ wherein n is a positive integer equal to 1, 2, 3, 4, 5, 6, 7, 8, 9, or 10 and m is an integer equal to 0, 1, 2, 3, 4, 5, 6, 7, 8, 9, or 10 (SEQ ID NO: 119). In certain embodiments one or more linkers include $G_4A$ repeats (SEQ ID NO: 120), $(G_4A)_n$ wherein n is a positive integer equal to or greater than 1 (SEQ ID NO: 120). For example, n=1, n=2, n=3. n=4, n=5 and n=6, n=7, n=8, n=9 and n=10. In some embodiments, the linker includes multiple repeats of linkers. In other embodiments, a linker includes combinations and multiples of $G_4S$ (SEQ ID NO: 118) and G4A (SEQ ID NO: 120).

Other examples of linkers include those based on flexible linker sequences that occur naturally in antibodies to minimize immunogenicity arising from linkers and junctions. For example, there is a natural flexible linkage between the variable domain and a CH1 constant domain in antibody molecular structure. This natural linkage comprises approximately 10-12 amino acid residues, contributed by 4-6 residues from C-terminus of V domain and 4-6 residues from the N-terminus of the CH1 domain. Antibody cytokine engrafted proteins can, e.g., employ linkers incorporating terminal 5-6 amino acid residues, or 11-12 amino acid residues, of CH1 as a linker. The N-terminal residues of the CH1 domain, particularly the first 5-6 amino acid residues, adopt a loop conformation without strong secondary structure, and, therefore, can act as a flexible linker. The N-terminal residues of the CH1 domain are a natural extension of the variable domains, as they are part of the Ig sequences, and, therefore, minimize to a large extent any immunogenicity potentially arising from the linkers and junctions. In some embodiments a linker sequence includes a modified peptide sequence based on a hinge sequence.

Moreover, the antibody cytokine engrafted proteins can be fused to marker sequences, such as a peptide to facilitate purification of antibody cytokine engrafted proteins. In preferred embodiments, a marker amino acid sequence is a hexa-histidine peptide (SEQ ID NO: 121), such as the tag provided in a pQE vector (QIAGEN, Inc., Chatsworth, Calif.), among others, many of which are commercially available. As described in Gentz et al., 1989, Proc. Natl. Acad. Sci. USA 86:821-824, for instance, hexa-histidine (SEQ ID NO: 121) provides for convenient purification of the engrafted protein. Other peptide tags useful for purification include, but are not limited to, the hemagglutinin ("HA") tag, which corresponds to an epitope derived from the influenza hemagglutinin protein (Wilson et al., 1984, Cell 37:767), and the "flag" tag.

Antibodies may also be attached to solid supports, which are particularly useful for immunoassays or purification of the target antigen. Such solid supports include, but are not limited to, glass, cellulose, polyacrylamide, nylon, polystyrene, polyvinyl chloride or polypropylene.

Assays for Antibody Cytokine Engrafted Protein Activity

Assays for identifying antibody cytokine engrafted proteins are known in the art and described herein. Agonist antibody cytokine engrafted proteins bind to the IL2 high affinity receptor and promote, induce, stimulate intracellular signaling resulting in Treg effects as well as immunostimulatory effects.

Binding of the antibody cytokine engrafted proteins to the IL2 high affinity receptor can be determined using any method known in the art. For example, binding to the IL2 high affinity receptor can be determined using known techniques, including without limitation ELISA, Western blots, surface plasmon resonance (e.g., BIAcore), and flow cytometry.

Intracellular signaling through the IL2 high affinity receptor can be measured using any method known in the art. For example, activation through IL2 promotes STAT5 activation and signaling. Methods for measuring STAT5 activation are standard in the art (e.g., phosphorylation status of STAT5 protein, reporter gene assays, downstream signaling assays, etc.). Activation through the IL2 high affinity receptor has increased Treg effects. Additionally, the reduced binding of the IL2 low affinity receptor reduces natural killer (NK) cell and CD 8 T effector cell proliferation. Methods for measuring proliferation of cells are standard in the art (e.g., $^3$H-thymidine incorporation assays, CFSE labeling). Methods for measuring cytokine production are well known in the art (e.g., ELISA assays, ELISpot assays). In performing in vitro assays, test cells or culture supernatant from test cells contacted with an agonist antibody cytokine engrafted proteins can be compared to control cells or culture supernatants from control cells that have not been contacted with an agonist antibody cytokine engrafted proteins and/or those that have been contacted with recombinant human IL2 (e.g. Proleukin®).

The activity of the antibody cytokine engrafted proteins can also be measured ex vivo and/or in vivo. In some aspects, methods for measuring STAT5 activation across various cell types ex vivo from animals treated with antibody cytokine engrafted proteins as compared to untreated control animals and/or animals similarly treated with Proleukin® can be used to show differential activity of the agonist antibody engrafted proteins across cell types. Preferred agonist antibody cytokine engrafted proteins have the ability to activate and expand Treg cells. For example, in vivo activation and expansion of Treg cells can be measured using any method known in the art, e.g., by flow cytometry. Preferred agonist antibody cytokine engrafted proteins can be therapeutically useful in preventing, reducing, inhibiting or eliminating immune related disorders, for example: Type 1 diabetes, System Lupus Erythematosus, Vitiligo, chronic graft versus host disease (cGvHD), prophylactic acute graft versus host disease (pGvHD), HIV-induced vasculitis, Alopecia areata, Systemic sclerosis morphoea and primary anti-phospholipid syndrome. The efficacy of the agonist antibody cytokine engrafted proteins in Type 1 diabetes and SLE can be determined by administering a therapeutically effective amount of the antibody cytokine engrafted protein to a subject and comparing the subject before and after administration of the antibody cytokine engrafted protein. Efficacy of the agonist antibody cytokine engrafted proteins in therapy for Type 1 diabetes and SLE also can be determined by administering a therapeutically effective amount of an antibody cytokine engrafted protein to a test subject and comparing the test subject to a control subject who has not been administered the antibody and/or comparison to a subject similarly treated with Proleukin®.

Polynucleotides Encoding Agonist Antibody Cytokine Engrafted Proteins

In another aspect, isolated nucleic acids encoding heavy and light chain proteins of the antibody cytokine engrafted proteins are provided. Antibody cytokine engrafted proteins can be produced by any means known in the art, including but not limited to, recombinant expression, chemical synthesis, and enzymatic digestion of antibody tetramers. Recombinant expression can be from any appropriate host cells known in the art, for example, mammalian host cells, bacterial host cells, yeast host cells, insect host cells, etc.

Provided herein are polynucleotides that encode the variable regions exemplified in any one of SEQ ID NO:21, SEQ ID NO: 34, SEQ ID NO:47, SEQ ID NO: 60, SEQ ID NO:73, SEQ ID NO:86, SEQ ID NO:99, and SEQ ID NO:112.

The disclosure thus provides polynucleotides encoding the light and/or heavy chain polypeptides of the antibody cytokine engrafted proteins described herein, e.g., polynucleotides encoding light or heavy chain variable regions or segments comprising the complementary determining regions as described herein. In some embodiments, the polynucleotide encoding the heavy chain variable regions comprises a sequence having at least 85%, 89%, 90%, 91%, 92%, 93%, 94%, 95%, 96%, 97%, 98%, 99%, or 100% nucleic acid sequence identity with a polynucleotide selected from the group consisting of SEQ ID NO: 21, SEQ ID NO: 47, SEQ ID NO:73, and SEQ ID NO:99. In some embodiments, the polynucleotide encoding the light chain variable regions comprises a sequence having at least 85%, 89%, 90%, 91%, 92%, 93%, 94%, 95%, 96%, 97%, 98%, 99%, or 100% nucleic acid sequence identity with a polynucleotide selected from the group consisting of SEQ ID NO: 34, SEQ ID NO: 60, SEQ ID NO:86, and SEQ ID NO: 112.

In some embodiments, the polynucleotide encoding the heavy chain has at least 85%, 89%, 90%, 91%, 92%, 93%, 94%, 95%, 96%, 97%, 98%, 99%, or 100% nucleic acid sequence identity with a polynucleotide of SEQ ID NO:23. In some embodiments, the polynucleotide encoding the light chain has at least 85%, 89%, 90%, 91%, 92%, 93%, 94%, 95%, 96%, 97%, 98%, 99%, or 100% nucleic acid sequence identity with a polynucleotide of SEQ ID NO:36.

In some embodiments, the polynucleotide encoding the heavy chain has at least 85%, 89%, 90%, 91%, 92%, 93%, 94%, 95%, 96%, 97%, 98%, 99%, or 100% nucleic acid sequence identity with a polynucleotide of SEQ ID NO:49. In some embodiments, the polynucleotide encoding the light chain has at least 85%, 89%, 90%, 91%, 92%, 93%, 94%, 95%, 96%, 97%, 98%, 99%, or 100% nucleic acid sequence identity with a polynucleotide of SEQ ID NO:62.

In some embodiments, the polynucleotide encoding the heavy chain has at least 85%, 89%, 90%, 91%, 92%, 93%, 94%, 95%, 96%, 97%, 98%, 99%, or 100% nucleic acid sequence identity with a polynucleotide of SEQ ID NO:75. In some embodiments, the polynucleotide encoding the light chain has at least 85%, 89%, 90%, 91%, 92%, 93%, 94%, 95%, 96%, 97%, 98%, 99%, or 100% nucleic acid sequence identity with a polynucleotide of SEQ ID NO:88.

In some embodiments, the polynucleotide encoding the heavy chain has at least 85%, 89%, 90%, 91%, 92%, 93%, 94%, 95%, 96%, 97%, 98%, 99%, or 100% nucleic acid sequence identity with a polynucleotide of SEQ ID NO:101. In some embodiments, the polynucleotide encoding the light chain has at least 85%, 89%, 90%, 91%, 92%, 93%, 94%, 95%, 96%, 97%, 98%, 99%, or 100% nucleic acid sequence identity with a polynucleotide of SEQ ID NO:114.

Polynucleotides can encode only the variable region sequence of an antibody cytokine engrafted protein. They can also encode both a variable region and a constant region of the antibody cytokine engrafted protein. Some of the polynucleotide sequences encode a polypeptide that comprises variable regions of both the heavy chain and the light chain of one of the antibody cytokine engrafted proteins. Some other polynucleotides encode two polypeptide segments that respectively are substantially identical to the variable regions of the heavy chain and the light chain of one of the antibody protein engrafteds.

In certain embodiments polynucleotides or nucleic acids comprise DNA. In other embodiments polynucleotides or nucleic acids comprise RNA, which may be single stranded or double stranded.

In some embodiments a recombinant host cell comprising the nucleic acids encoding one or more immunoglobulin protein chain of an antibody cytokine engrafted protein, and optionally, secretion signals is provided. In certain embodiments a recombinant host cell comprises a vector encoding one immunoglobulin protein chain and secretion signals. In other certain embodiments a recombinant host cell comprises one or more vectors encoding two immunoglobulin protein chains of the antibody cytokine engrafted protein and secretion signals. In some embodiments a recombinant host cell comprises a single vector encoding two immunoglobulin protein chains of the antibody cytokine engrafted protein and secretion signals. In some embodiments a recombinant host cell comprises two vectors, one encoding a heavy chain immunoglobulin protein chain, and another encoding a light chain immunoglobulin protein chain of the antibody cytokine engrafted protein, with each including secretion signals. A recombinant host cell may be a prokaryotic or eukaryotic cell. In some embodiments the host cell is a eukaryotic cell line. In some embodiments the host cell is a mammalian cell line. In some embodiments the host cell is a CHO cell. In some embodiments, the host cell line is a CHO cell line for antibody production.

Additionally provided are methods for producing the antibody cytokine engrafted proteins. In some embodiments the method comprises the steps of (i) culturing a host cell comprising one or more vectors encoding immunoglobulin protein chains of an antibody cytokine engrafted protein under conditions suitable for expression, formation, and secretion of the antibody cytokine engrafted protein and (ii) recovering the antibody cytokine engrafted protein.

The polynucleotide sequences can be produced by de novo solid-phase DNA synthesis or by PCR mutagenesis of an existing sequence (e.g., sequences as described herein) encoding a polypeptide chain of an antibody cytokine engrafted protein. Direct chemical synthesis of nucleic acids can be accomplished by methods known in the art, such as the phosphotriester method of Narang et al., Meth. Enzymol. 68:90, 1979; the phosphodiester method of Brown et al., Meth. Enzymol. 68:109, 1979; the diethylphosphoramidite method of Beaucage et al., Tetra. Lett., 22:1859, 1981; and the solid support method of U.S. Pat. No. 4,458,066. Introducing mutations to a polynucleotide sequence by PCR can be performed as described in, e.g., PCR Technology: Principles and Applications for DNA Amplification, H.A. Erlich (Ed.), Freeman Press, NY, N.Y., 1992; PCR Protocols: A Guide to Methods and Applications, Innis et al. (Ed.), Academic Press, San Diego, Calif., 1990; Manila et al., Nucleic Acids Res. 19:967, 1991; and Eckert et al., PCR Methods and Applications 1:17, 1991.

Also provided are expression vectors and host cells for producing the antibody cytokine engrafted proteins described above. Various expression vectors can be employed to express polynucleotides encoding the immunoglobulin polypeptide chains, or fragments, of the antibody cytokine engrafted proteins. Both viral-based and nonviral expression vectors can be used to produce the immunoglobulin proteins in a mammalian host cell. Nonviral vectors and systems include plasmids, episomal vectors, typically with an expression cassette for expressing a protein or RNA, and human artificial chromosomes (see, e.g., Harrington et al., Nat Genet 15:345, 1997). For example, nonviral vectors useful for expression of the antibody cytokine engrafted protein polynucleotides and polypeptides in mammalian (e.g., human) cells include pThioHis A, B & C, pcDNA3.1/His, pEBVHis A, B & C (Invitrogen, San Diego, Calif.), MPSV vectors, and numerous other vectors known in the art for expressing other proteins. Useful viral vectors include vectors based on retroviruses, adenoviruses, adeno-associated viruses, herpes viruses, vectors based on SV40, papilloma virus, HBP Epstein Barr virus, vaccinia virus vectors and Semliki Forest virus (SFV). See, Brent et al., supra; Smith, Annu. Rev. Microbiol. 49:807, 1995; and Rosenfeld et al., Cell 68:143, 1992.

The choice of expression vector depends on the intended host cells in which the vector is to be expressed. Typically, the expression vectors contain a promoter and other regulatory sequences (e.g., enhancers) that are operably linked to the polynucleotides encoding an immunoglobulin protein of the antibody cytokine engrafted protein. In some embodiments, an inducible promoter is employed to prevent expression of inserted sequences except under inducing conditions. Inducible promoters include, e.g., arabinose, lacZ, metallothionein promoter or a heat shock promoter. Cultures of transformed organisms can be expanded under noninducing conditions without biasing the population for coding sequences whose expression products are better tolerated by the host cells. In addition to promoters, other regulatory elements may also be required or desired for efficient expression of an immunoglobulin chain or fragment of the antibody cytokine engrafted proteins. These elements typically include an ATG initiation codon and adjacent ribosome binding site or other sequences. In addition, the efficiency of expression may be enhanced by the inclusion of enhancers appropriate to the cell system in use (see, e.g., Scharf et al., Results Probl. Cell Differ. 20:125, 1994; and Bittner et al., Meth. Enzymol., 153:516, 1987). For example, the SV40 enhancer or CMV enhancer can be used to increase expression in mammalian host cells.

Expression vectors can also provide a secretion signal sequence position to form an antibody cytokine engrafted protein that exported out of the cell and into the culture medium. In certain aspects, the inserted immunoglobulin sequences of the antibody cytokine engrafted proteins are linked to a signal sequences before inclusion in the vector. Vectors to be used to receive sequences encoding immunoglobulin light and heavy chain variable domains sometimes also encode constant regions or parts thereof. Such vectors allow expression of the variable regions as engrafted proteins with the constant regions thereby leading to production of intact antibody cytokine engrafted proteins or fragments thereof. Typically, such constant regions are human.

Host cells for harboring and expressing the antibody cytokine engrafted protein chains can be either prokaryotic or eukaryotic. *E. coli* is one prokaryotic host useful for cloning and expressing the polynucleotides of the present disclosure. Other microbial hosts suitable for use include bacilli, such as Bacillus subtilis, and other enterobacteriaceae, such as Salmonella, Serratia, and various Pseudomonas species. In these prokaryotic hosts, one can also make expression vectors, which typically contain expression control sequences compatible with the host cell (e.g., an origin of replication). In addition, any number of a variety of well-known promoters will be present, such as the lactose promoter system, a tryptophan (trp) promoter system, a beta-lactamase promoter system, or a promoter system from phage lambda. The promoters typically control expression, optionally with an operator sequence, and have ribosome binding site sequences and the like, for initiating and completing transcription and translation. Other microbes, such as yeast, can also be employed to express antibody cytokine engrafted protein polypeptides. Insect cells in combination with baculovirus vectors can also be used.

In some preferred embodiments, mammalian host cells are used to express and produce the antibody cytokine engrafted protein polypeptides. For example, they can be either a mammalian cell line harboring an exogenous expression vector. These include any normal mortal or normal or abnormal immortal animal or human cell. For example, a number of suitable host cell lines capable of secreting intact immunoglobulins have been developed, including the CHO cell lines, various Cos cell lines, HeLa cells, myeloma cell lines, transformed B-cells and hybridomas. The use of mammalian tissue cell culture to express polypeptides is discussed generally in, e.g., Winnacker, From Genes to Clones, VCH Publishers, N.Y., N.Y., 1987. Expression vectors for mammalian host cells can include expression control sequences, such as an origin of replication, a promoter, and an enhancer (see, e.g., Queen et al., Immunol. Rev. 89:49-68, 1986), and necessary processing information sites, such as ribosome binding sites, RNA splice sites, polyadenylation sites, and transcriptional terminator sequences. These expression vectors usually contain promoters derived from mammalian genes or from mammalian viruses. Suitable promoters may be constitutive, cell type-specific, stage-specific, and/or modulatable or regulatable. Useful promoters include, but are not limited to, the metallothionein promoter, the constitutive adenovirus major late promoter, the dexamethasone-inducible MMTV promoter, the SV40 promoter, the MRP polIII promoter, the constitutive MPSV promoter, the tetracycline-inducible CMV promoter (such as the human immediate-early CMV promoter), the constitutive CMV promoter, and promoter-enhancer combinations known in the art.

Methods for introducing expression vectors containing the polynucleotide sequences of interest vary depending on the type of cellular host. For example, calcium chloride transfection is commonly utilized for prokaryotic cells, whereas calcium phosphate treatment or electroporation may be used for other cellular hosts (see generally Sambrook et al., supra). Other methods include, e.g., electroporation, calcium phosphate treatment, liposome-mediated transformation, injection and microinjection, ballistic methods, virosomes, immunoliposomes, polycation:nucleic acid conjugates, naked DNA, artificial virions, engrafted to the herpes virus structural protein VP22 (Elliot and O'Hare, Cell 88:223, 1997), agent-enhanced uptake of DNA, and ex vivo transduction. For long-term, high-yield production of recombinant proteins, stable expression will often be desired. For example, cell lines which stably express antibody cytokine engrafted protein immunoglobulin chains can be prepared using expression vectors which contain viral origins of replication or endogenous expression elements and a selectable marker gene. Following introduction of the vector, cells can be allowed to grow for 1-2 days in an enriched media before they are switched to selective media. The purpose of the selectable marker is to confer resistance to selection, and its presence allows growth of cells which successfully express the introduced sequences in selective media. Resistant, stably transfected cells can be proliferated using tissue culture techniques appropriate to the cell type.

Compositions Comprising Antibody Cytokine Engrafted Proteins

Provided are pharmaceutical compositions comprising an antibody cytokine engrafted protein formulated together with a pharmaceutically acceptable carrier. Optionally, pharmaceutical compositions additionally contain other therapeutic agents that are suitable for treating or preventing a given disorder. Pharmaceutically acceptable carriers enhance or stabilize the composition, or facilitate preparation of the composition. Pharmaceutically acceptable carriers include solvents, dispersion media, coatings, antibacterial and antifungal agents, isotonic and absorption delaying agents, and the like that are physiologically compatible.

A pharmaceutical composition can be administered by a variety of methods known in the art. Route and/or mode of administration vary depending upon the desired results. It is preferred that administration be by parenteral administration (e.g., selected from any of intravenous, intramuscular, intraperitoneal, intrathecal, intraarterial, or subcutaneous), or administered proximal to the site of the target. A pharmaceutically acceptable carrier is suitable for administration by any one or more of intravenous, intramuscular, intraperitoneal, intrathecal, intraarterial, subcutaneous, intranasal, inhalational, spinal or epidermal administration (e.g., by injection or inengrafted). Depending on the route of administration, active compound, e.g., antibody cytokine engrafted protein, can be coated in a material to protect the compound from the action of acids and other natural conditions that may inactivate the compound. In some embodiments the pharmaceutical composition is formulated for intravenous administration. In some embodiments the pharmaceutical composition is formulation for subcutaneous administration.

An antibody cytokine engrafted protein, alone or in combination with other suitable components, can be made into aerosol formulations (i.e., they can be "nebulized") to be administered via inhalation. Aerosol formulations can be placed into pressurized acceptable propellants, such as dichlorodifluoromethane, propane, nitrogen, and the like.

In some embodiments, a pharmaceutical composition is sterile and fluid. Proper fluidity can be maintained, for example, by use of coating such as lecithin, by maintenance of required particle size in the case of dispersion and by use of surfactants. In many cases, it is preferable to include isotonic agents, for example, sugars, polyalcohols such as mannitol or sorbitol, and sodium chloride in the composition. Long-term absorption of the injectable compositions can be brought about by including in the composition an agent which delays absorption, for example, aluminum monostearate or gelatin. In certain embodiments compositions can be prepared for storage in a lyophilized form using appropriate excipients (e.g., sucrose).

Pharmaceutical compositions can be prepared in accordance with methods well known and routinely practiced in the art. Pharmaceutically acceptable carriers are determined in part by the particular composition being administered, as well as by the particular method used to administer the composition. Accordingly, there is a wide variety of suitable formulations of pharmaceutical compositions. Applicable methods for formulating an antibody cytokine engrafted protein and determining appropriate dosing and scheduling can be found, for example, in *Remington: The Science and Practice of Pharmacy*, 21$^{st}$ Ed., University of the Sciences in Philadelphia, Eds., Lippincott Williams & Wilkins (2005); and in *Martindale: The Complete Drug Reference,* Sweetman, 2005, London: Pharmaceutical Press., and in Martindale, *Martindale: The Extra Pharmacopoeia,* 31st Edition., 1996, Amer Pharmaceutical Assn, and Sustained and Controlled Release Drug Delivery Systems, J. R. Robinson, ed., Marcel Dekker, Inc., New York, 1978, each of which are hereby incorporated herein by reference. Pharmaceutical compositions are preferably manufactured under GMP conditions. Typically, a therapeutically effective dose or efficacious dose of an antibody cytokine engrafted protein is employed in the pharmaceutical compositions. An antibody cytokine engrafted protein is formulated into pharmaceutically acceptable dosage form by conventional methods known to those of skill in the art. Dosage regimens are adjusted to provide the desired response (e.g., a therapeutic response). In determining a therapeutically or prophylactically effective dose, a low dose can be administered and then incrementally increased until a desired response is achieved with minimal or no undesired side effects. For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the subjects to be treated; each unit contains a predetermined quantity of active compound calculated to produce the desired therapeutic effect in association with the required pharmaceutical carrier.

Actual dosage levels of active ingredients in the pharmaceutical compositions of the present disclosure can be varied so as to obtain an amount of the active ingredient which is effective to achieve the desired therapeutic response for a particular patient, composition, and mode of administration, without being toxic to the patient. The selected dosage level depends upon a variety of pharmacokinetic factors including the activity of the particular compositions employed, or the ester, salt or amide thereof, the route of administration, the time of administration, the rate of excretion of the particular compound being employed, the duration of the treatment, other drugs, compounds and/or materials used in combination with the particular compositions employed, the age, sex, weight, condition, general health and prior medical history of the patient being treated, and like factors.

Co-Formulation with Second Agent

In some embodiments, the pharmacological compositions comprise a mixture of an antibody cytokine engrafted protein and one or more additional pharmacological agent(s). Exemplary second agents for inclusion in mixtures with the present antibody cytokine engrafted protein include without limitation anti-inflammatory agents, immunomodulatory agents, aminosalicylates, and antibiotics. Appropriate selection may depend on preferred formulation, dosage and/or delivery method.

In some embodiments an antibody cytokine engrafted protein is co-formulated (i.e., provided as a mixture or prepared in a mixture) with an anti-inflammatory agent. In particular embodiments corticosteroid anti-inflammatory agents may be used in conjunction with the antibody cytokine engrafted protein. Corticosteroids for use may be selected from any of methylprednisolone, hydrocortisone, prednisone, budenisonide, mesalamine, and dexamethasone. Appropriate selection will depend on formulation and delivery preferences.

In some embodiments, an antibody cytokine engrafted protein is co-formulated with an immunomodulatory agent. In particular embodiments immunomodulator selected from any of 6-mercaptopurine, azathioprine, cyclosporine A, tacrolimus, and methotrexate. In particular embodiments an immunomodulator is selected from an anti-TNF agent (e.g., infliximab, adalimumab, certolizumab, golimumab), natalizumab, and vedolizumab.

In some embodiments an antibody cytokine engrafted protein is co-formulated with an aminosalicylate agent. In particular embodiments an aminosalicylate is selected from sulfasalazine, mesalamine, balsalazide, olsalazine or other derivatives of 5-aminosalicylic acid.

In some embodiments an antibody cytokine engrafted protein is co-formulated with an antibacterial agent. Exemplary antibacterial agents include without limitation sulfonamides (e.g., sulfanilamide, sulfadiazine, sulfamethoxazole, sulfisoxazole, sulfacetamide), trimethoprim, quinolones (e.g., nalidixic acid, cinoxacin, norfloxacin, ciprofloxacin, ofloxacin, sparfloxacin, fleroxacin, perloxacin, levofloxacin, garenoxacin and gemifloxacin), methenamine, nitrofurantoin, penicillins (e.g., penicillin G, penicillin V, methicilin oxacillin, cloxacillin, dicloxacillin, nafcilin, ampicillin, amoxicillin, carbenicillin, ticarcillin, mezlocillin, and piperacillin), cephalosporins (e.g., cefazolin, cephalexin, cefadroxil, cefoxitin, cefaclor, cefprozil, cefuroxime, cefuroxime acetil, loracarbef, cefotetan, ceforanide, cefotaxime, cefpodoxime proxetil, cefibuten, cefdinir, cefditoren pivorxil, ceftizoxime, ceftriaxone, cefoperazone, ceftazidime, and cefepine), carbapenems (e.g., imipenem, aztreonam), and aminoglycosides (e.g., neomycin, kanamycin, streptomycin, gentamicin, toramycin, netilmicin, and amikacin).

Articles of Manufacture/Kits

In some aspects an antibody cytokine engrafted protein is provided in an article of manufacture (i.e., a kit). A provided antibody cytokine engrafted protein is generally in a vial or a container. Thus, an article of manufacture comprises a container and a label or package insert, on or associated with the container. Suitable containers include, for example, a bottle, vial, syringe, solution bag, etc. As appropriate, the antibody cytokine engrafted protein can be in liquid or dried (e.g., lyophilized) form. The container holds a composition which, by itself or combined with another composition, is effective for preparing a composition for treating, preventing and/or ameliorating an immune related disorder. The label or package insert indicates the composition is used for treating, preventing and/or ameliorating an immune related disorder. Articles of manufacture (kits) comprising an antibody cytokine engrafted protein, as described herein, optionally contain one or more additional agent. In some embodiments, an article of manufacture (kit) contains antibody cytokine engrafted protein and a pharmaceutically acceptable diluent. In some embodiments an antibody cytokine engrafted protein is provided in an article of manufacture (kit) with one or more additional active agent in the same formulation (e.g., as mixtures). In some embodiments an antibody cytokine engrafted protein is provided in an article of manufacture (kit) with a second or third agent in separate formulations (e.g., in separate containers). In certain embodiments an article of manufacture (kit) contains aliquots of the antibody cytokine engrafted protein wherein the aliquot provides for one or more doses. In some embodiments aliquots for multiple administrations are provided, wherein doses are uniform or varied. In particular embodiments varied dosing regimens are escalating or decreasing, as appropriate. In some embodiments dosages of an antibody cytokine engrafted protein and a second agent are independently uniform or independently varying. In certain embodiments, an article of manufacture (kit) comprises an additional agent selected from any of an anti-inflammatory agent, immunomodulatory agent, aminosalicylate, and antibiotic. Selection of one or more additional agent will depend on the dosage, delivery, and disease condition to be treated.

Methods of Treatment and Use of Compositions for Treatment of Immune Related Disorders Conditions Subject to Treatment or Prevention Antibody cytokine engrafted proteins find use in treatment, amelioration or prophylaxis of immune related disorders. In one aspect, the disclosure provides methods of treatment of immune related disorders in an individual in need thereof, comprising administering to the individual a therapeutically effective amount of an antibody cytokine engrafted protein, as described herein. The disclosure also provides in one aspect an antibody cytokine engrafted protein for use as a therapeutic agent. In some embodiment an antibody cytokine engrafted protein is provided for use as a therapeutic agent in the treatment or prophylaxis of an immune related disorder in an individual. In some embodiments use of an antibody cytokine engrafted protein is provided for manufacture of a medicament for treatment of immune related disorder in an individual in need thereof. In a further aspect, the disclosure provides a composition comprising such an antibody cytokine engrafted protein for use in treating or ameliorating immune related disorder in an individual in need thereof.

Conditions subject to treatment include immune related disorders. For therapeutic purposes, an individual may have an immune related disorder. For preventative or prophylactic purposes, an individual can be in remission from an active state of immune related disorder or may anticipate future onset. In some embodiments, the patient has an immune related disorder, is suspected of having an immune related disorder, or is in remission from an immune related disorder. Immune related disorders subject to treatment with the an antibody cytokine engrafted protein derive benefit from activation of IL2 receptor signaling on Treg cells. Immune related disorders subject to treatment include without limitation: Type 1 diabetes, System Lupus Erythematosus, Vitiligo, chronic graft versus host disease (cGvHD), prophylactic acute graft versus host disease (pGvHD), HIV-induced vasculitis, Alopecia areata, Systemic sclerosis morphoea and primary anti-phospholipid syndrome.

Administration of Antibody Cytokine Engrafted Proteins

A physician or veterinarian can start doses of an antibody cytokine engrafted protein employed in the pharmaceutical composition at levels lower than that required to achieve the desired therapeutic effect and gradually increase the dosage until the desired effect is achieved. In general, effective doses of the compositions vary depending upon many different factors, including the specific disease or condition to be treated, means of administration, target site, physiological state of the patient, whether a patient is human or an animal, other medications administered, and whether treatment is prophylactic or therapeutic. Treatment dosages typically require titration to optimize safety and efficacy. For administration with an antibody cytokine engrafted protein, dosage ranges from about 0.0001 to 100 mg/kg, and more usually 0.01 to 5 mg/kg, of the host body weight. For example dosages can be 1 mg/kg body weight or 10 mg/kg body weight or within the range of 1-10 mg/kg. Dosing can be daily, weekly, bi-weekly, monthly, or more or less often, as needed or desired. An exemplary treatment regime entails administration once weekly, once per every two weeks or once a month or once every 3 to 6 months.

The antibody cytokine engrafted protein can be administered in single or divided doses. An antibody cytokine engrafted protein is usually administered on multiple occasions. Intervals between single dosages can be weekly, bi-weekly, monthly or yearly, as needed or desired. Intervals can also be irregular as indicated by measuring blood levels of antibody cytokine engrafted protein in the patient. In some methods, dosage is adjusted to achieve a plasma antibody cytokine engrafted protein concentration of 1-1000 μg/ml and in some methods 25-300 μg/ml. Alternatively, antibody cytokine engrafted protein can be administered as a sustained release formulation, in which case less frequent administration is required. Dosage and frequency vary depending on the half-life of the antibody cytokine engrafted protein in the patient. In general, antibody engrafted proteins show longer half-life than that of native IL2 or recombinant cytokines such as Proleukin®. Dosage and frequency of administration can vary depending on whether treatment is prophylactic or therapeutic. In general for prophylactic applications, a relatively low dosage is administered at relatively infrequent intervals over a long period of time. In general for therapeutic applications, a relatively high dosage in relatively short intervals is sometimes required until progression of the disease is reduced or terminated, and preferably until the patient shows partial or complete amelioration of symptoms of disease. Thereafter, a patient may be administered a prophylactic regime.

Co-Administration with a Second Agent

The term "combination therapy" refers to the administration of two or more therapeutic agents to treat a therapeutic condition or disorder described in the present disclosure. Such administration encompasses co-administration of these therapeutic agents in a substantially simultaneous manner, such as in a single capsule having a fixed ratio of active ingredients. Alternatively, such administration encompasses co-administration in multiple, or in separate containers (e.g., capsules, powders, and liquids) for each active ingredient. Powders and/or liquids may be reconstituted or diluted to a desired dose prior to administration. In addition, such administration also encompasses use of each type of therapeutic agent in a sequential manner, either at approximately the same time or at different times. In either case, the treatment regimen will provide beneficial effects of the drug combination in treating the conditions or disorders described herein.

In some embodiments, an antibody cytokine engrafted protein is co-administered with one or more additional pharmacological agent(s). In some embodiments, an antibody cytokine engrafted protein and an additional one or more agent(s) are administered as a mixture. In some embodiments, an antibody cytokine engrafted protein an additional one or more agent(s) are administered as separate formulations. In certain embodiments where separate formulations are utilized, administration is concurrent. In certain embodiments where separate formulations are utilized, administration is sequential. In certain embodiments where separate formulations are utilized, administration is via the same route. In certain embodiments where separate formulations are utilized, administration is via different routes. Exemplary additional agents for co-administration with an antibody cytokine engrafted protein include without limitation anti-inflammatory agents, immunomodulatory agents, aminosalicylates, and antibiotics. Appropriate selection may depend on preferred formulation, dosage and/or delivery method. The antibody cytokine engrafted proteins also find use in combination therapies with additional established procedures for treating immune related disorder conditions, e.g., surgery.

In some embodiments an antibody cytokine engrafted protein is co-administered with an anti-inflammatory agent. In particular embodiments corticosteroid anti-inflammatory agents may be used in conjunction with the antibody cytokine engrafted protein. Corticosteroids for use may be selected from any of methylprednisolone, hydrocortisone, prednisone, budenisonide, mesalamine, and dexamethasone. Appropriate selection will depend on formulation and delivery preferences.

In some embodiments, an antibody cytokine engrafted protein is co-administered with an immunomodulatory agent. In particular embodiments immunomodulator selected from any of 6-mercaptopurine, azathioprine, cyclosporine A, tacrolimus, and methotrexate. In another embodiment an immunomodulator is selected from an anti-TNF agent (e.g., infliximab, adalimumab, certolizumab, golimumab), natalizumab, and vedolizumab.

In some embodiments an antibody cytokine engrafted protein is co-administered with an aminosalicylate agent. In particular embodiments an aminosalicylate is selected from sulfasalazine, mesalamine, balsalazide, olsalazine or other derivatives of 5-aminosalicylic acid.

In some embodiments an antibody cytokine engrafted protein is co-administered with an antibacterial agent. Exemplary antibacterial agents include without limitation sulfonamides (e.g., sulfanilamide, sulfadiazine, sulfamethoxazole, sulfisoxazole, sulfacetamide), trimethoprim, quinolones (e.g., nalidixic acid, cinoxacin, norfloxacin, ciprofloxacin, ofloxacin, sparfloxacin, fleroxacin, perloxacin, levofloxacin, garenoxacin and gemifloxacin), methenamine, nitrofurantoin, penicillins (e.g., penicillin G, penicillin V, methicilin oxacillin, cloxacillin, dicloxacillin, nafcilin, ampicillin, amoxicillin, carbenicillin, ticarcillin, mezlocillin, and piperacillin), cephalosporins (e.g., cefazolin, cephalexin, cefadroxil, cefoxitin, cefaclor, cefprozil, cefuroxime, cefuroxime acetil, loracarbef, cefotetan, ceforanide, cefotaxime, cefpodoxime proxetil, cefibuten, cefdinir, cefditoren pivorxil, ceftizoxime, ceftriaxone, cefoperazone, ceftazidime, and cefepine), carbapenems (e.g., imipenem, aztreonam), and aminoglycosides (e.g., neomycin, kanamycin, streptomycin, gentamicin, toramycin, netilmicin, and amikacin).

In some embodiments an antibody cytokine engrafted protein is co-administered with the standard of care. For example, in the treatment of Type 1 Diabetes, the standard of care is the administration of insulin or insulin therapy. The antibody cytokine engrafted proteins as disclosed herein would still work well on promoting immune tolerance as insulin primarily restores normal sugar levels.

EXAMPLES

Example 1

Creation of IL2 Antibody Cytokine Engrafted Proteins

Antibody cytokine engrafted proteins were generated by engineering an IL2 sequence into CDR regions of various immunoglobulin scaffolds, then both heavy and light chain immunoglobulin chains were used to generate final antibody cytokine proteins. Antibody cytokine engrafted proteins confer the preferred therapeutic properties of IL2; however, antibody cytokine engrafted proteins have reduced undesired effects, such as increased NK cell activity, as compared with rhIL2.

To create antibody cytokine engrafted proteins, IL2 sequences containing muteins (SEQ ID NO:4 or 6) were inserted into CDR loops of an immunoglobulin chain scaffold. Antibody cytokine engrafted proteins were prepared using a variety of known immunoglobulin sequences which have been utilized in clinical settings as well as germline antibody sequences. Sequences of IL2 in an exemplary scaffold, referred to as GFTX3b, are depicted in TABLE 2. Insertion points were selected to be the mid-point of the loop based on available structural or homology model data. Antibody cytokine engrafted proteins were produced using standard molecular biology methodology utilizing recombinant DNA encoding the relevant sequences.

The selection of which CDR is chosen for cytokine engraftment is chosen on the parameters of: the required biology, biophysical properties and a favorable development profile. Modeling software was only partially useful in predicting which CDR and which location within the CDR will provide the desired parameters, so therefore all six possible antibody cytokine grafts are made and then evaluated in biological assays. If the required biological activity is achieved, then the biophysical properties such as structural resolution as to how the antibody cytokine engrafted molecule interacts with the respective cytokine receptor are resolved.

For the antibody IL2 engrafted molecules, the structure of the antibody candidate considered for cytokine engrafting was initially solved. From this structure, it was noted that the paratope, the portion of the antibody that interacts with the epitope, was at the extreme N-terminus of the antibody "arm" and that a cytokine engrafted into this location would present the cytokine to its respective receptor. Because of the grafting technology, each antibody IL2 engrafted protein is constrained by a CDR loop of different length, sequence and structural environments. As such, IL2 was engrafted into all six CDRs, corresponding to LCDR-1, LCDR-2, LCDR-3 and HCDR-1, HCDR-2 and HCDR-3. FIG. 1 shows the different exemplary versions of the IL2 antibody cytokine grafts that were made which include various point mutations and shifting the IL2 insertion point to either the N or C portion of the CDR loop (nH1, cH1, nH2, cH2). From the Table in FIG. 1, it is apparent that the antibody cytokine engrafted proteins all differ in their activities, including that IL2 engrafted into the light chain of CDR2 (IgG.IL2.L2) did not express. It was also observed that IL2 antibody cytokine grafts with altered Fc function (e.g. Fc silent) had a better profile.

HCDR-1 was chosen because it had the best combination of properties (biophysical and biological) and the IL2 point mutations that were included enhanced the desired biological properties. For the selection of the insertion point, the structural center of the CDR loop was chosen as this would provide the most space on either side (of linear size 3.8Å x the number of residues) and without being bound by any one theory, this provided a stable molecule by allowing the IL2 to more readily fold independently. As the structure of the grafting scaffold GFTX3b was already known, so the structural center of each CDR was also known. This coincided with the center of the CDR loop sequence as defined using the Chothia numbering format. As mentioned previously, the insertion point of the IL-2 grafts were shifted away from the center and toward either the N or C terminal portion of the CDR loop. However, shifting IL2 within the CDR loop did not make a significant difference in biological activity.

In summary, the insertion point in each CDR was chosen on a structural basis, with the hypothesis that grafting into the CDR would provide some level of steric hindrance to individual subunits of the IL2 receptor. The final selection of which CDR graft was best for a particular cytokine was based on desired biology and biophysical properties. The nature of the cytokine receptor, the cytokine/receptor interactions and the mechanism of signaling also played a role and this was done by comparing each individual antibody cytokine molecule for their respective properties.

TABLE 1

| | | |
|---|---|---|
| SEQ ID NO: 1 | wild type IL2 DNA | AGTTCCCTATCACTCTCTTTAATCACTACTCACAGTAACC<br>TCAACTCCTGCCACAATGTACAGGATGCAACTCCTGTCTT<br>GCATTGCACTAAGTCTTGCACTTGTCACAAACAGTGCACC<br>TACTTCAAGTTCTACAAAGAAAACACAGCTACAACTGGAG<br>CATTTACTGCTGGATTTACAGATGATTTTGAATGGAATTA<br>ATAATTACAAGAATCCCAAACTCACCAGGATGCTCACATT<br>TAAGTTTTACATGCCCAAGAAGGCCACAGAACTGAAACAT<br>CTTCAGTGTCTAGAAGAAGAACTCAAACCTCTGGAGGAAG<br>TGCTAAATTTAGCTCAAAGCAAAAACTTTCACTTAAGACC<br>CAGGGACTTAATCAGCAATATCAACGTAATAGTTCTGGAA<br>CTAAAGGGATCTGAAACAACATTCATGTGTGAATATGCTG<br>ATGAGACAGCAACCATTGTAGAATTTCTGAACAGATGGAT<br>TACCTTTTGTCAAAGCATCATCTCAACACTGACTTGATAA |

TABLE 1-continued

| | | |
|---|---|---|
| | | TTAAGTGCTTCCCACTTAAAACATATCAGGCCTTCTATTT<br>ATTTAAATATTTAAATTTTATATTTATTGTTGAATGTATG<br>GTTTGCTACCTATTGTAACTATTATTCTTAATCTTAAAAC<br>TATAAATATGGATCTTTTATGATTCTTTTTGTAAGCCCTA<br>GGGGCTCTAAAATGGTTTCACTTATTTATCCCAAAATATT<br>TATTATTATGTTGAATGTTAAATATAGTATCTATGTAGAT<br>TGGTTAGTAAAACTATTTAATAAATTTGATAAATATAAAA<br>AAAAAAAAAAAAAAAAAAAAA |
| SEQ ID NO: 2 | Wild type IL2 protein | MYRMQLLSCIALSLALVTNSAPTSSSTKKTQLQLEHLLLD<br>LQMILNGINNYKNPKLTRMLTFKFYMPKKATELKHLQCLE<br>EELKPLEEVLNLAQSKNFHLRPRDLISNINVIVLELKGSE<br>TTFMCEYADETATIVEFLNRWITFCQSIISTLT |
| SEQ ID NO: 3 | IL2 mutein DNA | GCCCCTACCTCCTCCAGCACCAAGAAAACCCAGCTGCAGC<br>TCGAACATCTGCTGCTGGCCCTGCAGATGATCCTGAACGG<br>CATCAACAACTACAAGAACCCCAAGCTGACCCGGATGCTG<br>ACCTTCAAGTTCTACATGCCCAAGAAGGCCACCGAGCTGA<br>AACATCTGCAGTGCCTGGAAGAGGAACTGAAGCCCCTGGA<br>AGAAGTGCTGAACCTGGCCCAGTCCAAGAACTTCCACCTG<br>AGGCCTCGGGACCTGATCTCCAACATCAACGTGATCGTGC<br>TGGAACTGAAGGGCTCCGAGACAACCTTCATGTGCGAGTA<br>CGCCGACGAGACAGCCACCATCGTGGAATTTCTGAACCGG<br>TGGATCACCTTCTGCCAGTCCATCATCTCCACCCTGACC |
| SEQ ID NO: 4 | IL2 mutein protein, the mutein amino acid is bolded and underlined | APTSSSTKKTQLQLEHLLLALQMILNGINNYKNPKLTRML<br>TFKFYMPKKATELKHLQCLEEELKPLEEVLNLAQSKNFHL<br>RPRDLISNINVIVLELKGSETTFMCEYADETATIVEFLNR<br>WITFCQSIISTLT |
| SEQ ID NO: 5 | IL2 mutein DNA | GCCCCTACCTCCTCCAGCACCAAGAAAACCCAGCTGCAGC<br>TCGAACATCTGCTGCTGGCCCTGCAGATGATCCTGAACGG<br>CATCAACAACTACAAGAACCCCAAGCTGACCCGGATGCTG<br>ACCTTCAAGTTCTACATGCCCAAGAAGGCCACCGAGCTGA<br>AACATCTGCAGTGCCTGGAAGAGGAACTGAAGCCCCTGGA<br>AGAAGTGCTGAACCTGGCCCAGTCCAAGAACTTCCACCTG<br>AGGCCTCGGGACCTGATCTCCAACATCAACGTGATCGTGC<br>TGGAACTGAAGGGCTCCGAGACAACCTTCATGTGCGAGTA<br>CGCCGACGAGACAGCCACCATCGTGGAATTTCTGAACCGG<br>TGGATCACCTTCTCCCAGTCCATCATCTCCACCCTGACC |
| SEQ ID NO: 6 | IL2 mutein protein, the mutein amino acids are bolded and underlined | APTSSSTKKTQLQLEHLLLALQMILNGINNYKNPKLTRML<br>TFKFYMPKKATELKHLQCLEEELKPLEEVLNLAQSKNFHL<br>RPRDLISNINVIVLELKGSETTFMCEYADETATIVEFLNR<br>WITFSQSIISTLT |
| SEQ ID NO: 7 | IL2 DNA without signal sequence | GCCCCTACCTCCTCCAGCACCAAGAAAACCCAGCTGCAGC<br>TCGAACATCTGCTGCTGGACCTGCAGATGATCCTGAACGG<br>CATCAACAACTACAAGAACCCCAAGCTGACCCGGATGCTG<br>ACCTTCAAGTTCTACATGCCCAAGAAGGCCACCGAGCTGA<br>AACATCTGCAGTGCCTGGAAGAGGAACTGAAGCCCCTGGA<br>AGAAGTGCTGAACCTGGCCCAGTCCAAGAACTTCCACCTG<br>AGGCCTCGGGACCTGATCTCCAACATCAACGTGATCGTGC<br>TGGAACTGAAGGGCTCCGAGACAACCTTCATGTGCGAGTA<br>CGCCGACGAGACAGCCACCATCGTGGAATTTCTGAACCGG<br>TGGATCACCTTCTGCCAGTCCATCATCTCCACCCTGACC |
| SEQ ID NO: 8 | IL2 protein without signal sequence | APTSSSTKKTQLQLEHLLLDLQMILNGINNYKNPKLTRML<br>TFKFYMPKKATELKHLQCLEEELKPLEEVLNLAQSKNFHL<br>RPRDLISNINVIVLELKGSETTFMCEYADETATIVEFLNR<br>WITFCQSIISTLT |
| SEQ ID NO: 9 | IL2 mutein DNA | GCCCCTACCTCCTCCAGCACCAAGAAAACCCAGCTGCAGC<br>TCGAACATCTGCTGCTGGACCTGCAGATGATCCTGAACGG<br>CATCAACAACTACAAGAACCCCAAGCTGACCCGGATGCTG<br>ACCTTCAAGTTCTACATGCCCAAGAAGGCCACCGAGCTGA<br>AACATCTGCAGTGCCTGGAAGAGGAACTGAAGCCCCTGGA<br>AGAAGTGCTGAACCTGGCCCAGTCCAAGAACTTCCACCTG<br>AGGCCTCGGGACCTGATCTCCAACATCAACGTGATCGTGC<br>TGGAACTGAAGGGCTCCGAGACAACCTTCATGTGCGAGTA<br>CGCCGACGAGACAGCCACCATCGTGGAATTTCTGAACCGG<br>TGGATCACCTTCTCCCAGTCCATCATCTCCACCCTGACC |

TABLE 1-continued

| SEQ ID NO: 10 | IL2 mutein protein, the mutated amino acid is bolded and underlined | APTSSSTKKTQLQLEHLLLDLQMILNGINNYKNPKLTRML TFKFYMPKKATELKHLQCLEEELKPLEEVLNLAQSKNFHL RPRDLISNINVIVLELKGSETTFMCEYADETATIVEFLNR WITF<u>S</u>QSIISTLT |
|---|---|---|

TABLE 2

IgG.IL2D49A.H1

| SEQ ID NO: 11 (Combined) | HCDR1 | GFSLAPTSSSTKKTQLQLEHLLLALQMILNGINNYKNPKLTRML TFKFYMPKKATELKHLQCLEEELKPLEEVLNLAQSKNFHLRPRD LISNINVIVLELKGSETTFMCEYADETATIVEFLNRWITFCQSI ISTLTSTSGMSVG |
|---|---|---|
| SEQ ID NO: 12 (Combined) | HCDR2 | DIWWDDKKDYNPSLKS |
| SEQ ID NO: 13 (Combined) | HCDR3 | SMITNWYFDV |
| SEQ ID NO: 14 (Kabat) | HCDR1 | APTSSSTKKTQLQLEHLLLALQMILNGINNYKNPKLTRMLTFKF YMPKKATELKHLQCLEEELKPLEEVLNLAQSKNFHLRPRDLISN INVIVLELKGSETTFMCEYADETATIVEFLNRWITFCQSIISTL TSTSGMSVG |
| SEQ ID NO: 15 (Kabat) | HCDR2 | DIWWDDKKDYNPSLKS |
| SEQ ID NO: 16 (Kabat) | HCDR3 | SMITNWYFDV |
| SEQ ID NO: 17 (Chothia) | HCDR1 | GFSLAPTSSSTKKTQLQLEHLLLALQMILNGINNYKNPKLTRML TFKFYMPKKATELKHLQCLEEELKPLEEVLNLAQSKNFHLRPRD LISNINVIVLELKGSETTFMCEYADETATIVEFLNRWITFCQSI ISTLTSTSGM |
| SEQ ID NO: 18 (Chothia) | HCDR2 | WWDDK |
| SEQ ID NO: 19 (Chothia) | HCDR3 | SMITNWYFDV |
| SEQ ID NO: 20 | VH | QVTLRESGPALVKPTQTLTLTCTFSGFSLAPTSSSIKKTQLQLE HLLLALQMILNGINNYKNPKLTRMLTFKFYMPKKATELKHLQCL EEELKPLEEVLNLAQSKNFHLRPRDLISNINVIVLELKGSETTF MCEYADETATIVEFLNRWITFCQSIISTLTSTSGMSVGWIRQPP GKALEWLADIWWDDKKDYNPSLKSRLTISKDTSKNQVVLKVTNM DPADTATYYCARSMITNWYFDVWGAGTTVTVSS |
| SEQ ID NO: 21 | DNA VH | CAAGTCACACTGCGTGAAAGCGGCCCTGCCCTGGTCAAGCCCAC CCAGACCCTGACCCTGACCTGCACCTTCTCCGGCTTCAGCCTGG CCCCTACCTCCTCCAGCACCAAGAAAACCCAGCTGCAGCTCGAA CATCTGCTGCTGGCCCTGCAGATGATCCTGAACGGCATCAACAA CTACAAGAACCCCAAGCTGACCCGGATGCTGACCTTCAAGTTCT ACATGCCCAAGAAGGCCACCGAGCTGAAACATCTGCAGTGCCTG GAAGAGGAACTGAAGCCCCTGGAAGAAGTGCTGAACCTGGCCCA GTCCAAGAACTTCCACCTGAGGCCTCGGGACCTGATCTCCAACA TCAACGTGATCGTGCTGGAACTGAAGGGCTCCGAGACAACCTTC ATGTGCGAGTACGCCGACGAGACAGCCACCATCGTGGAATTTCT GAACCGGTGGATCACCTTCTGCCAGTCCATCATCTCCACCCTGA CCTCCACCTCCGGCATGTCCGTGGGCTGGATCCGGCAGCCTCCT GGCAAGGCCCTGGAGTGGCTGGCCGACATTTGGTGGGACGACAA GAAGGACTACAACCCCAGCCTGAAGTCCCGGCTGACCATCTCCA AGGACACCTCCAAGAACCAAGTGGTGCTGAAAGTGACCAACATG GACCCCGCCGACACCGCCACCTACTACTGCGCCCGGTCCATGAT CACCAACTGGTACTTCGACGTGTGGGGCGCTGGCACCACCGTGA CCGTGTCCTCT |
| SEQ ID NO: 22 | Heavy Chain | QVTLRESGPALVKPTQTLTLTCTFSGFSLAPTSSSTKKTQLQLE HLLLALQMILNGINNYKNPKLTRMLTFKFYMPKKATELKHLQCL EEELKPLEEVLNLAQSKNFHLRPRDLISNINVIVLELKGSETTF MCEYADETATIVEFLNRWITFCQSIISTLTSTSGMSVGWIRQPP GKALEWLADIWWDDKKDYNPSLKSRLTISKDTSKNQVVLKVTNM DPADTATYYCARSMITNWYFDVWGAGTTVTVSSASTKGPSVFPL APSSKSTSGGTAALGCLVKDYFPEPVTVSWNSGALTSGVHTFPA |

TABLE 2-continued

| | | |
|---|---|---|
| | | VLQSSGLYSLSSVVTVPSSSLGTQTYICNVNHKPSNTKVDKRVE PKSCDKTHTCPPCPAPELLGGPSVFLFPPKPKDTLMISRTPEVT CVVVAVSHEDPEVKFNWYVDGVEVHNAKTKPREEQYNSTYRVVS VLTVLHQDWLNGKEYKCKVSNKALAAPIEKTISKAKGQPREPQV YTLPPSREEMTKNQVSLTCLVKGFYPSDIAVEWESNGQPENNYK TTPPVLDSDGSFFLYSKLTVDKSRWQQGNVFSCSVMHEALHNHY TQKSLSLSPGK |
| SEQ ID NO: 23 | DNA Heavy Chain | CAAGTCACACTGCGTGAAAGCGGCCCTGCCCTGGTCAAGCCCAC CCAGACCCTGACCCTGACCTGCACCTTCTCCGGCTTCAGCCTGG CCCCTACCTCCTCCAGCACCAAGAAAACCCAGCTGCAGCTCGAA CATCTGCTGCTGGCCCTGCAGATGATCCTGAACGGCATCAACAA CTACAAGAACCCCAAGCTGACCCGGATGCTGACCTTCAAGTTCT ACATGCCCAAGAAGGCCACCGAGCTGAAACATCTGCAGTGCCTG GAAGAGGAACTGAAGCCCTGGAAGAAGTGCTGAACCTGGCCCA GTCCAAGAACTTCCACCTGAGGCCTCGGGACCTGATCTCCAACA TCAACGTGATCGTGCTGGAACTGAAGGGCTCCGAGACAACCTTC ATGTGCGAGTACGCCGACGAGACAGCCACCATCGTGGAATTTCT GAACCGGTGGATCACCTTCTGCCAGTCCATCATCTCCACCCTGA CCTCCACCTCCGGCATGTCCGTGGGCTGGATCCGGCAGCCTCCT GGCAAGGCCCTGGAGTGGCTGGCCGACATTTGTGGGACGACAA GAAGGACTACAACCCCAGCCTGAAGTCCCGGCTGACCATCTCCA AGGACACCTCCAAGAACCAAGTGGTGCTGAAAGTGACCAACATG GACCCCGCCGACACCGCCACCTACTACTGCGCCCGGTCCATGAT CACCAACTGGTACTTCGACGTGTGGGGCGCTGGCACCACCGTGA CCGTGTCCTCTGCTAGCACCAAGGGCCCCTCCGTGTTCCCTCTG GCCCCTTCCAGCAAGTCTACCTCCGGCGGCACAGCTGCTCTGGG CTGCCTGGTCAAGGACTACTTCCCTGAGCCTGTGACAGTGTCCT GGAACTCTGGCGCCCTGACCTCTGGCGTGCACACCTTCCCTGCC GTGCTGCAGTCCTCCGGCCTGTACTCCCTGTCCTCCGTGGTCAC AGTGCCTTCAAGCAGCCTGGGCACCCAGACCTATATCTGCAACG TGAACCACAAGCCTTCCAACACCAAGGTGGACAAGCGGGTGGAG CCTAAGTCCTGCGACAAGACCCACACCTGTCCTCCCTGCCCTGC TCCTGAACTGCTGGGCGGCCCTTCTGTGTTCCTGTTCCCTCCAA AGCCCAAGGACACCCTGATGATCTCCCGGACCCCTGAAGTGACC TGCGTGGTGGTGGCCGTGTCCCACGAGGATCCTGAAGTGAAGTT CAATTGGTACGTGGACGGCGTGGAGGTGCACAACGCCAAGACCA AGCCTCGGGAGGAACAGTACAACTCCACCTACCGGGTGGTGTCC GTGCTGACCGTGCTGCACCAGGACTGGCTGAACGGCAAAGAGTA CAAGTGCAAAGTCTCCAACAAGGCCCTGGCCGCCCCTATCGAAA AGACAATCTCCAAGGCCAAGGGCCAGCCTAGGGAACCCCAGGTG TACACCCTGCCACCCAGCCGGGAGGAAATGACCAAGAACCAGGT GTCCCTGACCTGTCTGGTCAAGGGCTTCTACCCTTCCGATATCG CCGTGGAGTGGGAGTCTAACGGCCAGCCTGAGAACAACTACAAG ACCACCCCTCCTGTGCTGGACTCCGACGGCTCCTTCTTCCTGTA CTCCAAACTGACCGTGGACAAGTCCCGGTGGCAGCAGGGCAACG TGTTCTCCTGCTCCGTGATGCACGAGGCCCTGCACAACCACTAC ACCCAGAAGTCCCTGTCCCTGTCTCCCGGCAAG |
| SEQ ID NO: 24 (Combined) | LCDR1 | KAQLSVGYMH |
| SEQ ID NO: 25 (Combined) | LCDR2 | DTSKLAS |
| SEQ ID NO: 26 (Combined) | LCDR3 | FQGSGYPFT |
| SEQ ID NO: 27 (Kabat) | LCDR1 | KAQLSVGYMH |
| SEQ ID NO: 28 (Kabat) | LCDR2 | DTSKLAS |
| SEQ ID NO: 29 (Kabat) | LCDR3 | FQGSGYPFT |
| SEQ ID NO: 30 (Chothia) | LCDR1 | QLSVGY |
| SEQ ID NO: 31 (Chothia) | LCDR2 | DTS |
| SEQ ID NO: 32 (Chothia) | LCDR3 | GSGYPF |
| SEQ ID NO: 33 | VL | DIQMTQSPSTLSASVGDRVTITCKAQLSVGYMHWYQQKPGKAPK LLIYDTSKLASGVPSRFSGSGSGTEFTLTISSLQPDDFATYYCF QGSGYPFTFGGGTKLEIK |

TABLE 2-continued

| SEQ ID NO: 34 | DNA VL | GACATCCAGATGACCCAGAGCCCCTCCACCCTGTCCGCCTCCGT<br>GGGCGACAGAGTGACCATCACTTGCAAGGCCCAGCTGTCCGTGG<br>GCTACATGCACTGGTATCAGCAGAAGCCCGGCAAGGCCCCTAAG<br>CTGCTGATCTACGACACCTCCAAGCTGGCCTCCGGCGTGCCCTC<br>CAGATTCTCCGGCTCTGGCTCCGGCACCGAGTTCACCCTGACCA<br>TCTCCAGCCTGCAGCCCGACGACTTCGCCACCTACTACTGTTTT<br>CAAGGCTCCGGCTACCCCTTCACCTTCGGCGGAGGCACCAAGCT<br>GGAAATCAAG |
| --- | --- | --- |
| SEQ ID NO: 35 | Light Chain | DIQMTQSPSTLSASVGDRVTITCKAQLSVGYMHWYQQKPGKAPK<br>LLIYDTSKLASGVPSRFSGSGSGTEFTLTISSLQPDDFATYYCF<br>QGSGYPFTFGGGTKLEIKRTVAAPSVFIFPPSDEQLKSGTASVV<br>CLLNNFYPREAKVQWKVDNALQSGNSQESVTEQDSKDSTYSLSS<br>TLTLSKADYEKHKVYACEVTHQGLSSPVTKSFNRGEC |
| SEQ ID NO: 36 | DNA Light Chain | GACATCCAGATGACCCAGAGCCCCTCCACCCTGTCCGCCTCCGT<br>GGGCGACAGAGTGACCATCACTTGCAAGGCCCAGCTGTCCGTGG<br>GCTACATGCACTGGTATCAGCAGAAGCCCGGCAAGGCCCCTAAG<br>CTGCTGATCTACGACACCTCCAAGCTGGCCTCCGGCGTGCCCTC<br>CAGATTCTCCGGCTCTGGCTCCGGCACCGAGTTCACCCTGACCA<br>TCTCCAGCCTGCAGCCCGACGACTTCGCCACCTACTACTGTTTT<br>CAAGGCTCCGGCTACCCCTTCACCTTCGGCGGAGGCACCAAGCT<br>GGAAATCAAGCGTACGGTGGCCGCTCCCAGCGTGTTCATCTTCC<br>CCCCCAGCGACGAGCAGCTGAAGAGCGGCACCGCCAGCGTGGTG<br>TGCCTGCTGAACAACTTCTACCCCCGGGAGGCCAAGGTGCAGTG<br>GAAGGTGGACAACGCCCTGCAGAGCGGCAACAGCCAGGAGAGCG<br>TCACCGAGCAGGACAGCAAGGACTCCACCTACAGCCTGAGCAGC<br>ACCCTGACCCTGAGCAAGGCCGACTACGAGAAGCATAAGGTGTA<br>CGCCTGCGAGGTGACCCACCAGGGCCTGTCCAGCCCCGTGACCA<br>AGAGCTTCAACAGGGGCGAGTGC |

IgG.IL2D49A-C154S.H1

| SEQ ID NO: 37 (Combined) | HCDR1 | GFSLAPTSSSTKKTQLQLEHLLLALQMILNGINNYKNPKLTRML<br>TFKFYMPKKATELKHLQCLEEELKPLEEVLNLAQSKNFHLRPRD<br>LISNINVIVLELKGSETTFMCEYADETATIVEFLNRWITFSQSI<br>ISTLTSTSGMSVG |
| --- | --- | --- |
| SEQ ID NO: 38 (Combined) | HCDR2 | DIWWDDKKDYNPSLKS |
| SEQ ID NO: 39 (Combined) | HCDR3 | SMITNWYFDV |
| SEQ ID NO: 40 (Kabat) | HCDR1 | APTSSSTKKTQLQLEHLLLALQMILNGINNYKNPKLTRMLTFKF<br>YMPKKATELKHLQCLEEELKPLEEVLNLAQSKNFHLRPRDLISN<br>INVIVLELKGSETTFMCEYADETATIVEFLNRWITFSQSIISTL<br>TSTSGMSVG |
| SEQ ID NO: 41 (Kabat) | HCDR2 | DIWWDDKKDYNPSLKS |
| SEQ ID NO: 42 (Kabat) | HCDR3 | SMITNWYFDV |
| SEQ ID NO: 43 (Chothia) | HCDR1 | GFSLAPTSSSTKKTQLQLEHLLLALQMILNGINNYKNPKLTRML<br>TFKFYMPKKATELKHLQCLEEELKPLEEVLNLAQSKNFHLRPRD<br>LISNINVIVLELKGSETTFMCEYADETATIVEFLNRWITFSQSI<br>ISTLTSTSGM |
| SEQ ID NO: 44 (Chothia) | HCDR2 | WWDDK |
| SEQ ID NO: 45 (Chothia) | HCDR3 | SMITNWYFDV |
| SEQ ID NO: 46 | VH | QVTLRESGPALVKPTQTLTLTCTFSGFSLAPTSSSTKKTQLQLE<br>HLLLALQMILNGINNYKNPKLTRMLTFKFYMPKKATELKHLQCL<br>EEELKPLEEVLNLAQSKNFHLRPRDLISNINVIVLELKGSETTF<br>MCEYADETATIVEFLNRWITFSQSIISTLTSTSGMSVGWIRQPP<br>GKALEWLADIWWDDKKDYNPSLKSRLTISKDTSKNQVVLKVTNM<br>DPADTATYYCARSMITNWYFDVWGAGTTVTVSS |
| SEQ ID NO: 47 | DNA VH | CAAGTCACACTGCGTGAAAGCGGCCCTGCCCTGGTCAAGCCCAC<br>CCAGACCCTGACCCTGACCTGCACCTTCTCCGGCTTCAGCCTGG<br>CCCCTACCTCCTCCAGCACCAAGAAAACCCAGCTGCAGCTCGAA<br>CATCTGCTGCTGGCCCTGCAGATGATCCTGAACGGCATCAACAA<br>CTACAAGAACCCCAAGCTGACCCGGATGCTGACCTTCAAGTTCT<br>ACATGCCCAAGAAGGCCACCGAGCTGAAACATCTGCAGTGCCTG |

TABLE 2-continued

| | | |
|---|---|---|
| | | GAAGAGGAACTGAAGCCCCTGGAAGAAGTGCTGAACCTGGCCCA<br>GTCCAAGAACTTCCACCTGAGGCCTCGGGACCTGATCTCCAACA<br>TCAACGTGATCGTGCTGGAACTGAAGGGCTCCGAGACAACCTTC<br>ATGTGCGAGTACGCCGACGAGACAGCCACCATCGTGGAATTTCT<br>GAACCGGTGGATCACCTTCTCCCAGTCCATCATCTCCACCCTGA<br>CCTCCACCTCCGGCATGTCCGTGGGCTGGATCCGGCAGCCTCCT<br>GGCAAGGCCCTGGAGTGGCTGGCCGACATTTGGTGGGACGACAA<br>GAAGGACTACAACCCCAGCCTGAAGTCCCGGCTGACCATCTCCA<br>AGGACACCTCCAAGAACCAAGTGGTGCTGAAAGTGACCAACATG<br>GACCCCGCCGACACCGCCACCTACTACTGCGCCCGGTCCATGAT<br>CACCAACTGGTACTTCGACGTGTGGGGCGCTGGCACCACCGTGA<br>CCGTGTCCTCT |
| SEQ ID NO: 48 | Heavy<br>Chain | QVTLRESGPALVKPTQTLTLTCTFSGFSLAPTSSSTKKTQLQLE<br>HLLLALQMILNGINNYKNPKLTRMLTFKFYMPKKATELKHLQCL<br>EEELKPLEEVLNLAQSKNFHLRPRDLISNINVIVLELKGSETTF<br>MCEYADETATIVEFLNRWITFSQSIISTLTSTSGMSVGWIRQPP<br>GKALEWLADIWWDDKKDYNPSLKSRLTISKDTSKNQVVLKVTNM<br>DPADTATYYCARSMITNWYFDVWGAGTTVTVSSASTKGPSVFPL<br>APSSKSTSGGTAALGCLVKDYFPEPVTVSWNSGALTSGVHTFPA<br>VLQSSGLYSLSSVVTVPSSSLGTQTYICNVNHKPSNTKVDKRVE<br>PKSCDKTHTCPPCPAPELLGGPSVFLFPPKPKDTLMISRTPEVT<br>CVVVAVSHEDPEVKFNWYVDGVEVHNAKTKPREEQYNSTYRVVS<br>VLTVLHQDWLNGKEYKCKVSNKALAAPIEKTISKAKGQPREPQV<br>YTLPPSREEMTKNQVSLTCLVKGFYPSDIAVEWESNGQPENNYK<br>TTPPVLDSDGSFFLYSKLTVDKSRWQQGNVFSCSVMHEALHNHY<br>TQKSLSLSPGK |
| SEQ ID NO: 49 | DNA<br>Heavy<br>Chain | CAAGTCACACTGCGTGAAAGCGGCCCTGCCCTGGTCAAGCCCAC<br>CCAGACCCTGACCCTGACCTGCACCTTCTCCGGCTTCAGCCTGG<br>CCCCTACCTCCTCCAGCACCAAGAAAACCCAGCTGCAGCTCGAA<br>CATCTGCTGCTGGCCCTGCAGATGATCCTGAACGGCATCAACAA<br>CTACAAGAACCCCAAGCTGACCCGGATGCTGACCTTCAAGTTCT<br>ACATGCCCAAGAAGGCCACCGAGCTGAAACATCTGCAGTGCCTG<br>GAAGAGGAACTGAAGCCCCTGGAAGAAGTGCTGAACCTGGCCCA<br>GTCCAAGAACTTCCACCTGAGGCCTCGGGACCTGATCTCCAACA<br>TCAACGTGATCGTGCTGGAACTGAAGGGCTCCGAGACAACCTTC<br>ATGTGCGAGTACGCCGACGAGACAGCCACCATCGTGGAATTTCT<br>GAACCGGTGGATCACCTTCTCCCAGTCCATCATCTCCACCCTGA<br>CCTCCACCTCCGGCATGTCCGTGGGCTGGATCCGGCAGCCTCCT<br>GGCAAGGCCCTGGAGTGGCTGGCCGACATTTGGTGGGACGACAA<br>GAAGGACTACAACCCCAGCCTGAAGTCCCGGCTGACCATCTCCA<br>AGGACACCTCCAAGAACCAAGTGGTGCTGAAAGTGACCAACATG<br>GACCCCGCCGACACCGCCACCTACTACTGCGCCCGGTCCATGAT<br>CACCAACTGGTACTTCGACGTGTGGGGCGCTGGCACCACCGTGA<br>CCGTGTCCTCTGCTAGCACCAAGGGCCCCTCCGTGTTCCCTCTG<br>GCCCCTTCCAGCAAGTCTACCTCCGGCGGCACAGCTGCTCTGGG<br>CTGCCTGGTCAAGGACTACTTCCCTGAGCCTGTGACAGTGTCCT<br>GGAACTCTGGCGCCCTGACCTCTGGCGTGCACACCTTCCCTGCC<br>GTGCTGCAGTCCTCCGGCCTGTACTCCCTGTCCTCCGTGGTCAC<br>AGTGCCTTCAAGCAGCCTGGGCACCCAGACCTATATCTGCAACG<br>TGAACCACAAGCCTTCCAACACCAAGGTGGACAAGCGGGTGGAG<br>CCTAAGTCCTGCGACAAGACCCACACCTGTCCTCCCTGCCCTGC<br>TCCTGAACTGCTGGGCGGCCCTTCTGTGTTCCTGTTCCCTCCAA<br>AGCCCAAGGACACCCTGATGATCTCCCGGACCCCTGAAGTGACC<br>TGCGTGGTGGTGGCCGTGTCCCACGAGGATCCTGAAGTGAAGTT<br>CAATTGGTACGTGGACGGCGTGGAGGTGCACAACGCCAAGACCA<br>AGCCTCGGGAGGAACAGTACAACTCCACCTACCGGGTGGTGTCC<br>GTGCTGACCGTGCTGCACCAGGACTGGCTGAACGGCAAAGAGTA<br>CAAGTGCAAAGTCTCCAACAAGGCCCTGGCCGCCCCTATCGAAA<br>AGACAATCTCCAAGGCCAAGGGCCAGCCTAGGGAACCCCAGGTG<br>TACACCCTGCCACCCAGCCGGGAGGAAATGACCAAGAACCAGGT<br>GTCCCTGACCTGTCTGGTCAAGGGCTTCTACCCTTCCGATATCG<br>CCGTGGAGTGGGAGTCTAACGGCCAGCCTGAGAACAACTACAAG<br>ACCACCCCTCCTGTGCTGGACTCCGACGGCTCCTTCTTCCTGTA<br>CTCCAAACTGACCGTGGACAAGTCCCGGTGGCAGCAGGGCAACG<br>TGTTCTCCTGCTCCGTGATGCACGAGGCCCTGCACAACCACTAC<br>ACCCAGAAGTCCCTGTCCCTGTCTCCCGGCAAG |
| SEQ ID NO: 50<br>(Combined) | LCDR1 | KAQLSVGYMH |
| SEQ ID NO: 51<br>(Combined) | LCDR2 | DTSKLAS |
| SEQ ID NO: 52<br>(Combined) | LCDR3 | FQGSGYPFT |
| SEQ ID NO: 53<br>(Kabat) | LCDR1 | KAQLSVGYMH |

TABLE 2-continued

| SEQ ID NO: 54 (Kabat) | LCDR2 | DTSKLAS |
|---|---|---|
| SEQ ID NO: 55 (Kabat) | LCDR3 | FQGSGYPFT |
| SEQ ID NO: 56 (Chothia) | LCDR1 | QLSVGY |
| SEQ ID NO: 57 (Chothia) | LCDR2 | DTS |
| SEQ ID NO: 58 (Chothia) | LCDR3 | GSGYPF |
| SEQ ID NO: 59 | VL | DIQMTQSPSTLSASVGDRVTITCKAQLSVGYMHWYQQKPGKAPK LLIYDTSKLASGVPSRFSGSGSGTEFTLTISSLQPDDFATYYCF QGSGYPFTFGGGTKLEIK |
| SEQ ID NO: 60 | DNA VL | GACATCCAGATGACCCAGAGCCCCTCCACCCTGTCCGCCTCCGT GGGCGACAGAGTGACCATCACTTGCAAGGCCCAGCTGTCCGTGG GCTACATGCACTGGTATCAGCAGAAGCCCGGCAAGGCCCCTAAG CTGCTGATCTACGACACCTCCAAGCTGGCCTCCGGCGTGCCCTC CAGATTCTCCGGCTCTGGCTCCGGCACCGAGTTCACCCTGACCA TCTCCAGCCTGCAGCCCGACGACTTCGCCACCTACTACTGTTTT CAAGGCTCCGGCTACCCCTTCACCTTCGGCGGAGGCACCAAGCT GGAAATCAAG |
| SEQ ID NO: 61 | Light Chain | DIQMTQSPSTLSASVGDRVTITCKAQLSVGYMHWYQQKPGKAPK LLIYDTSKLASGVPSRFSGSGSGTEFTLTISSLQPDDFATYYCF QGSGYPFTFGGGTKLEIKRTVAAPSVFIFPPSDEQLKSGTASVV CLLNNFYPREAKVQWKVDNALQSGNSQESVTEQDSKDSTYSLSS TLTLSKADYEKHKVYACEVTHQGLSSPVTKSFNRGEC |
| SEQ ID NO: 62 | DNA Light Chain | GACATCCAGATGACCCAGAGCCCCTCCACCCTGTCCGCCTCCGT GGGCGACAGAGTGACCATCACTTGCAAGGCCCAGCTGTCCGTGG GCTACATGCACTGGTATCAGCAGAAGCCCGGCAAGGCCCCTAAG CTGCTGATCTACGACACCTCCAAGCTGGCCTCCGGCGTGCCCTC CAGATTCTCCGGCTCTGGCTCCGGCACCGAGTTCACCCTGACCA TCTCCAGCCTGCAGCCCGACGACTTCGCCACCTACTACTGTTTT CAAGGCTCCGGCTACCCCTTCACCTTCGGCGGAGGCACCAAGCT GGAAATCAAGCGTACGGTGGCCGCTCCCAGCGTGTTCATCTTCC CCCCCAGCGACGAGCAGCTGAAGAGCGGCACCGCCAGCGTGGTG TGCCTGCTGAACAACTTCTACCCCCGGGAGGCCAAGGTGCAGTG GAAGGTGGACAACGCCCTGCAGAGCGGCAACAGCCAGGAGAGCG TCACCGAGCAGGACAGCAAGGACTCCACCTACAGCCTGAGCAGC ACCCTGACCCTGAGCAAGGCCGACTACGAGAAGCATAAGGTGTA CGCCTGCGAGGTGACCCACCAGGGCCTGTCCAGCCCCGTGACCA AGAGCTTCAACAGGGGCGAGTGC |

IgG.IL2.L3

| SEQ ID NO: 63 (Combined) | HCDR1 | GFSLSTSGMSVG |
|---|---|---|
| SEQ ID NO: 64 (Combined) | HCDR2 | DIWWDDKKDYNPSLKS |
| SEQ ID NO: 65 (Combined) | HCDR3 | SMITNWYFDV |
| SEQ ID NO: 66 (Kabat) | HCDR1 | TSGMSVG |
| SEQ ID NO: 67 (Kabat) | HCDR2 | DIWWDDKKDYNPSLKS |
| SEQ ID NO: 68 (Kabat) | HCDR3 | SMITNWYFDV |
| SEQ ID NO: 69 (Chothia) | HCDR1 | GFSLSTSGM |
| SEQ ID NO: 70 (Chothia) | HCDR2 | WWDDK |
| SEQ ID NO: 71 (Chothia) | HCDR3 | SMITNWYFDV |

TABLE 2-continued

| SEQ ID NO: 72 | VH | QVTLRESGPALVKPTQTLTLTCTFSGFSLSTSGMSVGWIRQPPG KALEWLADIWWDDKKDYNPSLKSRLTISKDTSKNQVVLKVTNMD PADTATYYCARSMITNWYFDVWGAGTTVTVSS |
|---|---|---|
| SEQ ID NO: 73 | DNA VH | CAAGTCACCCTGCGTGAAAGCGGCCCTGCCCTGGTCAAGCCCAC CCAGACCCTGACCCTGACCTGCACCTTCTCCGGCTTCTCCCTGT CCACCTCCGGCATGTCCGTGGGCTGGATCCGGCAGCCTCCTGGC AAGGCCCTGGAGTGGCTGGCCGACATTTGGTGGGACGACAAGAA GGACTACAACCCCAGCCTGAAGTCCCGGCTGACCATCTCCAAGG ACACCTCCAAGAACCAAGTGGTGCTGAAAGTGACCAACATGGAC CCCGCCGACACCGCCACCTACTACTGCGCCCGGTCCATGATCAC CAACTGGTACTTCGACGTGTGGGGCGCTGGCACCACCGTGACCG TGTCCTCT |
| SEQ ID NO: 74 | Heavy Chain | QVTLRESGPALVKPTQTLTLTCTFSGFSLSTSGMSVGWIRQPPG KALEWLADIWWDDKKDYNPSLKSRLTISKDTSKNQVVLKVTNMD PADTATYYCARSMITNWYFDVWGAGTTVTVSSASTKGPSVFPLA PSSKSTSGGTAALGCLVKDYFPEPVTVSWNSGALTSGVHTFPAV LQSSGLYSLSSVVTVPSSSLGTQTYICNVNHKPSNTKVDKRVEP KSCDKTHTCPPCPAPELLGGPSVFLFPPKPKDTLMISRTPEVTC VVVAVSHEDPEVKFNWYVDGVEVHNAKTKPREEQYNSTYRVVSV LTVLHQDWLNGKEYKCKVSNKALAAPIEKTISKAKGQPREPQVY TLPPSREEMTKNQVSLTCLVKGFYPSDIAVEWESNGQPENNYKT TPPVLDSDGSFFLYSKLTVDKSRWQQGNVFSCSVMHEALHNHYT QKSLSLSPGK |
| SEQ ID NO: 75 | DNA Heavy Chain | CAAGTCACCCTGCGTGAAAGCGGCCCTGCCCTGGTCAAGCCCAC CCAGACCCTGACCCTGACCTGCACCTTCTCCGGCTTCTCCCTGT CCACCTCCGGCATGTCCGTGGGCTGGATCCGGCAGCCTCCTGGC AAGGCCCTGGAGTGGCTGGCCGACATTTGGTGGGACGACAAGAA GGACTACAACCCCAGCCTGAAGTCCCGGCTGACCATCTCCAAGG ACACCTCCAAGAACCAAGTGGTGCTGAAAGTGACCAACATGGAC CCCGCCGACACCGCCACCTACTACTGCGCCCGGTCCATGATCAC CAACTGGTACTTCGACGTGTGGGGCGCTGGCACCACCGTGACCG TGTCCTCTGCTAGCACCAAGGGCCCCTCCGTGTTCCCTCTGGCC CCTTCCAGCAAGTCTACCTCCGGCGGCACAGCTGCTCTGGGCTG CCTGGTCAAGGACTACTTCCCTGAGCCTGTGACAGTGTCCTGGA ACTCTGGCGCCCTGACCTCTGGCGTGCACACCTTCCCTGCCGTG CTGCAGTCCTCCGGCCTGTACTCCCTGTCCTCCGTGGTCACAGT GCCTTCAAGCAGCCTGGGCACCCAGACCTATATCTGCAACGTGA ACCACAAGCCTTCCAACACCAAGGTGGACAAGCGGGTGGAGCCT AAGTCCTGCGACAAGACCCACACCTGTCCTCCCTGCCCTGCTCC TGAACTGCTGGGCGGCCCTTCTGTGTTCCTGTTCCCTCCAAAGC CCAAGGACACCCTGATGATCTCCCGGACCCCTGAAGTGACCTGC GTGGTGGTGGCCGTGTCCCACGAGGATCCTGAAGTGAAGTTCAA TTGGTACGTGGACGGCGTGGAGGTGCACAACGCCAAGACCAAGC CTCGGGAGGAACAGTACAACTCCACCTACCGGGTGGTGTCCGTG CTGACCGTGCTGCACCAGGACTGGCTGAACGGCAAAGAGTACAA GTGCAAAGTCTCCAACAAGGCCCTGGCCGCCCCTATCGAAAAGA CAATCTCCAAGGCCAAGGGCCAGCCTAGGGAACCCCAGGTGTAC ACCCTGCCACCCAGCCGGGAGGAAATGACCAAGAACCAGGTGTC CCTGACCTGTCTGGTCAAGGGCTTCTACCCTTCCGATATCGCCG TGGAGTGGGAGTCTAACGGCCAGCCTGAGAACAACTACAAGACC ACCCCTCCTGTGCTGGACTCCGACGGCTCCTTCTTCCTGTACTC CAAACTGACCGTGGACAAGTCCCGGTGGCAGCAGGGCAACGTGT TCTCCTGCTCCGTGATGCACGAGGCCCTGCACAACCACTACACC CAGAAGTCCCTGTCCCTGTCTCCCGGCAAG |
| SEQ ID NO: 76 (Combined) | LCDR1 | KAQLSVGYMH |
| SEQ ID NO: 77 (Combined) | LCDR2 | DTSKLAS |
| SEQ ID NO: 78 (Combined) | LCDR3 | FQGSGAPTSSSTKKTQLQLEHLLLDLQMILNGINNYKNPKLTRM LTFKFYMPKKATELKHLQCLEEELKPLEEVLNLAQSKNFHLRPR DLISNINIVLELKGSETTFMCEYADETATIVEFLNRWITFCQS IISTLTYPFT |
| SEQ ID NO: 79 (Kabat) | LCDR1 | KAQLSVGYMH |
| SEQ ID NO: 80 (Kabat) | LCDR2 | DTSKLAS |
| SEQ ID NO: 81 (Kabat) | LCDR3 | FQGSGAPTSSSTKKTQLQLEHLLLDLQMILNGINNYKNPKLTRM LTFKFYMPKKATELKHLQCLEEELKPLEEVLNLAQSKNFHLRPR DLISNINIVLELKGSETTFMCEYADETATIVEFLNRWITFCQS IISTLTYPFT |

TABLE 2-continued

| SEQ ID NO: 82 (Chothia) | LCDR1 | QLSVGY |
|---|---|---|
| SEQ ID NO: 83 (Chothia) | LCDR2 | DTS |
| SEQ ID NO: 84 (Chothia) | LCDR3 | GSGAPTSSSTKKTQLQLEHLLLDLQMILNGINNYKNPKLTRMLT FKFYMPKKATELKHLQCLEEELKPLEEVLNLAQSKNFHLRPRDL ISNINVIVLELKGSETTFMCEYADETATIVEFLNRWITFCQSII STLTYPF |
| SEQ ID NO: 85 | VL | DIQMTQSPSTLSASVGDRVTITCKAQLSVGYMHWYQQKPGKAPK LLIYDTSKLASGVPSRFSGSGSGTEFTLTISSLQPDDFATYYCF QGSGAPTSSSTKKTQLQLEHLLLDLQMILNGINNYKNPKLTRML TFKFYMPKKATELKHLQCLEEELKPLEEVLNLAQSKNFHLPRD LISNINVIVLELKGSETTFMCEYADETATIVEFLNRWITFCQSI ISTLTYPFTFGGGTKLEIK |
| SEQ ID NO: 86 | DNA VL | GACATCCAGATGACCCAGAGCCCCTCCACCCTGTCCGCCTCCGT GGGCGACAGAGTGACCATCACTTGCAAGGCCCAGCTGTCCGTGG GCTACATGCACTGGTATCAGCAGAAGCCCGGCAAGGCCCCTAAG CTGCTGATCTACGACACCTCCAAGCTGGCCTCCGGCGTGCCCTC CAGATTCTCCGGCTCTGGCTCCGGCACCGAGTTCACCCTGACCA TCTCCAGCCTGCAGCCCGACGACTTCGCCACCTACTACTGTTTT CAAGGCTCTGGCGCCCCTACCTCCTCCAGCACCAAGAAAACCCA GCTGCAGCTCGAACATCTGCTGCTGGACCTGCAGATGATCCTGA ACGGCATCAACAACTACAAGAACCCCAAGCTGACCCGGATGCTG ACCTTCAAGTTCTACATGCCCAAGAAGGCCACCGAGCTGAAACA TCTGCAGTGCCTGGAAGAGGAACTGAAGCCCCTGGAAGAAGTGC TGAACCTGGCCCAGTCCAAGAACTTCCACCTGAGGCCTCGGGAC CTGATCTCCAACATCAACGTGATCGTGCTGGAACTGAAGGGCTC CGAGACAACCTTCATGTGCGAGTACGCCGACGAGACAGCCACCA TCGTGGAATTTCTGAACCGGTGGATCACCTTCTGCCAGTCCATC ATCTCCACCCTGACCTACCCCTTCACCTTCGGCGGAGGCACCAA GCTGGAAATCAAG |
| SEQ ID NO: 87 | Light Chain | DIQMTQSPSTLSASVGDRVTITCKAQLSVGYMHWYQQKPGKAPK LLIYDTSKLASGVPSRFSGSGSGTEFTLTISSLQPDDFATYYCF QGSGAPTSSSTKKTQLQLEHLLLDLQMILNGINNYKNPKLTRML TFKFYMPKKATELKHLQCLEEELKPLEEVLNLAQSKNFHLPRD LISNINVIVLELKGSETTFMCEYADETATIVEFLNRWITFCQSI ISTLTYPFTFGGGTKLEIKRTVAAPSVFIFPPSDEQLKSGTASV VCLLNNFYPREAKVQWKVDNALQSGNSQESVTEQDSKDSTYSLS STLTLSKADYEKHKVYACEVTHQGLSSPVTKSFNRGEC |
| SEQ ID NO: 88 | DNA Light Chain | GACATCCAGATGACCCAGAGCCCCTCCACCCTGTCCGCCTCCGT GGGCGACAGAGTGACCATCACTTGCAAGGCCCAGCTGTCCGTGG GCTACATGCACTGGTATCAGCAGAAGCCCGGCAAGGCCCCTAAG CTGCTGATCTACGACACCTCCAAGCTGGCCTCCGGCGTGCCCTC CAGATTCTCCGGCTCTGGCTCCGGCACCGAGTTCACCCTGACCA TCTCCAGCCTGCAGCCCGACGACTTCGCCACCTACTACTGTTTT CAAGGCTCTGGCGCCCCTACCTCCTCCAGCACCAAGAAAACCCA GCTGCAGCTCGAACATCTGCTGCTGGACCTGCAGATGATCCTGA ACGGCATCAACAACTACAAGAACCCCAAGCTGACCCGGATGCTG ACCTTCAAGTTCTACATGCCCAAGAAGGCCACCGAGCTGAAACA TCTGCAGTGCCTGGAAGAGGAACTGAAGCCCCTGGAAGAAGTGC TGAACCTGGCCCAGTCCAAGAACTTCCACCTGAGGCCTCGGGAC CTGATCTCCAACATCAACGTGATCGTGCTGGAACTGAAGGGCTC CGAGACAACCTTCATGTGCGAGTACGCCGACGAGACAGCCACCA TCGTGGAATTTCTGAACCGGTGGATCACCTTCTGCCAGTCCATC ATCTCCACCCTGACCTACCCCTTCACCTTCGGCGGAGGCACCAA GCTGGAAATCAAGCGTACGGTGGCCGCTCCCAGCGTGTTCATCT TCCCCCCCAGCGACGAGCAGCTGAAGAGCGGCACCGCCAGCGTG GTGTGCCTGCTGAACAACTTCTACCCCCGGGAGGCCAAGGTGCA GTGGAAGGTGGACAACGCCCTGCAGAGCGGCAACAGCCAGGAGA GCGTCACCGAGCAGGACAGCAAGGACTCCACCTACAGCCTGAGC AGCACCCTGACCCTGAGCAAGGCCGACTACGAGAAGCATAAGGT GTACGCCTGCGAGGTGACCCACCAGGGCCTGTCCAGCCCCGTGA CCAAGAGCTTCAACAGGGGCGAGTGC |

IgG.IL2C217S.L3

| SEQ ID NO: 89 (Combined) | HCDR1 | GFSLSTSGMSVG |
|---|---|---|
| SEQ ID NO: 90 (Combined) | HCDR2 | DIWWDDKKDYNPSLKS |
| SEQ ID NO: 91 (Combined) | HCDR3 | SMITNWYFDV |

TABLE 2-continued

| SEQ ID NO: 92 (Kabat) | HCDR1 | TSGMSVG |
|---|---|---|
| SEQ ID NO: 93 (Kabat) | HCDR2 | DIWWDDKKDYNPSLKS |
| SEQ ID NO: 94 (Kabat) | HCDR3 | SMITNWYFDV |
| SEQ ID NO: 95 (Chothia) | HCDR1 | GFSLSTSGM |
| SEQ ID NO: 96 (Chothia) | HCDR2 | WWDDK |
| SEQ ID NO: 97 (Chothia) | HCDR3 | SMITNWYFDV |
| SEQ ID NO: 98 | VH | QVTLRESGPALVKPTQTLTLTCTFSGFSLSTSGMSVGWIRQPPG KALEWLADIWWDDKKDYNPSLKSRLTISKDTSKNQVVLKVTNMD PADTATYYCARSMITNWYFDVWGAGTTVTVSS |
| SEQ ID NO: 99 | DNA VH | CAAGTCACCCTGCGTGAAAGCGGCCCTGCCCTGGTCAAGCCCAC CCAGACCCTGACCCTGACCTGCACCTTCTCCGGCTTCTCCCTGT CCACCTCCGGCATGTCCGTGGGCTGGATCCGGCAGCCTCCTGGC AAGGCCCTGGAGTGGCTGGCCGACATTTGGTGGGACGACAAGAA GGACTACAACCCCAGCCTGAAGTCCCGGCTGACCATCTCCAAGG ACACCTCCAAGAACCAAGTGGTGCTGAAAGTGACCAACATGGAC CCCGCCGACACCGCCACCTACTACTGCGCCCGGTCCATGATCAC CAACTGGTACTTCGACGTGTGGGGCGCTGGCACCACCGTGACCG TGTCCTCT |
| SEQ ID NO: 100 | Heavy Chain | QVTLRESGPALVKPTQTLTLTCTFSGFSLSTSGMSVGWIRQPPG KALEWLADIWWDDKKDYNPSLKSRLTISKDTSKNQVVLKVTNMD PADTATYYCARSMITNWYFDVWGAGTTVTVSSASTKGPSVFPLA PSSKSTSGGTAALGCLVKDYFPEPVTVSWNSGALTSGVHTFPAV LQSSGLYSLSSVVTVPSSSLGTQTYICNVNHKPSNTKVDKRVEP KSCDKTHTCPPCPAPELLGGPSVFLFPPKPKDTLMISRTPEVTC VVVAVSHEDPEVKFNWYVDGVEVHNAKTKPREEQYNSTYRVVSV LTVLHQDWLNGKEYKCKVSNKALAAPIEKTISKAKGQPREPQVY TLPPSREEMTKNQVSLTCLVKGFYPSDIAVEWESNGQPENNYKT TPPVLDSDGSFFLYSKLTVDKSRWQQGNVFSCSVMHEALHNHYT QKSLSLSPGK |
| SEQ ID NO: 101 | DNA Heavy Chain | CAAGTCACCCTGCGTGAAAGCGGCCCTGCCCTGGTCAAGCCCAC CCAGACCCTGACCCTGACCTGCACCTTCTCCGGCTTCTCCCTGT CCACCTCCGGCATGTCCGTGGGCTGGATCCGGCAGCCTCCTGGC AAGGCCCTGGAGTGGCTGGCCGACATTTGGTGGGACGACAAGAA GGACTACAACCCCAGCCTGAAGTCCCGGCTGACCATCTCCAAGG ACACCTCCAAGAACCAAGTGGTGCTGAAAGTGACCAACATGGAC CCCGCCGACACCGCCACCTACTACTGCGCCCGGTCCATGATCAC CAACTGGTACTTCGACGTGTGGGGCGCTGGCACCACCGTGACCG TGTCCTCTGCTAGCACCAAGGGCCCCTCCGTGTTCCCTCTGGCC CCTTCCAGCAAGTCTACCTCCGGCGGCACAGCTGCTCTGGGCTG CCTGGTCAAGGACTACTTCCCTGAGCCTGTGACAGTGTCCTGGA ACTCTGGCGCCCTGACCTCTGGCGTGCACACCTTCCCTGCCGTG CTGCAGTCCTCCGGCCTGTACTCCCTGTCCTCCGTGGTCACAGT GCCTTCAAGCAGCCTGGGCACCCAGACCTATATCTGCAACGTGA ACCACAAGCCTTCCAACACCAAGGTGGACAAGCGGGTGGAGCCT AAGTCCTGCGACAAGACCCACACCTGTCCTCCCTGCCCTGCTCC TGAACTGCTGGGCGGCCCTTCTGTGTTCCTGTTCCCTCCAAAGC CCAAGGACACCCTGATGATCTCCCGGACCCCTGAAGTGACCTGC GTGGTGGTGGCCGTGTCCCACGAGGATCCTGAAGTGAAGTTCAA TTGGTACGTGGACGGCGTGGAGGTGCACAACGCCAAGACCAAGC CTCGGGAGGAACAGTACAACTCCACCTACCGGGTGGTGTCCGTG CTGACCGTGCTGCACCAGGACTGGCTGAACGGCAAAGAGTACAA GTGCAAAGTCTCCAACAAGGCCCTGGCCGCCCCTATCGAAAGAC AATCTCCAAGGCCAAGGGCCAGCCTAGGGAACCCCAGGTGTAC ACCCTGCCACCCAGCCGGGAGGAAATGACCAAGAACCAGGTGTC CCTGACCTGTCTGGTCAAGGGCTTCTACCCTTCCGATATCGCCG TGGAGTGGGAGTCTAACGGCCAGCCTGAGAACAACTACAAGACC ACCCCTCCTGTGCTGGACTCCGACGGCTCCTTCTTCCTGTACTC CAAACTGACCGTGGACAAGTCCCGGTGGCAGCAGGGCAACGTGT TCTCCTGCTCCGTGATGCACGAGGCCCTGCACAACCACTACACC CAGAAGTCCCTGTCCCTGTCTCCCGGCAAG |

TABLE 2-continued

| SEQ ID NO: 102 (Combined) | LCDR1 | KAQLSVGYMH |
| --- | --- | --- |
| SEQ ID NO: 103 (Combined) | LCDR2 | DTSKLAS |
| SEQ ID NO: 104 (Combined) | LCDR3 | FQGSGAPTSSSTKKTQLQLEHLLLDLQMILNGINNYKNPKLTRM LTFKFYMPKKATELKHLQCLEEELKPLEEVLNLAQSKNFHLRPR DLISNINVIVLELKGSETTFMCEYADETATIVEFLNRWITFSQS IISTLTYPFT |
| SEQ ID NO: 105 (Kabat) | LCDR1 | KAQLSVGYMH |
| SEQ ID NO: 106 (Kabat) | LCDR2 | DTSKLAS |
| SEQ ID NO: 107 (Kabat) | LCDR3 | FQGSGAPTSSSTKKTQLQLEHLLLDLQMILNGINNYKNPKLTRM LTFKFYMPKKATELKHLQCLEEELKPLEEVLNLAQSKNFHLRPR DLISNINVIVLELKGSETTFMCEYADETATIVEFLNRWITFSQS IISTLTYPFT |
| SEQ ID NO: 108 (Chothia) | LCDR1 | QLSVGY |
| SEQ ID NO: 109 (Chothia) | LCDR2 | DTS |
| SEQ ID NO: 110 (Chothia) | LCDR3 | GSGAPTSSSTKKTQLQLEHLLLDLQMILNGINNYKNPKLTRMLT FKFYMPKKATELKHLQCLEEELKPLEEVLNLAQSKNFHLRPRDL ISNINVIVLELKGSETTFMCEYADETATIVEFLNRWITFSQSII STLTYPF |
| SEQ ID NO: 111 | VL | DIQMTQSPSTLSASVGDRVTITCKAQLSVGYMHWYQQKPGKAPK LLIYDTSKLASGVPSRFSGSGSGTEFTLTISSLQPDDFATYYCF QGSGAPTSSSTKKTQLQLEHLLLDLQMILNGINNYKNPKLTRML TFKFYMPKKATELKHLQCLEEELKPLEEVLNLAQSKNFHLRPRD LISNINVIVLELKGSETTFMCEYADETATIVEFLNRWITFSQSI ISTLTYPFTFGGGTKLEIK |
| SEQ ID NO: 112 | DNA VL | GACATCCAGATGACCCAGAGCCCCTCCACCCTGTCCGCCTCCGT GGGCGACAGAGTGACCATCACTTGCAAGGCCCAGCTGTCCGTGG GCTACATGCACTGGTATCAGCAGAAGCCCGGCAAGGCCCCTAAG CTGCTGATCTACGACACCTCCAAGCTGGCCTCCGGCGTGCCCTC CAGATTCTCCGGCTCTGGCTCCGGCACCGAGTTCACCCTGACCA TCTCCAGCCTGCAGCCCGACGACTTCGCCACCTACTACTGTTTT CAAGGCTCTGGCGCCCCTACCTCCTCCAGCACCAAGAAAACCCA GCTGCAGCTCGAACATCTGCTGCTGGACCTGCAGATGATCCTGA ACGGCATCAACAACTACAAGAACCCCAAGCTGACCCGGATGCTG ACCTTCAAGTTCTACATGCCCAAGAAGGCCACCGAGCTGAAACA TCTGCAGTGCCTGGAAGAGGAACTGAAGCCCCTGGAAGAAGTGC TGAACCTGGCCCAGTCCAAGAACTTCCACCTGAGGCCTCGGGAC CTGATCTCCAACATCAACGTGATCGTGCTGGAACTGAAGGGCTC CGAGACAACCTTCATGTGCGAGTACGCCGACGAGACAGCCACCA TCGTGGAATTTCTGAACCGGTGGATCACCTTCTCCCAGTCCATC ATCTCCACCCTGACCTACCCCTTCACCTTCGGCGGAGGCACCAA GCTGGAAATCAAG |
| SEQ ID NO: 113 | Light Chain | DIQMTQSPSTLSASVGDRVTITCKAQLSVGYMHWYQQKPGKAPK LLIYDTSKLASGVPSRFSGSGSGTEFTLTISSLQPDDFATYYCF QGSGAPTSSSTKKTQLQLEHLLLDLQMILNGINNYKNPKLTRML TFKFYMPKKATELKHLQCLEEELKPLEEVLNLAQSKNFHLRPRD LISNINVIVLELKGSETTFMCEYADETATIVEFLNRWITFSQSI ISTLTYPFTFGGGTKLEIKRTVAAPSVFIFPPSDEQLKSGTASV VCLLNNFYPREAKVQWKVDNALQSGNSQESVTEQDSKDSTYSLS STLTLSKADYEKHKVYACEVTHQGLSSPVTKSFNRGEC |
| SEQ ID NO: 114 | DNA Light Chain | GACATCCAGATGACCCAGAGCCCCTCCACCCTGTCCGCCTCCGT GGGCGACAGAGTGACCATCACTTGCAAGGCCCAGCTGTCCGTGG GCTACATGCACTGGTATCAGCAGAAGCCCGGCAAGGCCCCTAAG CTGCTGATCTACGACACCTCCAAGCTGGCCTCCGGCGTGCCCTC CAGATTCTCCGGCTCTGGCTCCGGCACCGAGTTCACCCTGACCA TCTCCAGCCTGCAGCCCGACGACTTCGCCACCTACTACTGTTTT CAAGGCTCTGGCGCCCCTACCTCCTCCAGCACCAAGAAAACCCA GCTGCAGCTCGAACATCTGCTGCTGGACCTGCAGATGATCCTGA ACGGCATCAACAACTACAAGAACCCCAAGCTGACCCGGATGCTG ACCTTCAAGTTCTACATGCCCAAGAAGGCCACCGAGCTGAAACA TCTGCAGTGCCTGGAAGAGGAACTGAAGCCCCTGGAAGAAGTGC TGAACCTGGCCCAGTCCAAGAACTTCCACCTGAGGCCTCGGGAC |

TABLE 2-continued

```
CTGATCTCCAACATCAACGTGATCGTGCTGGAACTGAAGGGCTC
CGAGACAACCTTCATGTGCGAGTACGCCGACGAGACAGCCACCA
TCGTGGAATTTCTGAACCGGTGGATCACCTTCTCCCAGTCCATC
ATCTCCACCCTGACCTACCCCTTCACCTTCGGCGGAGGCACCAA
GCTGGAAATCAAGCGTACGGTGGCCGCTCCCAGCGTGTTCATCT
TCCCCCCCAGCGACGAGCAGCTGAAGAGCGGCACCGCCAGCGTG
GTGTGCCTGCTGAACAACTTCTACCCCCGGGAGGCCAAGGTGCA
GTGGAAGGTGGACAACGCCCTGCAGAGCGGCAACAGCCAGGAGA
GCGTCACCGAGCAGGACAGCAAGGACTCCACCTACAGCCTGAGC
AGCACCCTGACCCTGAGCAAGGCCGACTACGAGAAGCATAAGGT
GTACGCCTGCGAGGTGACCCACCAGGGCCTGTCCAGCCCCGTGA
CCAAGAGCTTCAACAGGGGCGAGTGC
```

Example 2

Antibody Cytokine Engrafted Proteins Show Greater Activity on Treg Cells and Increased Half Life IgG.IL2D49A.H1 and IgG.IL2.L3 were selected as they acheived the desired biological effects over Proleukin® (FIG. 1 summarizes relative changes). These effects include; selectivity for the IL-2R on Tregs vs. Tcon and NK cells, greater half-life expansion of Tregs vs. Tcon and NK cells in mice.

In assessing for high affinity IL-2 receptor stimulation, both Proleukin® and IgG.IL2D49A.H1 graft showed comparable signal potency on Treg cells, but IgG.IL2D49A.H1 showed decreased to no activity on both CD8 Teffector cells and NK cells, unlike Proleukin®. IL2 engrafted into CDRL3 (IgG.IL2.L3) showed less signal potency on Tregs than Proleukin®, but no activity on NK cells. Human Peripheral blood mononuclear cells (hPBMC) were purchased from HemaCare Corp. and tested in vitro with either Proleukin®, IgG.IL2D49A.H1 or IgG.IL2.L3 to assess selective activity on the IL-2 high affinity receptor. Cells were rested in serum free test media, and added to each well. Either antibody cytokine engrafted protein or native human IL-2 were added to the wells, and incubated for 20 min at 37° C. After 20 min, cells were fixed, stained with surface markers, permeabilized and stained with STAT5 antibody (BD Biosciences) following manufacturer's instructions.

Pharmacokinetics of IgG.IL2D49A.H1 or IgG.IL2.L3 in plasma showed an extended half-life over Proleukin® after only 1 dose. Cellular expansion was assessed in the spleen of pre-diabetic NOD mice 8 days after one treatment with either Proleukin® or the grafts. IgG.IL2D49A.H1 achieved superior Treg expansion over Teffector cells and NK cells and was better tolerated than Proleukin® in pre-diabetic mice. The summary of the STAT5 stimulation, the PK/PD of IgG.IL2D49A.H1 and IgG.IL2.L3 is shown in FIG. 2. This shows that antibody cytokine engrafted proteins can not only have greater half-life than Proleukin®, but stimulation of the targeted Treg cells, without unwanted stimulation of Teffector and NK cells.

Example 3

Antibody Cytokine Engrafed Protein Shows Greater Activity on Treg Cells

The non-obese diabetic (NOD) mouse develops type 1 diabetes spontaneously and is often used as an animal model for human type 1 diabetes. Pre-diabetic NOD mice were administered equimolar Proleukin® (3× weekly) and different antibody cytokine engrafted proteins (1×/week). Eight days after first treatment, spleens were processed to obtain a single cell suspension and washed in RPMI (10% FBS). Red blood cells were lysed with Red Blood Cell Lysis Buffer (Sigma #R7757) and cells counted for cell number and viability. FACS staining was performed under standard protocols using FACS buffer (1×PBS+0.5% BSA+0.05% sodium azide). Cells were stained with surface antibodies: Rat anti-mouse CD3-BV605 (BD Pharmingen #563004), Rat anti-mouse CD4-Pacific Blue (BD Pharmingen #558107), Rat antimouse CD8-PerCp (BD Pharmingen #553036), CD44 FITC (Pharmingen #553133) Rat anti-mouse CD25-APC (Ebioscience #17-0251), and subsequently fixed/permeabilized and stained for FoxP3 according to the Anti-Mouse/Rat FoxP3 Staining Set PE (Ebioscience #72-5775). Cells were analyzed on the BD LSR Fortessa® or BD FACS LSR II®, and data analyzed with FlowJo® software. FIG. 3 shows the fold values and ratios calculated from each spleen as an absolute number, comparing IgG.IL2D49A.H1 and IgG.IL2D113A.H1 with Proleukin®. The increased expansion of Treg cells without expansion of CD8 T effector cells or NK cells with IgG.IL2D49A.H1 is shown in the top row. This is in contrast to low dose and higher dose Proleukin®, which leads to expansion of all cell types.

Example 4

IL-2R Signaling Potency is Reduced in CD4 Tcon and CD8 Teff but Not in Tregs In Vitro Both Proleukin® and IgG.IL2D49A.H1 were tested in vitro for signal potency on the IL-2R, on both human and cynomologus monkey PBMC. Both IgG.IL2D49A.H1 and Proleukin® at equimolar IL2 concentrations showed similar signal potency on the Treg cells which express high affinity IL-2R, but only IgG.IL2D49A.H1 showed reduced potency on conventional CD4 and CD8 T effector cells which express the low affinity IL-2 receptor. These results were observed in both human and cynomolgus PBMC. For the assay, PBMC cells were rested in serum-free test media, and added to each well. Either IgG.IL2D49A.H1 or Proleukin® were added to the wells, and incubated for 20 minutes at 37° C. After 20 minutes, cells were fixed, stained with surface markers, permeabilized and stained with STAT5 antibody (BD Biosciences) following manufacturer's instructions. Cells were analyzed on the BD LSR Fortessa® and data analyzed with FlowJo® software.

The result as shown in FIG. 4, was especially apparent. Both in human and cynomologus PBMC, pSTAT5 activation by IgG.IL2D49A.H1 was found on Tregs, with very little on CD8 T effectors.

Example 5

IgG.IL2D49A.H1 Expands Functional and Stable Tregs In Vitro

Improved selectivity for Tregs is accompanied by a functional effect. Tregs expanded with IgG.IL2D49A.H1 are equivalent or better suppressors of Teffectors than Proleukin® expanded Tregs. For this assay, human PBMC were purified from whole blood by centrifugation over Ficoll-Hypaque gradients (GE HealthCare cat#17-1440-03). PBMCs were RBC Lysed (Amimed cat # 3-13F00-H). CD4+ Tcells were enriched using EasySep CD4+ T-cell enrichment kit (StemCell Technologies cat#19052). Enriched CD4+ were stained with V500 anti-CD4 (clone RPAT4), PerCP-Cy5.5 anti-CD127 (and APC anti-CD25 and sorted to isolate CD4+CD127-CD25+ natural regulatory T cells (nTregs) and CD4+ CD127+CD25− T responder (Tresp). Sorted Tregs were plated ($1 \times 10^5$/100 μl/well) in replicates in 96-well round-bottom microplates filled with medium and stimulated with microbeads at 3:1 bead-to-cell ratios in the presence of 1 nM or 0.3 nM Proleukin® or IgG.IL2D49A.H1 at equimolar concentrations. After 24 hour incubation at 37° C., wells were refilled with 100 μl medium containing the same IL2 concentration. On day 3, cultures were suspended, split in half and refilled with 100 μl medium containing the same IL2 concentration. On day 6, cultures were processed as on day 3. On day 8, cells were harvested, pooled in tubes and the beads removed by placing tubes on a multistand magnet for 1-2 minutes. Supernatants containing cells were collected and centrifuged at 200 g for 5 minutes at room temperature. Cells were then counted, and plated again at about $5 \times 10^5$/ml in 48-well flat-bottom microplates filled with medium containing ⅕ of the original IL2 concentration. After 2 days rest, cells were harvested, counted and analyzed or used in suppression assay. Expanded Tregs and freshly thawed CD4+CD127+CD25− T responder (Tresp) cells were labeled as described in manufacturer's instructions with 0.8 μM CTViolet (Life Technologies cat# C34557) and 1 μM CFSE (Life Technologies cat# C34554), respectively. To assess the suppressive properties of expanded Tregs, $3 \times 10^4$ CFSE-labeled Tresp were plated in triplicates alone or with CTViolet-labeled Tregs (different Tresp:Treg ratio) and stimulated with Dynabeads at 1:8 bead-to-cell ratio (final volume 200 μl/well). After 4-5 days, cells were collected and the proliferation of responder cells evaluated by flow cytometry.

The methylation status was evaluated in fresh and expanded Tregs compared with Tresp cells. Genomic DNA (gDNA) was isolated from >$5.0 \times 10^5$ cells using Allprep® DNA/RNA Mini from Qiagen (cat #80204). Then, 200 ng of gDNA was processed using Imprint® DNA modification kit from Sigma (cat #MOD50) to convert unmethylated cytosines to uracil (while the methylated cytosines remain unchanged). Quantitative methylation was then evaluated on 8 ng of bisulfite converted gDNA using sequence-specific probe-based real-time PCR utilizing EpiTect MethyLight® PCR+ROX (Qiagen cat #59496), Epitect control DNA (Qiagen cat #59695), Standard methylated (Life Technologies, cat #12AAZ7FP) and unmethylated (Life Technologies, cat #12AAZ7FP) plasmids, Treg-specific demethylated region (TSDR) methylated and unmethylated forward and reverse primers, and probes (MicroSynth). The percentage of methylation was calculated as described in the EpiTect MethyLight® PCR Handbook.

Figure 5:
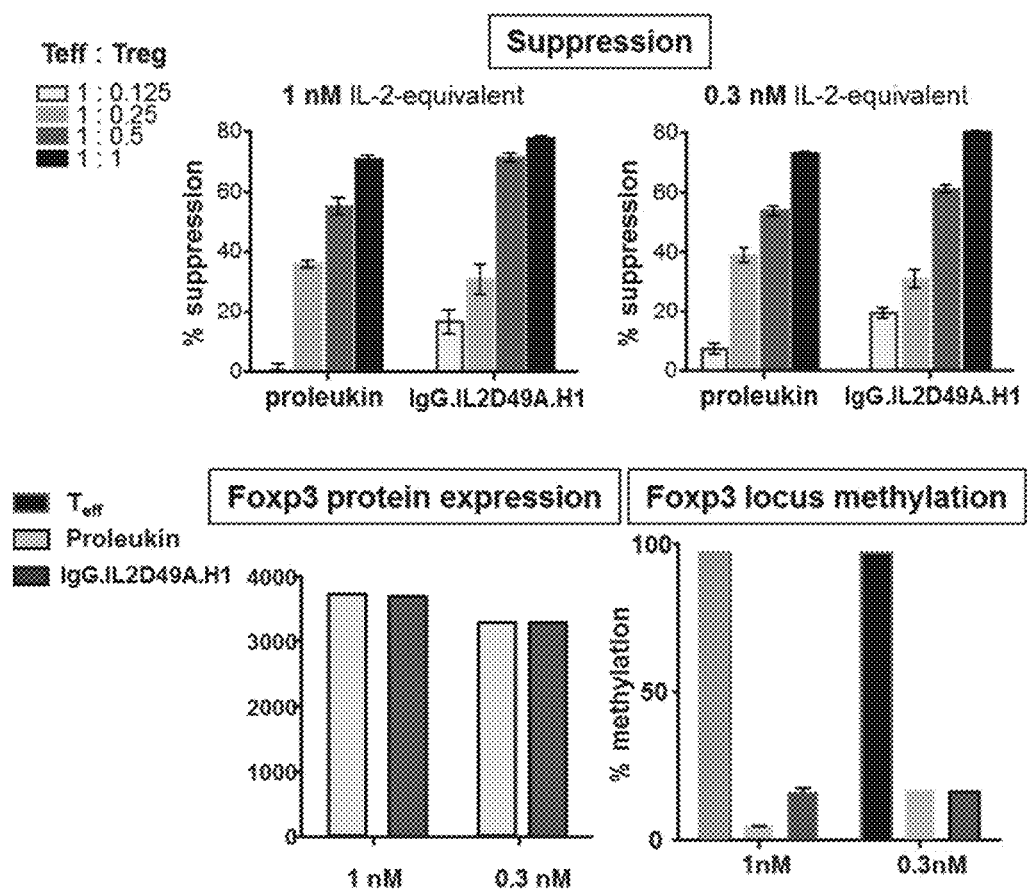
FIG. 5 shows experimental data that Tregs expanded with antibody cytokine engrafted proteins (e.g. IgG.IL2D49A.H1) are better suppressors of T effector cells (Teff) (see upper panel). The lower panel shows experimental data that Treg cells expanded by antibody cytokine engrafted proteins are stable by Foxp3 protein expression and by Foxp3 methylation.

FIG. 5 shows graphically the stable demethylation of the Foxp3 locus with Proleukin® and IgG.IL2D49A.H1 expanded Tregs. Human Tregs expanded with IgG.IL2D49A.H1 in vitro are stable by Foxp3 expression and demethylation, which leads to stable Treg cells.

Example 6

Potency on IL-2R Signaling Reduced in Human NKs In Vitro with IgG.IL2D49.H1

Figure 6:
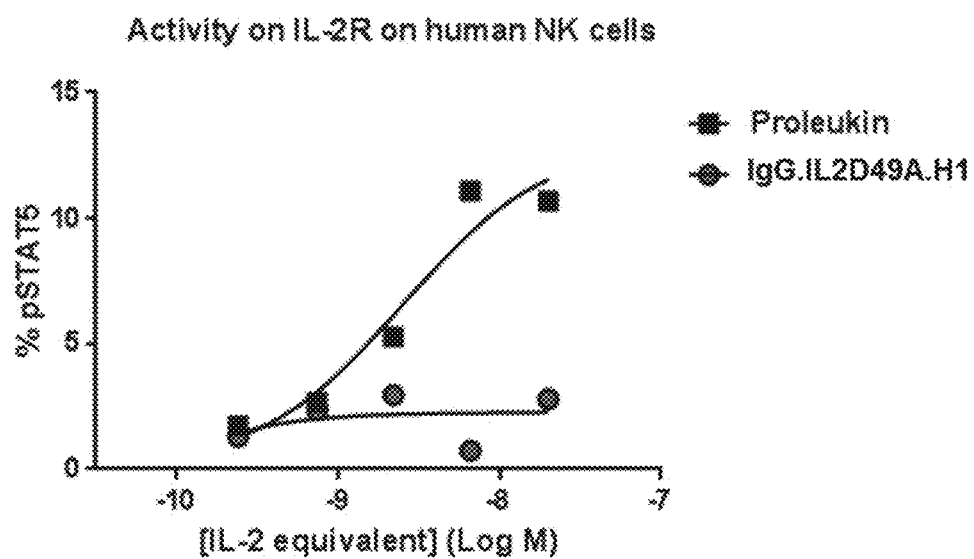
FIG. 6 shows experimental data that antibody cytokine engrafted proteins have little to no effect on NK cells which express the IL2 low affinity receptor. In contrast, Proleukin® stimulates NK cells as measured by pSTAT5 activation.

IgG.IL2D49A.H1 showed reduced potency of signaling in NK cells compared to Proleukin® at equimolar concentrations. PBMC cells were rested in serum-free test media, and added to each well. Either IgG.IL2D49A.H1 or Proleukin® were added to the wells, and incubated for 20 minutes at 37° C. After 20 minutes, cells were fixed with 1.6% formaldehyde, washed and stained with surface markers. After 30 minutes at room temperature, samples were washed and re-suspended cell pellets were permeabilized with −20° C. methanol, washed and stained with STAT5 and DNA intercalators. Cells were run on Cytof and data analyzed with FlowJo® software. The results are shown in FIG. 6, wherein IgG.IL2D49A.H1 had little to no effect on NK cells. In contrast, Proleukin® treatement increased pSTAT5 activity on NK cells, as an undesired side effect of the Proleukin® treatment.

Example 7

Evaluation of the Pharmacokinetic (PK), Pharmacodynamics (PD), and Toxicological Effects of IgG.IL2D49A.H1 When Administered Subcutaneously to Female Cynomolgus Monkeys IgG.IL2D49A.H1 in cynomolgus monkeys showed extended pharmacokinetics, superior Treg expansion over Teffector cells and less toxicity than low-dose Proleukin®. This nonclinical laboratory study was conducted in accordance with the Novartis Animal Care and Use Committee-approved generic protocol no. TX 4039, with this protocol and with facility Standard Operating Procedures (SOPs).

Animals were dosed subcutaneously with either IgG.IL2D49A.H1 or Proleukin® on the first day of the study. Blood was collected from all animals at each dose level on study. Day 1 at pre-dose, 1 hour, 6 hours and 12 hours post-dose, and then at days 2, 3, 4 , 5, 6, 7, 8, 10, and 12. All blood samples for pharmacokinetics and pharmacodynamics were centrifuged, and plasma samples obtained. Resulting plasma samples were transferred into a single polypropylene tube and frozen at approximately −70° C. or below. All samples were analyzed, and concentrations of IgG.IL2D49A.H1 and Proleukin® in plasma measured using immuno assays. Pharmacokinetic parameters such as half-life were calculated, and cells immunophenotyped by FACS for pharmacodynamics. The IL-2/IL-2 Gyros assay protocol is as follows. Each sample was run in duplicate, with each of the duplicated analyses requiring 5 μL of sample that had been diluted 1:20. Capture antibody is goat anti-human IL-2 biotinylated antibody (R&D Systems BAF202) and detected with Alexa 647 anti-human IL-2, Clone MQ1-17H12 (Biolegend 500315) LOQ: 0.08 ng/ml, all immunoassay were conducted using a Gyrolab Bio-affy200® with Gyros CD-200s®.

Figure 7:
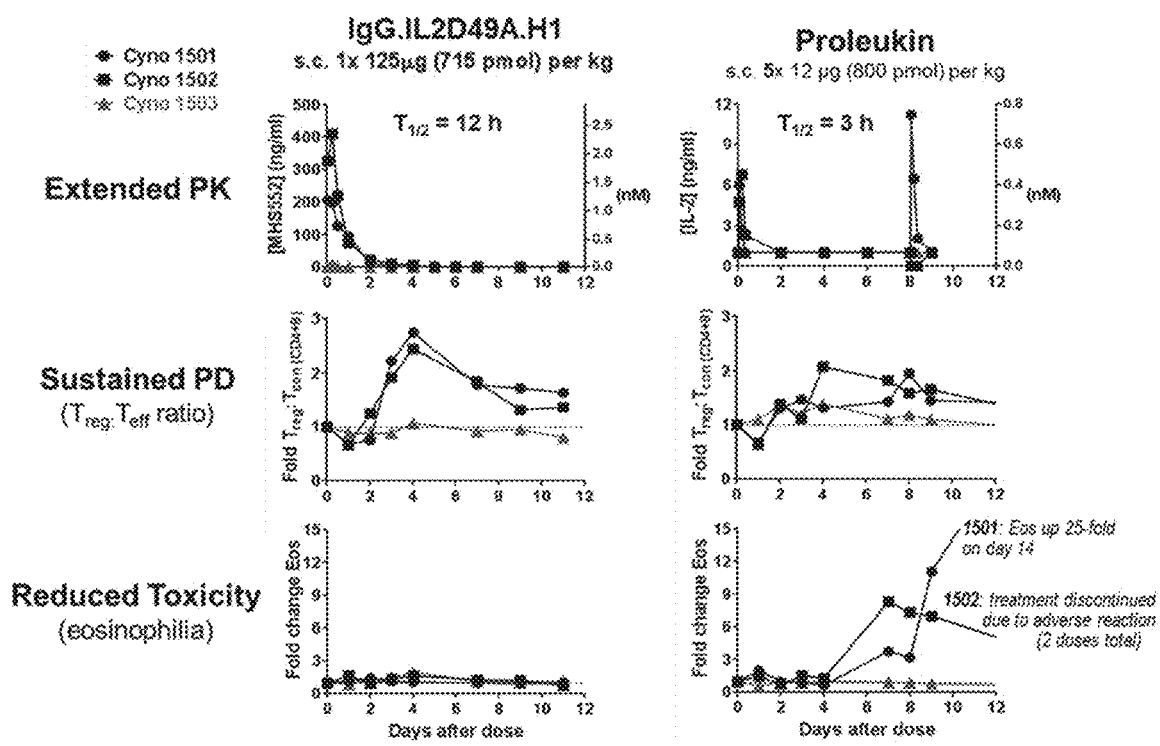
FIG. 7 shows experimental data on pharmacokinetic (PK), pharmacodynamic (PD) and toxicity profile of an antibody cytokine engrafted protein compared to Proleukin® in cynomolgous monkeys. For example, IgG.IL2D49A.H1 has a much reduced eosinophilia toxicity profile than Proleukin®.

FIG. 7 shows the contrasts between IgG.IL2D49A.H1 and Proleukin®. IgG.IL2D49A.H1 has a half-life of 12 hours, whereas Proleukin® has a half-life of 3 hours. With the extended half-life of IgG.IL2D49A.H1 comes increased Treg activity and much reduced eosinophilia toxicity.

Example 8

IgG.IL2D49A.H1 Shows an Extended Half-Life Over Proleukin®

Figure 8:
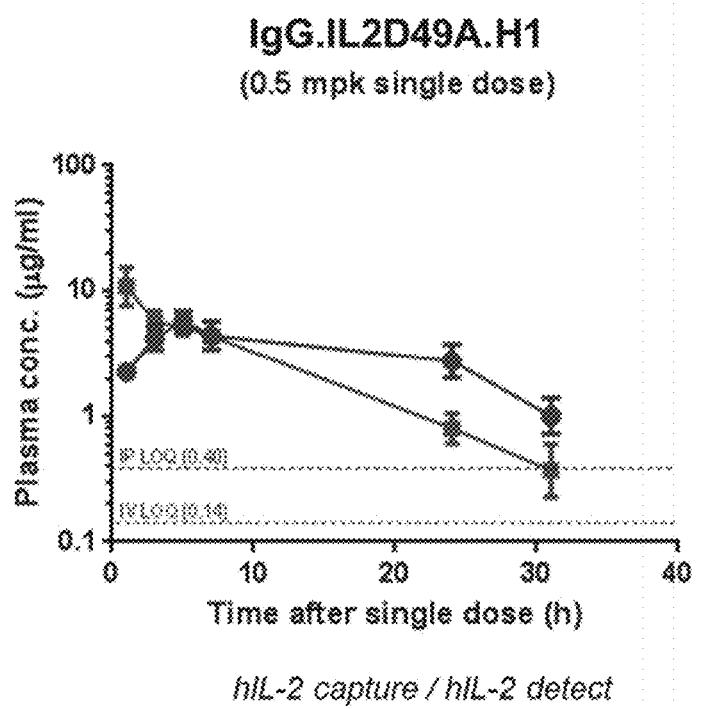
FIG. 8 is a graph depicting the extended half-life of IgG.IL2D49.H1.

IgG.IL2D49A.H1 showed a half-life of approximately 12 hours compared to the Proleukin® half-life of 4 hours after a single administration. Naïve CD-1 animals were dosed intravenously or subcutaneously and blood collected from all animals at pre-dose, 1 hour, 3, 7, 24, 31, 48, 55 and 72 hours post-dose. Blood samples were centrifuged, and plasma samples obtained. Resulting plasma samples were transferred into a single polypropylene tube and frozen at −80° C. All samples were analysed, and concentrations of IgG.IL2D49A.H1 in plasma was measured using immunoassays. The IL-2/IL-2 Gyros assay protocol is as follows. Each sample was run in duplicate, with each of the duplicated analyses requiring 54 of sample that had been diluted 1:20. Capture antibody is goat anti-human IL-2 biotinylated antibody (R&D Systems BAF202) and detected with Alexa 647 anti-human IL-2, Clone MQ1-17H12 (Biolegend 500315) LOQ: 0.08 ng/ml, all immunoassay were conducted using a Gyrolab Bioaffy200® with Gyros CD-200s®. This assay expands upon the half-life determination of Example 7. The results of this assay is shown in FIG. 8, where the half-life of IgG.IL2D49A.H1 is determined to be 12-14 hours, in contrast with Proleukin® which has a half-life of 4 hours.

Example 9

Human Tregs Expand But Not Teffectors or NK Cells in Mice with Xeno-GvHD

Figure 9:
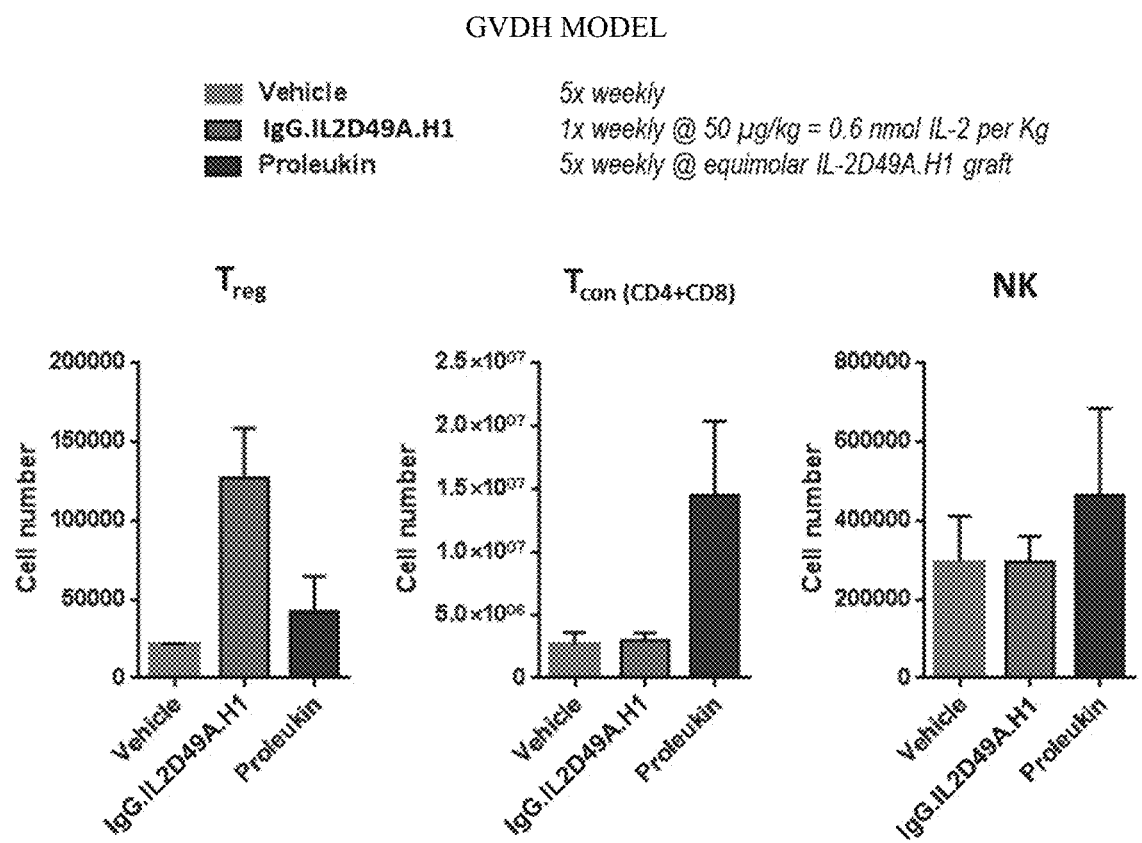
FIG. 9 shows experimental data on antibody cytokine engrafted protein molecules in a mouse GvHD model. This shows that treatment with antibody cytokine engrafted proteins in this model expands Tregs better than Proleukin®, while having little to no effect on CD4+/CD8+ Teff cells or NK cells.

IgG.IL2D49A.H1 selectively expands Tregs over Teffectors or NK cells in the xeno-GvHD model, while Proleukin® does not. NOD-scid IL2R gamma null mice (NSG) were injected with hPBMCs from healthy donors via intraperitoneal injection (HemaCare Corp). 24 hours after injection, the animals were dosed with either IgG.IL2D49A.H1 1x/week or Proleukin® 5x/week every week for the duration of the study. Body weight was monitored twice a week for the duration of the study. Four mice per group were harvested 28 days after the first dose, and spleens were processed to obtain single cell suspensions and washed in RPMI (10% FBS). Red blood cells were lysed with Red Blood Cell Lysis Buffer and cells counted for cell number and viability. FACS staining was performed under standard protocols using FACS buffer (1×PBS+0.5% BSA+0.05% sodium azide). Cells were stained with surface antibodies and subsequently fixed/permeabilized and stained for FoxP3 according to the Anti-Mouse/Rat FoxP3 Staining Set PE (Ebioscience #72-5775). Cells were analyzed on the BD LSR Fortessa® and data analyzed with FlowJo® software. Fold values and ratios are based on the relative number calculated from each spleen absolute number. FIG. 9 shows that IgG.IL2D49A.H1 expands Treg cells much better than Proleukin® in this mouse model and also reduces the undesired expansion of Tcons and NK cells.

Figure 10:
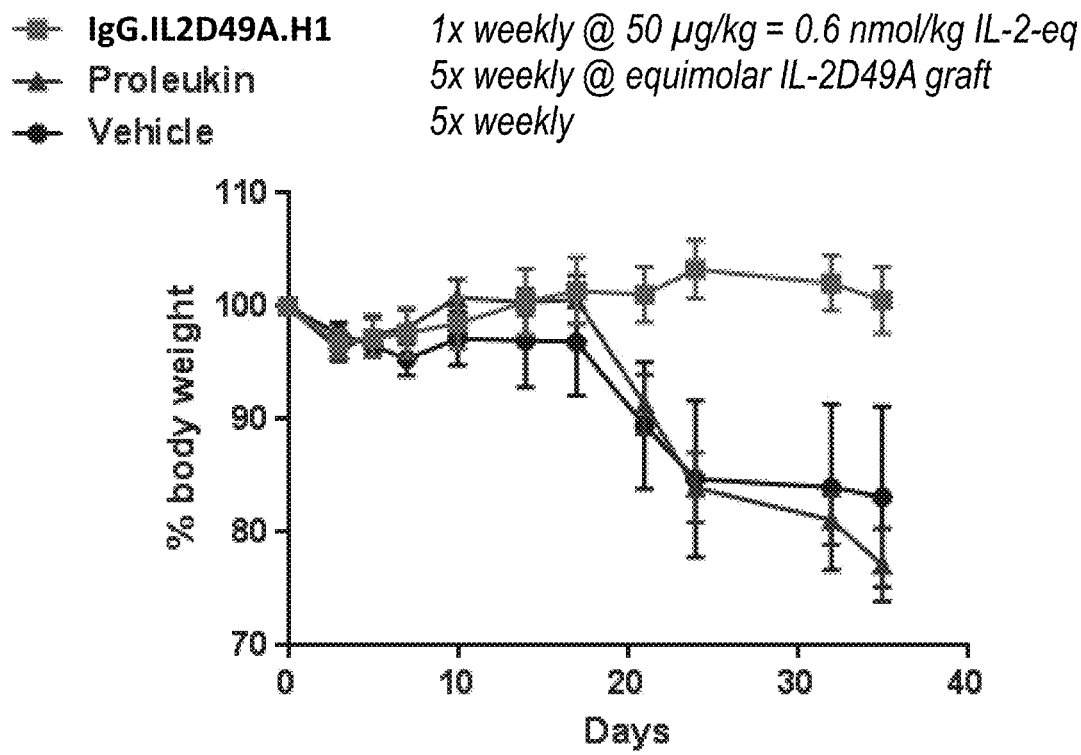
FIG. 10 shows experimental data on the loss of body weight associated with Proleukin® treatment in a GvHD mouse model, while there is little body weight loss associated with administration of IgG.IL2D49.H1.

When the xeno-GvHD mice were treated with the IgG.IL2D49.H1, and injected with human PBMCs (the foreign cells), they maintained a normal body weight over the course of the treatment. In contrast, mice treated with Proleukin® had severe body weight loss. Body weight was monitored twice a week for the duration of the study, and percent body weight was calculated taking into consideration the initial weight of the animals at the time of enrollment. This improvement is associated with the effect IgG.IL2D49A.H1 has on Treg enhancement in this model, and the data is shown graphically in FIG. 10. This data indicates that IgG.IL2D49A.H1 and other antibody cytokine engrafted proteins have a greater therapeutic index and margin for safety.

Example 10

Figure 11:
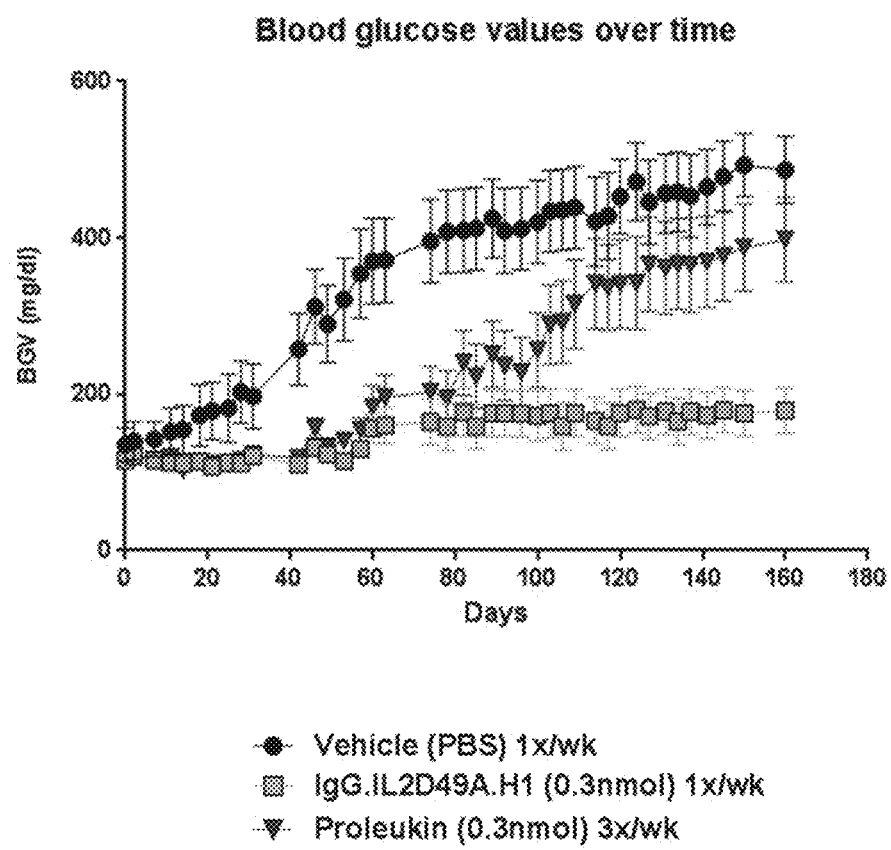
FIG. 11 shows experimental data on comparing antibody cytokine engrafted proteins to Proleukin® in a prediabetic (NOD) mouse model, and demonstrates that IgG.IL2D49A.H1 prevents Type 1 diabetes in this model.

IgG.IL2D49A.H1 Prevents Type 1 Diabetes Development in a NOD Mice Model of Diabetes Pre-diabetic NOD females were administered equimolar Proleukin® (3x weekly) and IgG.IL2D49A.H1 (1x/weekly) by intraperitoneal injection. For the duration of the study (4 months after first dose), the mice were monitored twice a week for blood glucose and body weight. FIG. 11 shows that IgG.IL2D49A.H1 treated mice maintain a low blood glucose value. As such, mice treated with IgG.IL2D49A.H1 did not progress to overt Type 1 diabetes (T1D). In contrast, Proleukin® treated mice began with low blood glucose values, but this increased over time and resulted in type 1 diabetes symptoms.

Example 11

IgG.IL2D49A.H1 Versus Low Dose Proleukin® in Pre-diabetic NOD Mice

Figure 12:
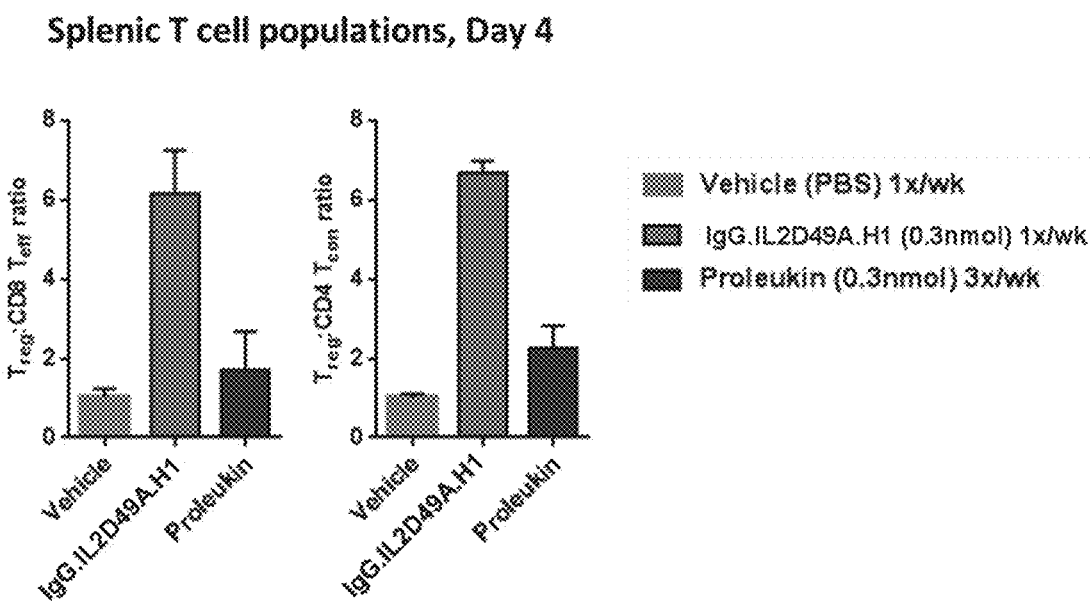
FIG. 12 shows experimental data on comparing the ratio of Treg to CD8 T effector cells in a pre-diabetic NOD mouse model.

IgG.IL2D49A.H1 showed superior Treg expansion, better tolerability and no adverse events with one dose, compared to 3 doses of Proleukin® in the NOD mouse model. Pre-diabetic NOD females were administered low dose equimolar Proleukin® (3x weekly) and IgG.IL2D49A.H1 (1x/weekly) by intraperitoneal injection. Four mice per group were taken down 4 days after the first dose, and spleens were processed to obtain single cell suspensions and washed in RPMI (10% FBS). Red blood cells were lysed with Red Blood Cell Lysis Buffer and cells counted for cell number and viability. FACS staining was performed under standard protocols using FACS buffer (1×PBS+0.5% BSA+0.05% sodium azide). Cells were stained with surface antibodies: Rat anti-mouse CD3-BV605 (BD Pharmingen #563004), Rat anti-mouse CD4-Pacific Blue (BD Pharmingen #558107), Rat antimouse CD8-PerCp (BD Pharmingen #553036), CD44 FITC (Pharmingen #553133) Rat anti-mouse CD25-APC (Ebioscience #17-0251), and subsequently fixed/permeabilized and stained for FoxP3 according to the Anti-Mouse/Rat FoxP3 Staining Set PE (Ebioscience #72-5775). Cells were analyzed on the BD LSR Fortessa® or BD FACS LSR II®, and data analyzed with FlowJo® software. Fold values and ratios are based on the relative number calculated from each spleen absolute number. Administration of a single dose of IgG.IL2D49A.H1 showed greater expansion of Tregs than repeated administration of Proleukin® in the NOD mouse model as shown in FIG. 12.

Example 12

Pharmacokinetics of an Efficacious Dose of IgG.IL2D49A.H1 in the NOD Mouse Model Pharmacokinetics of IgG.IL2D49A.H1 at 1.3 mg/kg and 0.43 mg/kg was assayed in plasma up to 48 hours after 1 dose. Pre-diabetic 10 week old NOD mice were dosed intraperitoneally with IgG.IL2D49A.H1 at two different concentrations and blood collected from all animals at 1 hour, 3, 7, 24 and 48 hours post-dose. Blood samples were centrifuged, and plasma samples obtained. Resulting plasma samples were transferred into a single polypropylene tube and frozen at −80° C. Each sample was analyzed to detect IgG.IL2D49A.H1 plasma concentrations using three different methods adapted to the Gyros platform: 1) IL2-based capture and detect, 2) IL2-based capture and hFc-based detect, and 3) hFc-based capture and detect.

Figure 13A:
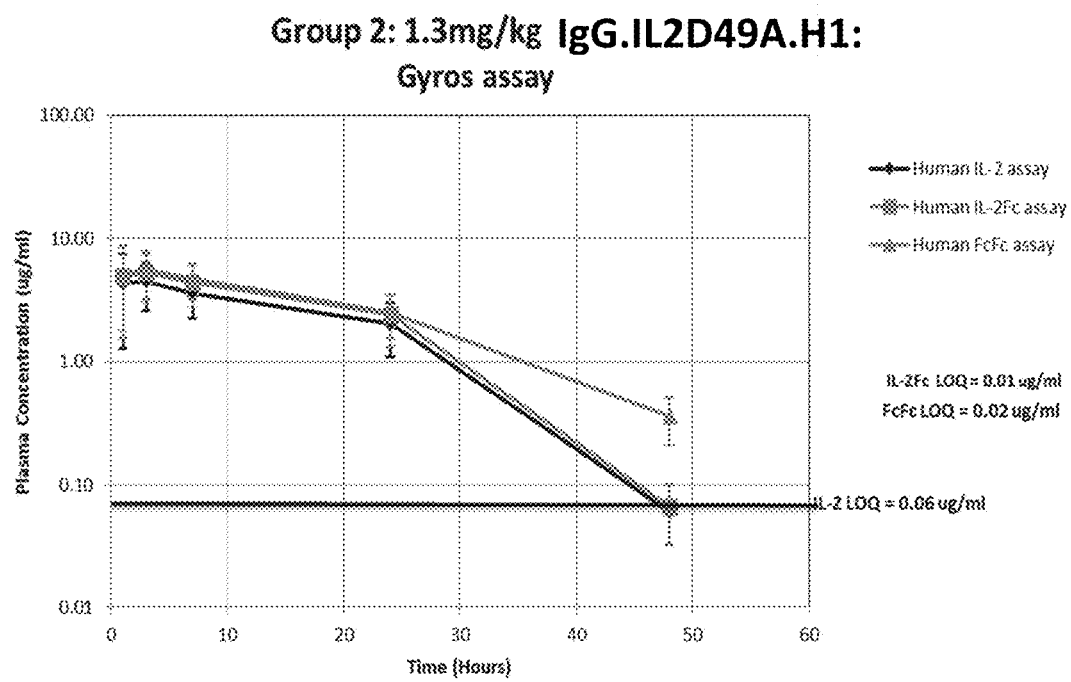
FIG. 13A shows experimental data on the pharmacokinetics of IgG.IL2D49A.H1 in the NOD mouse model at a 1.3 mg/kg dose.
Figure 13B:
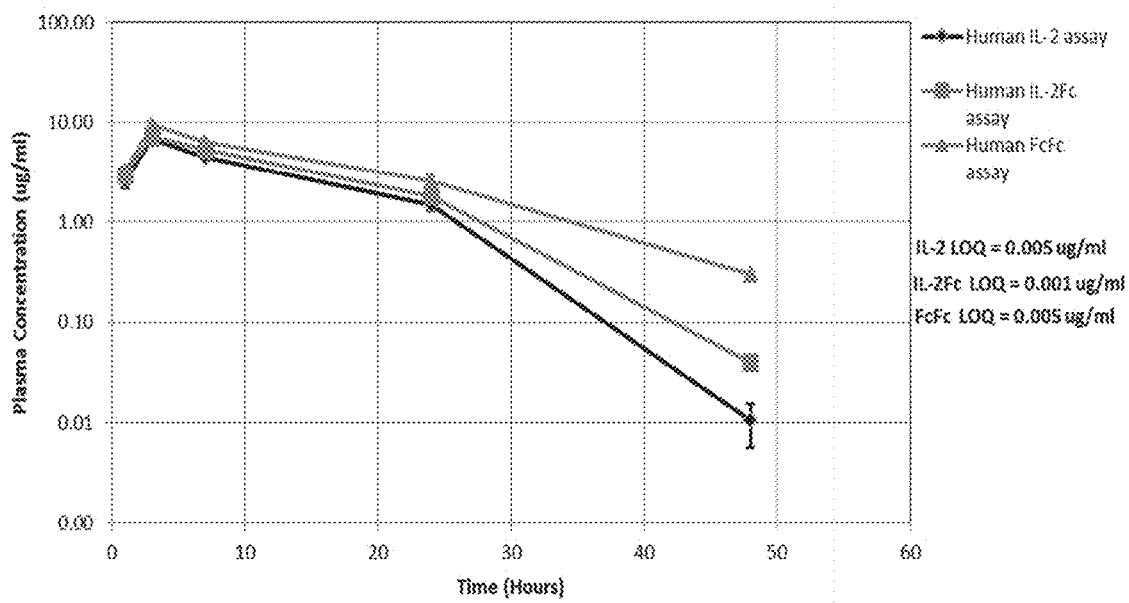
FIG. 13B shows experimental data on the pharmacokinetics of IgG.IL2D49A.H1 in the NOD mouse model at a 0.43 mg/kg dose.

Each sample was run in duplicate, with each of the duplicated analyses requiring 54 of sample that had been diluted 1:20. The Gyros IL-2/IL-2 assay uses a capture goat anti-human IL-2 biotinylated antibody (R&D Systems BAF202) and detects with Alexa 647 anti-human IL-2, Clone MQ1-17H12 (Biolegend 500315). For IL-2/Fc detection, a capture goat anti-human IL-2 biotinylated antibody (R&D Systems BAF202) is used, and for detection, an Alexa 647 goat anti-human IgG, Fc specific (Jackson ImmunoResearch 109-605-098) antibody. For the human Fc/Fc assay, a capture Biotinylated goat anti-human IgG, Fc specific (Jackson ImmunoResearch #109-065-098) was used. The detection step used an Alexa 647 goat anti-human IgG, Fcγ specific (Jackson ImmunoResearch #109-605-098). All immunoassays were conducted using a Gyrolab Bioaffy200® with Gyros CD-200s. The limit of quantification (LOQ) in this mouse model is 48 hours as shown in FIG. 13A. This is compared with Proleukin® and an IL2-Fc fusion protein in FIG. 13B. This graph shows that the LOQ is higher for antibody cyokine engrafted proteins such as IgG.IL2D49.H1.

Example 13

Dose Range Finding in Pre-diabetic NOD Mice

IgG.IL2D49A.H1 showed superior Treg expansion over both CD4 Tcon and CD8 Teffectors when compared to Proleukin® at the same equimolar concentrations. Adverse events such as mortality were found in the highest Proleukin® groups, and no mortality was seen in mice treated with any dose of IgG.IL2D49A.H1.

Pre-diabetic NOD females were administered low dose equimolar IL-2 (3×weekly) and IgG.IL2D49A.H1 (1×/weekly) by intraperitoneal injection. Three mice per group were euthanized 8 days days after the first dose and spleens harvested. Spleens were processed to obtain single cell suspensions and washed in RPMI (10% FBS). Blood was collected, red blood cells were lysed with Red Blood Cell Lysis Buffer and cells counted for cell number and viability. FACS staining was performed under standard protocols using FACS buffer (1×PBS+0.5% BSA+0.05% sodium azide). Cells were stained with surface antibodies and subsequently fixed/permeabilized and stained for FoxP3 according to the Anti-Mouse/Rat FoxP3 Staining Set PE (Ebioscience #72-5775). Cells were analyzed on the BD LSR Fortessa® and data analyzed with FlowJo® software. Ratios are based on the relative cell number calculated from each spleen. This data is provided in FIG. 14. The table provides for a dose range format for antibody cytokine engrafted proteins. It also demonstrates that IgG.IL2D49A.H1 had a greater therapeutic index than Proleukin® as dosing was well tolerated over a larger range. In contrast, the administration of Proleukin® at higher doses produced morbidity and mortality in the mice. The highest dose of Proleukin® produced sufficient morbidity and mortality that the treatment at this dose had to be discontinued.

Example 14

STAT5 Signaling on Human PBMC

Figure 15A:
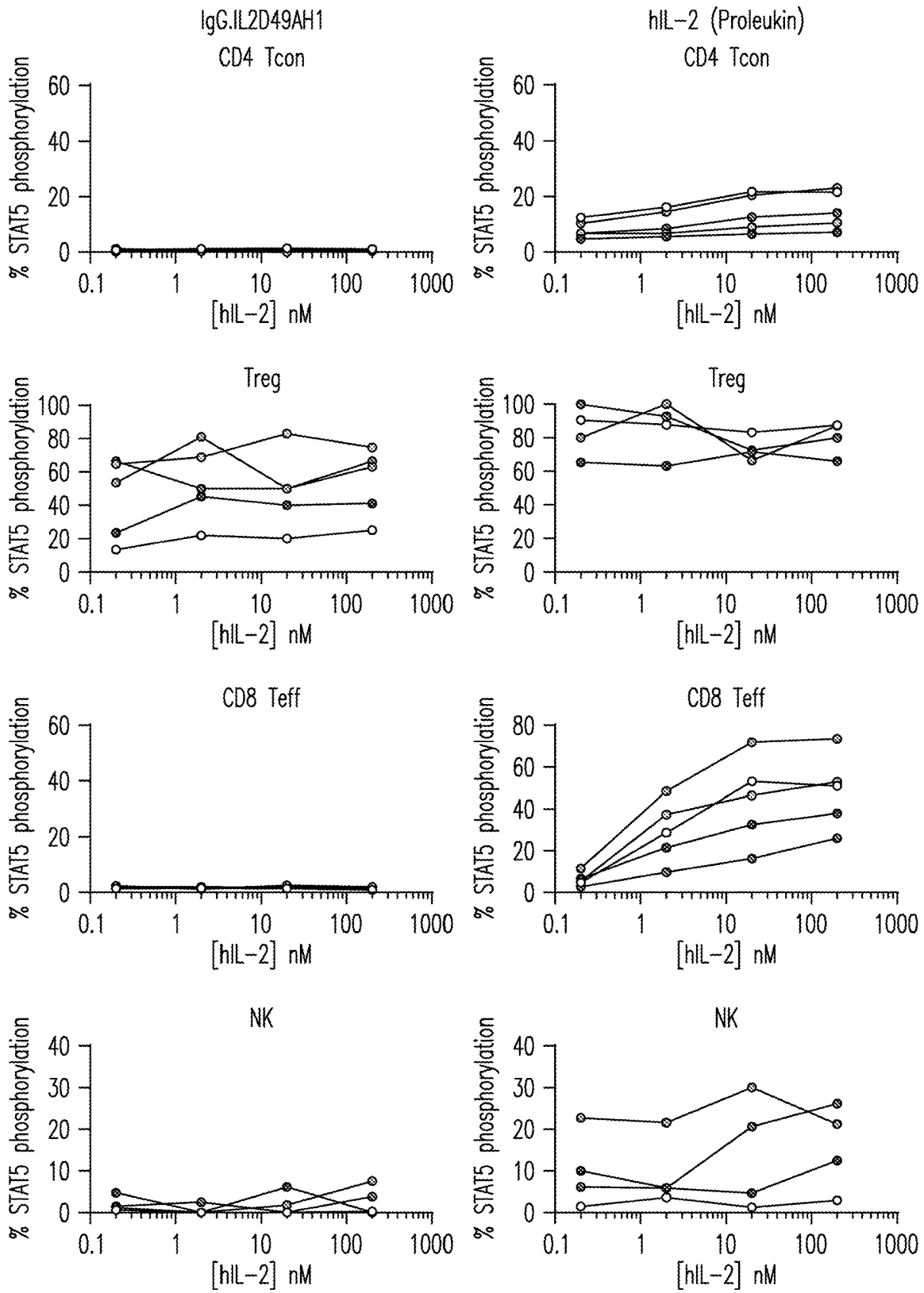
FIG. 15A shows a series of graphs depicting amount of pSTAT5 activation on human PBMCs taken from a vitiligo patent and treated in vitro with IgG.IL2D49.H1 and compared with Proleukin®.
Figure 15B:
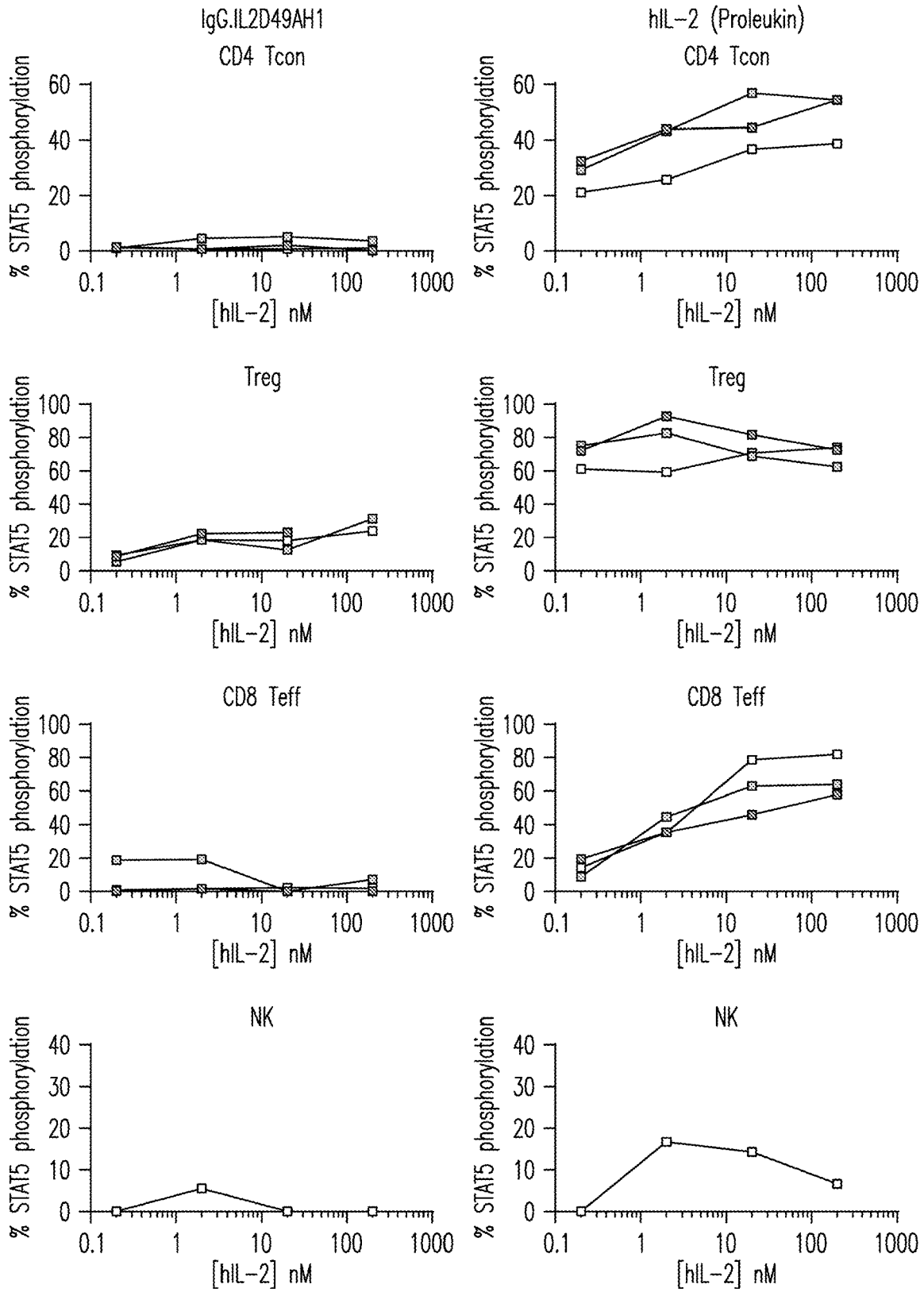
FIG. 15B shows a series of graphs depicting amount of pSTAT5 activation on human PBMCs taken from a patent with type 1 diabetes and treated in vitro with IgG.IL2D49.H1 and Proleukin®.

IgG.IL2D49A.H1 was selective for Treg activation over Tcon and NK in healthy donor human PBMC as well as in PBMC from autoimmune donors. Potency of STAT5 signaling was reduced in Tcon but not Tregs after treatment in vitro with IgG.IL2D49.H1. Human PBMC from healthy and autoimmune patients (Hemacare Corp) cells were rested in serum-free test media, and added to each well. IgG.IL2D49A.H1 was added to the wells, and incubated for 20 min at 37° C. After 20 minutes, cells were fixed, stained with surface markers, permeabilized and stained with STAT5 antibody (BD Biosciences) following manufacturer's instructions. Cells were analyzed on the BD LSR Fortessa® and data analyzed with FlowJo® software. The data in FIG. 15A indicates that IgG.IL2D49A.H1 treatment of PBMCs taken from human patients with vitiligo that there was very little activation of NK, CD4 T con, or CD8 T effector cells, while maintaining Treg activity. This result was also observed in PBMCs taken from patients with SLE and Hashimoto's disease (data not shown). FIG. 15B shows that PBMCs taken from human patients with Type 1 Diabeties (T1D) and treated with IgG.IL2D49A.H1 and Proleukin® had much reduced pSTAT5 activity on NK cells, CD8 T effector cells or CD4 Tcon cells. As IgG.IL2D49A.H1 treatment was effective in normal PBMCs and well tolerated in PBMCs taken from T1D patients, this indicates that antibody cytokine proteins would be useful in the treatment of T1D even if the patient is receiving insulin therapy. This indicates that IgG.IL2D49A.H1 would be well tolerated in patients with these immune related disorders, and is effective in dealing with these immune related disorders.

Example 15

Binding of Antibody Cytokine Engrafted Proteins

IL2 sequences containing muteins (SEQ ID NO:4 or 6) were inserted into CDR loops of an immunoglobulin chain scaffold. Antibody cytokine engrafted proteins were prepared using a variety of known immunoglobulin sequences which have been utilized in clinical settings as well as germline antibody sequences. One of the antibodies used has RSV as its antigen. To determine if engrafting IL2 into the CDRs of this antibody reduced or abrogated binding to RSV, an ELISA assay was run on RSV proteins either in PBS or a carbonate buffer. As shown in FIG. 16, this appears to be influenced by which CDR was chosen for IL2 engrafting. For example, IgG.IL2D49A.H1 has RSV binding similar to the ungrafted (un-modified) original antibody. In contrast, engrafting IL2 into the light chain of CDR3 (CDR-L3) or into CDR-H3 reduces binding. As expected, IL2 engrafted into an irrelevant antibody (Xolair) produces no binding. This demonstrates that antibody cytokine engrafted proteins can retain binding to the original target of the antibody scaffold, or this binding can be reduced.

Example 16

Treg Expansion in Non-human Primates

Figure 17:
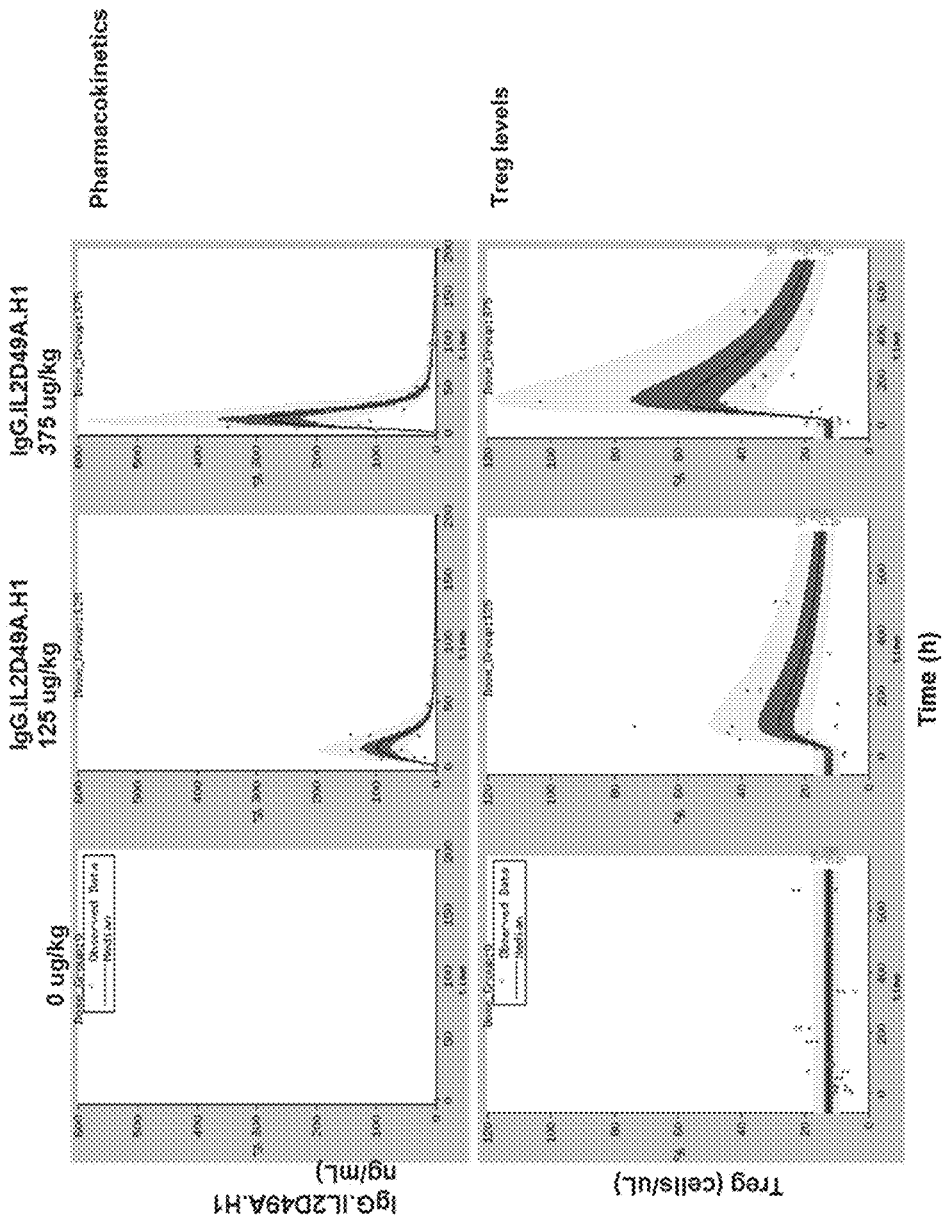
FIG. 17 shows experimental data on Treg expansion in cynomolgus monkey after a single dose of IgG.IL2D49A.H1.

IgG.IL2D49A.H1 was administered to cynomolgus monkeys in two single rising subcutaneous doses given with 4-week dosing free interval alternating between 2 dose groups (3M/group). This was followed by a 2-week multiple dose phase in two groups (3M/group) receiving 6 subcutaneous doses (every other day for two weeks) of buffer or 5 mg/kg IgG.IL2D49A.H1. Changes in lymphocyte populations assessed by flow cytometry (immunophenotyping) from the "single dose phase" (two doses given 29 days apart) are shown in FIG. 17. At the 125 and 375 µg/kg doses, 3-4 fold and up to 5.5 fold increases in absolute numbers of Treg were observed without any apparent effect on Tcon or NK cells. Maximum Treg expansion was seen on day 4 and Treg numbers return to near baseline by day 10. IgG.IL2D49A.H1 was safe and well tolerated and there were no mortalities, clinical signs or changes in body weight, food consumption, cytokine levels or clinical pathology. Furthermore no cardiovascular effects (ECG or blood pressure) were observed in the study after single dose up to 2.4 mg/kg or multiple dosing every other day for two weeks at 5 mg/kg. There was no indication of vascular leak or other CV related findings.

Example 17

Risk of Anti-drug Antibody Effects

To determine the risk of anti-drug antibody effects on GFTX3b_IL-2-H1-D49A's selective profile, signaling assays were conducted in the presence of an Fc crosslinking antibody in dose response.

Human PBMCs were resuspended in RPMI complete medium at $3\times10^6$ cells/ml, plated at $3\times10^5$ cells/well (100 µl) and rested for 2 hrs. On a separate 96-well plate, top concentrations of Proleukin, GFTX3b_IL-2-H1-D49A and GFTX3b_IL-2-H1-D49A+molar excess of goat F(ab')2 anti-human IgG, goat F(ab')2 anti-human IgG alone (Southern Biotech Cat#2042-01, Lot#J1715-PI77) and titration curves were prepared at 2X final concentration in medium. For all conditions, the top concentration of IL2 equivalent was 200 nM. The top concentration was prepared and a 10-pt dilution curve was prepared below the top concentration (with an intercalating 1:2 dilution) for Proleukin and GFTX3b_IL-2-H1-D49A. Additionally, titration curves were prepared with GFTX3b_IL-2-H1-D49A top concentration at 200 nM (equivalent IL-2) and Anti-human IgG at 0.5×, 1×, 2.5×, 5× and 10× GFTX3b_IL-2-H1-D49A based on molarity. A 10-pt, 1:10 dilution curve was prepared below the top concentration for each condition. Anti-human IgG+GFTX3b_IL-2-H1-D49A titrations were prepared and incubated for 20 minutes at room temperature prior to addition on PBMCs.

Prepared conditions (or media alone) were added to PBMCs for a final volume of 100ul/well. PBMCs were stimulated for 25 min at 37C, 5% CO2. After incubation, cells were quickly fixed, processed to be barcoded, stained for surface, permeabilized and stained for pSTAT5 and Foxp3. Cells were read on the Cytof and data analyzed with FlowJo software. Increasing concentrations of a crosslinker anti-human IgG antibody does not interfere with the selective activities of GFTX3b_IL-2-H1-D49A (FIG. 18).

Example 18

Selective Signaling Preserved in Different Autoimmune Patients

Human PBMC from autoimmune patients (Hemacare Corp) cells were rested in serum-free test media, and added to each well. On a separate plate, top concentrations of either Proleukin or GFTX3b_IL-2-H1-D49A were made and titration curves were prepared at 4× final concentration in medium. The top concentration (200 nM of IL-2 equivalent) was prepared and a 4-pt dilution curve (or 10 pt for AD) was prepared below the top concentration of either GFTX3b_IL-2-H1-D49A or native human IL-2 (Proleukin). The prepared conditions were added to the wells, and incubated for 25 min at 37C. After 25 min, cells were fixed, stained with surface markers, permeabilized and stained with intracellular antibodies (pSTAT5, Foxp3) for acquisition on Cytof (all antibodies from Fluidigm) following manufacturer's instructions. Data was analyzed using FlowJo software.

Figure 19:
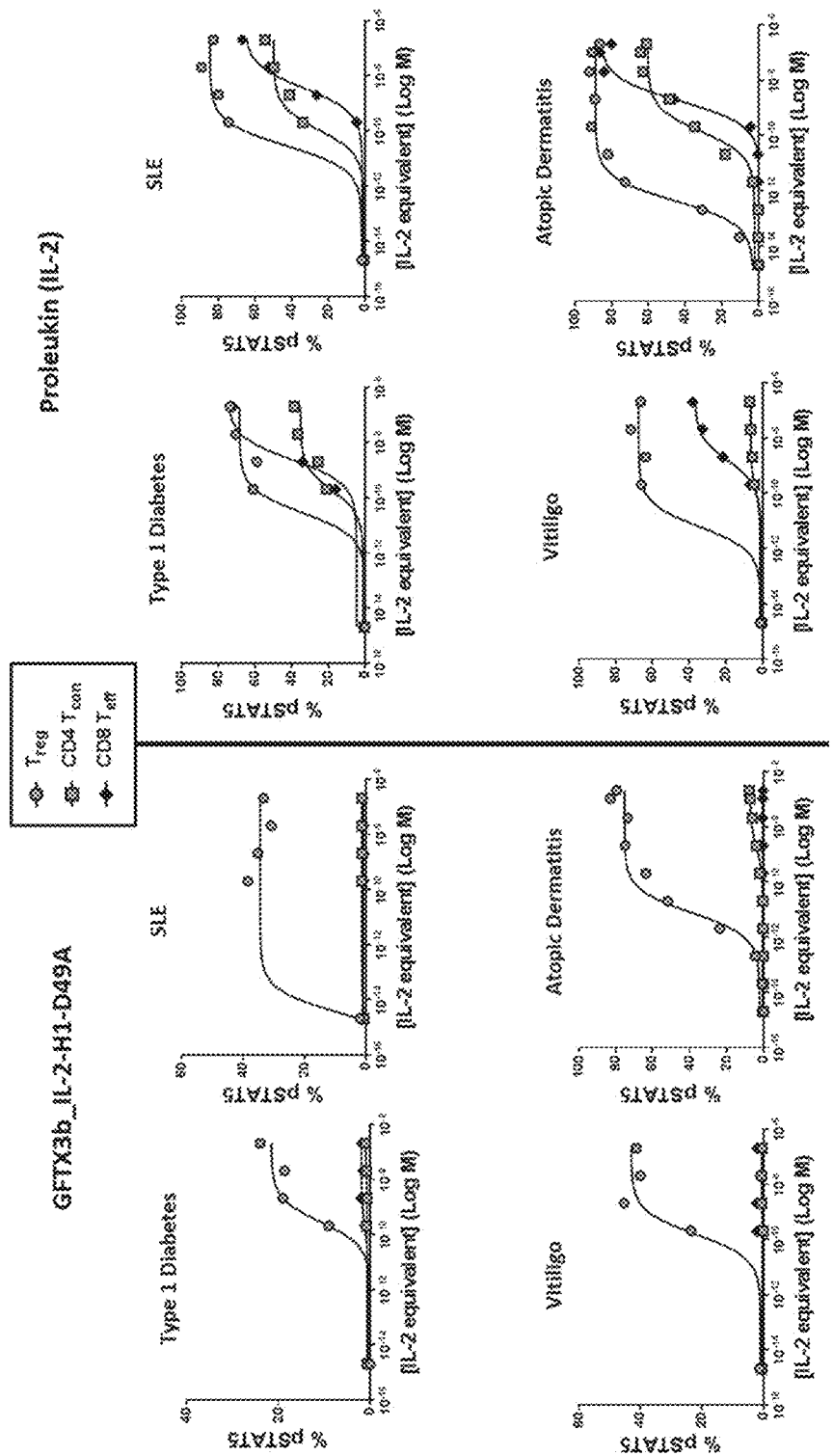
FIG. 19 shows experimental data on selective signaling in different autoimmune patients PBMC with GFTX3b_IL-2-H1-D49A.

GFTX3b_IL-2-H1-D49A was selective for $T_{regs}$ over CD4 $T_{con}$ and CD8 $T_{eff}$ in several tested autoimmune indications including type 1 diabetes, SLE, vitiligo and atopic dermatitis (FIG. 19). Potency of IL-2R signaling was reduced in $T_{con}$ and $T_{eff}$ but not $T_{regs}$ in vitro.

Example 19

Selectivity for Signaling in Tregs Over T Effector Cells in Human PBMC

PBMC cells were rested in RPMI media, and added to each well. Either IL-2 graft D49A or native human IL-2 were added to the wells, and incubated for 25 min at 37C. After 25 min, cells were fixed with 1.6% formaldehyde, washed and stained with surface markers. After 30 min at room temperature, samples were washed and re-suspended cell pellets were permeabilized with -20C methanol, washed and stained with STAT5 and DNA intercalators. Cells were run on Cytof and data analyzed with FlowJo software.

GFTX3b_IL-2D49A showed higher specificity over Proleukin for signaling on Tregs over T effectors at equimolar concentrations of IL-2 (FIG. 20).

It is understood that the examples and embodiments described herein are for illustrative purposes and that various modifications or changes in light thereof will be suggested to persons skilled in the art and are to be included within the spirit and purview of this application and scope of the appended claims. All publications, sequence accession numbers, patents, and patent applications cited herein are hereby incorporated by reference in their entirety for all purposes.

What is claimed is:

1. A method of expanding Treg cells in a patient in need thereof, comprising administering an antibody cytokine engrafted protein comprising:
   (a) a heavy chain variable region (VH) that comprises a HCDR1 of SEQ ID NO: 17, a HCDR2 of SEQ ID NO: 18, a HCDR3 of SEQ ID NO: 19; and
   (b) light chain variable region (VL) that comprises a LCDR1 of SEQ ID NO: 30, a LCDR2 of SEQ ID NO: 31, and a LCDR3 of SEQ ID NO: 32; and
   wherein the HDCR1 comprises an Interleukin 2 (IL2) molecule.

2. The method of claim 1, wherein the Treg cells are expanded and CD8 T effector cells are not expanded.

3. The method of claim 1, wherein the Treg cells are expanded and NK cells are not expanded.

4. The method of claim 1, wherein the patient has an immune related disorder.

5. The method of claim 4, wherein the immune related disorder is selected from the group consisting of: Type 1 diabetes, System Lupus Erythematosus, Vitiligo, chronic graft versus host disease (cGvHD), acute graft versus host disease, HIV-induced vasculitis, Alopecia areata, Systemic sclerosis morphoea, and primary anti-phospholipid syndrome.

6. The method of claim 1, wherein the antibody cytokine engrafted protein is administered in combination with another therapeutic agent.

7. The method of claim 6, wherein the therapeutic agent is another antibody cytokine engrafted protein.

* * * * *

SEQUENCE LISTING

<160> NUMBER OF SEQ ID NOS: 121

<210> SEQ ID NO 1
<211> LENGTH: 822
<212> TYPE: DNA
<213> ORGANISM: Homo sapiens

<400> SEQUENCE: 1

```
agttccctat cactctcttt aatcactact cacagtaacc tcaactcctg ccacaatgta      60
caggatgcaa ctcctgtctt gcattgcact aagtcttgca cttgtcacaa acagtgcacc     120
tacttcaagt tctacaaaga aaacacagct acaactggag catttactgc tggatttaca     180
gatgattttg aatggaatta ataattacaa gaatcccaaa ctcaccagga tgctcacatt     240
taagttttac atgcccaaga aggccacaga actgaaacat cttcagtgtc tagaagaaga     300
actcaaacct ctggaggaag tgctaaattt agctcaaagc aaaaactttc acttaagacc     360
cagggactta atcagcaata tcaacgtaat agttctggaa ctaaagggat ctgaaacaac     420
attcatgtgt gaatatgctg atgagacagc aaccattgta gaatttctga acagatggat     480
taccttttgt caaagcatca tctcaacact gacttgataa ttaagtgctt cccacttaaa     540
acatatcagg ccttctattt atttaaatat ttaaatttta tatttattgt tgaatgtatg     600
gtttgctacc tattgtaact attattctta atcttaaaac tataaatatg gatcttttat     660
gattcttttt gtaagcccta ggggctctaa aatggtttca cttatttatc ccaaaatatt     720
tattattatg ttgaatgtta aatatagtat ctatgtagat tggttagtaa aactatttaa     780
taaatttgat aaatataaaa aaaaaaaaaa aaaaaaaaaa aa                        822
```

<210> SEQ ID NO 2
<211> LENGTH: 153
<212> TYPE: PRT
<213> ORGANISM: Homo sapiens

<400> SEQUENCE: 2

```
Met Tyr Arg Met Gln Leu Leu Ser Cys Ile Ala Leu Ser Leu Ala Leu
1               5                   10                  15
Val Thr Asn Ser Ala Pro Thr Ser Ser Ser Thr Lys Lys Thr Gln Leu
            20                  25                  30
Gln Leu Glu His Leu Leu Leu Asp Leu Gln Met Ile Leu Asn Gly Ile
        35                  40                  45
Asn Asn Tyr Lys Asn Pro Lys Leu Thr Arg Met Leu Thr Phe Lys Phe
    50                  55                  60
Tyr Met Pro Lys Lys Ala Thr Glu Leu Lys His Leu Gln Cys Leu Glu
65                  70                  75                  80
Glu Glu Leu Lys Pro Leu Glu Glu Val Leu Asn Leu Ala Gln Ser Lys
                85                  90                  95
Asn Phe His Leu Arg Pro Arg Asp Leu Ile Ser Asn Ile Asn Val Ile
            100                 105                 110
Val Leu Glu Leu Lys Gly Ser Glu Thr Thr Phe Met Cys Glu Tyr Ala
        115                 120                 125
Asp Glu Thr Ala Thr Ile Val Glu Phe Leu Asn Arg Trp Ile Thr Phe
    130                 135                 140
Cys Gln Ser Ile Ile Ser Thr Leu Thr
145                 150
```

<210> SEQ ID NO 3
<211> LENGTH: 399
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 3

```
gcccctacct cctccagcac caagaaaacc cagctgcagc tcgaacatct gctgctggcc      60
ctgcagatga tcctgaacgg catcaacaac tacaagaacc ccaagctgac ccggatgctg     120
accttcaagt tctacatgcc caagaaggcc accgagctga acatctgca gtgcctggaa      180 gaggaactga agcccctgga agaagtgctg aacctggccc agtccaagaa cttccacctg     240
aggcctcggg acctgatctc caacatcaac gtgatcgtgc tggaactgaa gggctccgag     300
acaaccttca gtgcgagta cgccgacgag acagccacca tcgtggaatt tctgaaccgg      360
tggatcacct tctgccagtc catcatctcc accctgacc                           399
```

```
<210> SEQ ID NO 4
<211> LENGTH: 133
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 4

Ala Pro Thr Ser Ser Ser Thr Lys Lys Thr Gln Leu Gln Leu Glu His
1               5                   10                  15

Leu Leu Leu Ala Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Gln Ser Ile
        115                 120                 125

Ile Ser Thr Leu Thr
    130
```

```
<210> SEQ ID NO 5
<211> LENGTH: 399
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 5
gcccctacct cctccagcac caagaaaacc cagctgcagc tcgaacatct gctgctggcc      60
ctgcagatga tcctgaacgg catcaacaac tacaagaacc ccaagctgac ccggatgctg     120
accttcaagt tctacatgcc caagaaggcc accgagctga acatctgca gtgcctggaa      180 gaggaactga agcccctgga agaagtgctg aacctggccc agtccaagaa cttccacctg     240
aggcctcggg acctgatctc caacatcaac gtgatcgtgc tggaactgaa gggctccgag     300
acaaccttca gtgcgagta cgccgacgag acagccacca tcgtggaatt tctgaaccgg      360
tggatcacct tctcccagtc catcatctcc accctgacc                           399
```

<210> SEQ ID NO 6
<211> LENGTH: 133
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 6

```
Ala Pro Thr Ser Ser Ser Thr Lys Lys Thr Gln Leu Gln Leu Glu His
1               5                   10                  15
Leu Leu Leu Ala Leu Gln Met Ile Leu Asn Gly Ile Asn Asn Tyr Lys
            20                  25                  30
Asn Pro Lys Leu Thr Arg Met Leu Thr Phe Lys Phe Tyr Met Pro Lys
        35                  40                  45
Lys Ala Thr Glu Leu Lys His Leu Gln Cys Leu Glu Glu Glu Leu Lys
    50                  55                  60
Pro Leu Glu Glu Val Leu Asn Leu Ala Gln Ser Lys Asn Phe His Leu
65                  70                  75                  80
Arg Pro Arg Asp Leu Ile Ser Asn Ile Asn Val Ile Val Leu Glu Leu
                85                  90                  95
Lys Gly Ser Glu Thr Thr Phe Met Cys Glu Tyr Ala Asp Glu Thr Ala
            100                 105                 110
Thr Ile Val Glu Phe Leu Asn Arg Trp Ile Thr Phe Ser Gln Ser Ile
        115                 120                 125
Ile Ser Thr Leu Thr
    130
```

<210> SEQ ID NO 7
<211> LENGTH: 399
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 7

```
gcccctacct cctccagcac caagaaaacc cagctgcagc tcgaacatct gctgctggac      60
ctgcagatga tcctgaacgg catcaacaac tacaagaacc ccaagctgac ccggatgctg     120
accttcaagt tctacatgcc caagaaggcc accgagctga acatctgca gtgcctggaa     180
gaggaactga agcccctgga agaagtgctg aacctggccc agtccaagaa cttccacctg     240
aggcctcggg acctgatctc caacatcaac gtgatcgtgc tggaactgaa gggctccgag     300
acaaccttca tgtgcgagta cgccgacgag acagccacca tcgtggaatt tctgaaccgg     360
tggatcacct tctgccagtc catcatctcc accctgacc                            399
```

<210> SEQ ID NO 8
<211> LENGTH: 133
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 8

Ala Pro Thr Ser Ser Ser Thr Lys Lys Thr Gln Leu Gln Leu Glu His

```
                1               5                    10                       15
            Leu Leu Leu Asp Leu Gln Met Ile Leu Asn Gly Ile Asn Asn Tyr Lys
                            20                  25                      30

Asn Pro Lys Leu Thr Arg Met Leu Thr Phe Lys Phe Tyr Met Pro Lys
                        35                  40                  45

Lys Ala Thr Glu Leu Lys His Leu Gln Cys Leu Glu Glu Glu Leu Lys
                        50                  55                  60

Pro Leu Glu Glu Val Leu Asn Leu Ala Gln Ser Lys Asn Phe His Leu
            65                  70                  75                  80

Arg Pro Arg Asp Leu Ile Ser Asn Ile Asn Val Ile Val Leu Glu Leu
                                85                  90                  95

Lys Gly Ser Glu Thr Thr Phe Met Cys Glu Tyr Ala Asp Glu Thr Ala
                            100                 105                 110

Thr Ile Val Glu Phe Leu Asn Arg Trp Ile Thr Phe Cys Gln Ser Ile
                            115                 120                 125

Ile Ser Thr Leu Thr
                        130
```

<210> SEQ ID NO 9
<211> LENGTH: 399
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 9

```
gcccctacct cctccagcac caagaaaacc cagctgcagc tcgaacatct gctgctggac      60
ctgcagatga tcctgaacgg catcaacaac tacaagaacc ccaagctgac ccggatgctg     120
accttcaagt tctacatgcc caagaaggcc accgagctga acatctgca gtgcctggaa      180
gaggaactga gccccctgga agaagtgctg aacctggccc agtccaagaa cttccacctg     240
aggcctcggg acctgatctc caacatcaac gtgatcgtgc tggaactgaa gggctccgag     300
acaaccttca gtgcgagta cgccgacgag acagccacca tcgtggaatt tctgaaccgg     360
tggatcacct tctcccagtc catcatctcc accctgacc                            399
```

<210> SEQ ID NO 10
<211> LENGTH: 133
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 10

```
            Ala Pro Thr Ser Ser Ser Thr Lys Lys Thr Gln Leu Gln Leu Glu His
            1               5                   10                  15

Leu Leu Leu Asp Leu Gln Met Ile Leu Asn Gly Ile Asn Asn Tyr Lys
                            20                  25                  30

Asn Pro Lys Leu Thr Arg Met Leu Thr Phe Lys Phe Tyr Met Pro Lys
                        35                  40                  45

Lys Ala Thr Glu Leu Lys His Leu Gln Cys Leu Glu Glu Glu Leu Lys
                        50                  55                  60

Pro Leu Glu Glu Val Leu Asn Leu Ala Gln Ser Lys Asn Phe His Leu
            65                  70                  75                  80
```

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Ser Gln Ser Ile
        115                 120                 125

Ile Ser Thr Leu Thr
        130

<210> SEQ ID NO 11
<211> LENGTH: 145
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 11

Gly Phe Ser Leu Ala Pro Thr Ser Ser Thr Lys Lys Thr Gln Leu
1               5                   10                  15

Gln Leu Glu His Leu Leu Leu Ala Leu Gln Met Ile Leu Asn Gly Ile
            20                  25                  30

Asn Asn Tyr Lys Asn Pro Lys Leu Thr Arg Met Leu Thr Phe Lys Phe
        35                  40                  45

Tyr Met Pro Lys Lys Ala Thr Glu Leu Lys His Leu Gln Cys Leu Glu
    50                  55                  60

Glu Glu Leu Lys Pro Leu Glu Glu Val Leu Asn Leu Ala Gln Ser Lys
65                  70                  75                  80

Asn Phe His Leu Arg Pro Arg Asp Leu Ile Ser Asn Ile Asn Val Ile
                85                  90                  95

Val Leu Glu Leu Lys Gly Ser Glu Thr Thr Phe Met Cys Glu Tyr Ala
            100                 105                 110

Asp Glu Thr Ala Thr Ile Val Glu Phe Leu Asn Arg Trp Ile Thr Phe
        115                 120                 125

Cys Gln Ser Ile Ile Ser Thr Leu Thr Ser Ser Gly Met Ser Val
    130                 135                 140

Gly
145

<210> SEQ ID NO 12
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 12

Asp Ile Trp Trp Asp Asp Lys Lys Asp Tyr Asn Pro Ser Leu Lys Ser
1               5                   10                  15

<210> SEQ ID NO 13
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

```
<400> SEQUENCE: 13

Ser Met Ile Thr Asn Trp Tyr Phe Asp Val
1               5                   10

<210> SEQ ID NO 14
<211> LENGTH: 141
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 14

Ala Pro Thr Ser Ser Ser Thr Lys Lys Thr Gln Leu Gln Leu Glu His
1               5                   10                  15

Leu Leu Leu Ala Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Gln Ser Ile
        115                 120                 125

Ile Ser Thr Leu Thr Ser Thr Ser Gly Met Ser Val Gly
    130                 135                 140

<210> SEQ ID NO 15
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 15

Asp Ile Trp Trp Asp Asp Lys Lys Asp Tyr Asn Pro Ser Leu Lys Ser
1               5                   10                  15

<210> SEQ ID NO 16
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 16

Ser Met Ile Thr Asn Trp Tyr Phe Asp Val
1               5                   10

<210> SEQ ID NO 17
<211> LENGTH: 142
<212> TYPE: PRT
<213> ORGANISM: Artificial Sequence
```

```
<220> FEATURE:
<221> NAME/KEY: source
<223> OTHER INFORMATION: /note="Description of Artificial Sequence:
      Synthetic polypeptide"

<400> SEQUENCE: 17

Gly Phe Ser Leu Ala Pro Thr Ser Ser Thr Lys Lys Thr Gln Leu
1               5                   10                  15

Gln Leu Glu His Leu Leu Ala Leu Gln Met Ile Leu Asn Gly Ile
            20                  25                  30

Asn Asn Tyr Lys Asn Pro Lys Leu Thr Arg Met Leu Thr Phe Lys Phe
            35                  40                  45

Tyr Met Pro Lys Lys Ala Thr Glu Leu Lys His Leu Gln Cys Leu Glu
    50                  55                  60

Glu Leu Lys Pro Leu Glu Glu Val Leu Asn Leu Ala Gln Ser Lys
65                  70                  75                  80

Asn Phe His Leu Arg Pro Arg Asp Leu Ile Ser Asn Ile Asn Val Ile
                85                  90                  95

Val Leu Glu Leu Lys Gly Ser Glu Thr Thr Phe Met Cys Glu Tyr Ala
                100                 105                 110

Asp Glu Thr Ala Thr Ile Val Glu Phe Leu Asn Arg Trp Ile Thr Phe
            115                 120                 125

Cys Gln Ser Ile Ile Ser Thr Leu Thr Ser Thr Ser Gly Met
    130                 135                 140

<210> SEQ ID NO 18
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 18

Trp Trp Asp Asp Lys
1               5

<210> SEQ ID NO 19
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 19

Ser Met Ile Thr Asn Trp Tyr Phe Asp Val
1               5                   10

<210> SEQ ID NO 20
<211> LENGTH: 253
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 20

Gln Val Thr Leu Arg Glu Ser Gly Pro Ala Leu Val Lys Pro Thr Gln
1               5                   10                  15
```

```
Thr Leu Thr Leu Thr Cys Thr Phe Ser Gly Phe Ser Leu Ala Pro Thr
             20                  25                  30

Ser Ser Ser Thr Lys Lys Thr Gln Leu Gln Leu Glu His Leu Leu Leu
         35                  40                  45

Ala Leu Gln Met Ile Leu Asn Gly Ile Asn Asn Tyr Lys Asn Pro Lys
     50                  55                  60

Leu Thr Arg Met Leu Thr Phe Lys Phe Tyr Met Pro Lys Lys Ala Thr
 65                  70                  75                  80

Glu Leu Lys His Leu Gln Cys Leu Glu Glu Leu Lys Pro Leu Glu
                 85                  90                  95

Glu Val Leu Asn Leu Ala Gln Ser Lys Asn Phe His Leu Arg Pro Arg
            100                 105                 110

Asp Leu Ile Ser Asn Ile Asn Val Ile Val Leu Glu Leu Lys Gly Ser
            115                 120                 125

Glu Thr Thr Phe Met Cys Glu Tyr Ala Asp Glu Thr Ala Thr Ile Val
        130                 135                 140

Glu Phe Leu Asn Arg Trp Ile Thr Phe Cys Gln Ser Ile Ile Ser Thr
145                 150                 155                 160

Leu Thr Ser Thr Ser Gly Met Ser Val Gly Trp Ile Arg Gln Pro Pro
                165                 170                 175

Gly Lys Ala Leu Glu Trp Leu Ala Asp Ile Trp Trp Asp Asp Lys Lys
            180                 185                 190

Asp Tyr Asn Pro Ser Leu Lys Ser Arg Leu Thr Ile Ser Lys Asp Thr
            195                 200                 205

Ser Lys Asn Gln Val Val Leu Lys Val Thr Asn Met Asp Pro Ala Asp
        210                 215                 220

Thr Ala Thr Tyr Tyr Cys Ala Arg Ser Met Ile Thr Asn Trp Tyr Phe
225                 230                 235                 240

Asp Val Trp Gly Ala Gly Thr Thr Val Thr Val Ser Ser
                245                 250
```

<210> SEQ ID NO 21
<211> LENGTH: 759
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 21

```
caagtcacac tgcgtgaaag cggccctgcc ctggtcaagc ccacccagac cctgaccctg     60
acctgcacct tctccggctt cagcctggcc cctacctcct ccagcaccaa gaaaacccag    120
ctgcagctcg aacatctgct gctggccctg cagatgatcc tgaacggcat caacaactac    180
aagaacccca gctgacccg dgatgctgacc ttcaagttct acatgcccaa gaaggccacc    240
gagctgaaac atctgcagtg cctggaagag gaactgaagc ccctggaaga agtgctgaac    300
ctggcccagt ccaagaactt ccacctgagg cctcgggacc tgatctccaa catcaacgtg    360
atcgtgctgg aactgaaggg ctccgagaca accttcatgt gcgagtacgc cgacgagaca    420
gccaccatcg tggaatttct gaaccggtgg atcaccttct gccagtccat catctccacc    480
ctgacctcca cctccggcat gtccgtgggc tggatccggc agcctcctgg caaggccctg    540
gagtggctgg ccgacatttg tgggacgac aagaaggact acaacccag cctgaagtcc    600 cggctgacca tctccaagga cacctccaag aaccagtgg tgctgaaagt gaccaacatg    660
```

-continued

```
gaccccgccg acaccgccac ctactactgc gcccggtcca tgatcaccaa ctggtacttc      720
gacgtgtggg gcgctggcac caccgtgacc gtgtcctct                              759
```

<210> SEQ ID NO 22
<211> LENGTH: 583
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 22

```
Gln Val Thr Leu Arg Glu Ser Gly Pro Ala Leu Val Lys Pro Thr Gln
1               5                   10                  15

Thr Leu Thr Leu Thr Cys Thr Phe Ser Gly Phe Ser Leu Ala Pro Thr
            20                  25                  30

Ser Ser Ser Thr Lys Lys Thr Gln Leu Gln Leu Glu His Leu Leu Leu
        35                  40                  45

Ala Leu Gln Met Ile Leu Asn Gly Ile Asn Asn Tyr Lys Asn Pro Lys
    50                  55                  60

Leu Thr Arg Met Leu Thr Phe Lys Phe Tyr Met Pro Lys Lys Ala Thr
65                  70                  75                  80

Glu Leu Lys His Leu Gln Cys Leu Glu Glu Leu Lys Pro Leu Glu
                85                  90                  95

Glu Val Leu Asn Leu Ala Gln Ser Lys Asn Phe His Leu Arg Pro Arg
            100                 105                 110

Asp Leu Ile Ser Asn Ile Asn Val Ile Val Leu Glu Leu Lys Gly Ser
        115                 120                 125

Glu Thr Thr Phe Met Cys Glu Tyr Ala Asp Glu Thr Ala Thr Ile Val
    130                 135                 140

Glu Phe Leu Asn Arg Trp Ile Thr Phe Cys Gln Ser Ile Ile Ser Thr
145                 150                 155                 160

Leu Thr Ser Thr Ser Gly Met Ser Val Gly Trp Ile Arg Gln Pro Pro
                165                 170                 175

Gly Lys Ala Leu Glu Trp Leu Ala Asp Ile Trp Trp Asp Asp Lys Lys
            180                 185                 190

Asp Tyr Asn Pro Ser Leu Lys Ser Arg Leu Thr Ile Ser Lys Asp Thr
        195                 200                 205

Ser Lys Asn Gln Val Val Leu Lys Val Thr Asn Met Asp Pro Ala Asp
    210                 215                 220

Thr Ala Thr Tyr Tyr Cys Ala Arg Ser Met Ile Thr Asn Trp Tyr Phe
225                 230                 235                 240

Asp Val Trp Gly Ala Gly Thr Thr Val Thr Val Ser Ser Ala Ser Thr
                245                 250                 255

Lys Gly Pro Ser Val Phe Pro Leu Ala Pro Ser Ser Lys Ser Thr Ser
            260                 265                 270

Gly Gly Thr Ala Ala Leu Gly Cys Leu Val Lys Asp Tyr Phe Pro Glu
        275                 280                 285

Pro Val Thr Val Ser Trp Asn Ser Gly Ala Leu Thr Ser Gly Val His
    290                 295                 300

Thr Phe Pro Ala Val Leu Gln Ser Ser Gly Leu Tyr Ser Leu Ser Ser
305                 310                 315                 320

Val Val Thr Val Pro Ser Ser Ser Leu Gly Thr Gln Thr Tyr Ile Cys
                325                 330                 335
```

```
Asn Val Asn His Lys Pro Ser Asn Thr Lys Val Asp Lys Arg Val Glu
                340                 345                 350
Pro Lys Ser Cys Asp Lys Thr His Thr Cys Pro Pro Cys Pro Ala Pro
            355                 360                 365
Glu Leu Leu Gly Gly Pro Ser Val Phe Leu Phe Pro Pro Lys Pro Lys
        370                 375                 380
Asp Thr Leu Met Ile Ser Arg Thr Pro Glu Val Thr Cys Val Val Val
385                 390                 395                 400
Ala Val Ser His Glu Asp Pro Glu Val Lys Phe Asn Trp Tyr Val Asp
                405                 410                 415
Gly Val Glu Val His Asn Ala Lys Thr Lys Pro Arg Glu Glu Gln Tyr
            420                 425                 430
Asn Ser Thr Tyr Arg Val Val Ser Val Leu Thr Val Leu His Gln Asp
        435                 440                 445
Trp Leu Asn Gly Lys Glu Tyr Lys Cys Lys Val Ser Asn Lys Ala Leu
    450                 455                 460
Ala Ala Pro Ile Glu Lys Thr Ile Ser Lys Ala Lys Gly Gln Pro Arg
465                 470                 475                 480
Glu Pro Gln Val Tyr Thr Leu Pro Pro Ser Arg Glu Glu Met Thr Lys
                485                 490                 495
Asn Gln Val Ser Leu Thr Cys Leu Val Lys Gly Phe Tyr Pro Ser Asp
            500                 505                 510
Ile Ala Val Glu Trp Glu Ser Asn Gly Gln Pro Glu Asn Asn Tyr Lys
        515                 520                 525
Thr Thr Pro Pro Val Leu Asp Ser Asp Gly Ser Phe Phe Leu Tyr Ser
    530                 535                 540
Lys Leu Thr Val Asp Lys Ser Arg Trp Gln Gln Gly Asn Val Phe Ser
545                 550                 555                 560
Cys Ser Val Met His Glu Ala Leu His Asn His Tyr Thr Gln Lys Ser
                565                 570                 575
Leu Ser Leu Ser Pro Gly Lys
            580
```

<210> SEQ ID NO 23
<211> LENGTH: 1749
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 23

```
caagtcacac tgcgtgaaag cggccctgcc ctggtcaagc ccacccagac cctgaccctg      60
acctgcacct tctccggctt cagcctggcc cctacctcct ccagcaccaa gaaaacccag     120
ctgcagctcg acatctgctg ctggccctg cagatgatcc tgaacggcat caacaactac     180
aagaacccca agctgacccg gatgctgacc ttcaagttct acatgcccaa gaaggccacc     240
gagctgaaac atctgcagtg cctggaagag gaactgaagc ccctggaaga gtgctgaac      300
ctggcccagt ccaagaactt ccacctgagg cctcgggacc tgatctccaa catcaacgtg     360
atcgtgctgg aactgaaggg ctccgagaca accttcatgt gcgagtacgc cgacgagaca     420
gccaccatcg tggaatttct gaaccggtgg atcaccttct gccagtccat catctccacc     480
ctgacctcca cctccggcat gtccgtgggc tggatccggc agcctcctgg caaggccctg     540
gagtggctgg ccgacatttg gtgggacgac aagaaggact acaaccccag cctgaagtcc     600
```

```
cggctgacca tctccaagga cacctccaag aaccaagtgg tgctgaaagt gaccaacatg    660
gaccccgccg acaccgccac ctactactgc gcccggtcca tgatcaccaa ctggtacttc    720
gacgtgtggg gcgctggcac caccgtgacc gtgtcctctg ctagcaccaa gggccccctcc   780 gtgttccctc tggccccttc cagcaagtct acctccggcg cacagctgc tctgggctgc     840 ctggtcaagg actacttccc tgagcctgtg acagtgtcct ggaactctgg cgccctgacc    900
tctggcgtgc acaccttccc tgccgtgctg cagtcctccg gcctgtactc cctgtcctcc    960
gtggtcacag tgccttcaag cagcctgggc acccagacct atatctgcaa cgtgaaccac   1020
aagccttcca acaccaaggt ggacaagcgg gtggagccta agtcctgcga caagacccac   1080
acctgtcctc cctgccctgc tcctgaactg ctgggcggcc cttctgtgtt cctgttccct   1140
ccaaagccca aggacaccct gatgatctcc cggacccctg aagtgacctg cgtggtggtg   1200
gccgtgtccc acgaggatcc tgaagtgaag ttcaattggt acgtggacgg cgtggaggtg   1260
cacaacgcca agaccaagcc tcgggaggaa cagtacaact ccacctaccg ggtggtgtcc   1320
gtgctgaccg tgctgcacca ggactggctg aacggcaaag agtacaagtg caaagtctcc   1380
aacaaggccc tggccgcccc tatcgaaaag acaatctcca aggccaaggg ccagcctagg   1440
gaaccccagg tgtacaccct gccacccagc cgggaggaaa tgaccaagaa ccaggtgtcc   1500
ctgacctgtc tggtcaaggg cttctaccct tccgatatcg ccgtggagtg ggagtctaac   1560
ggccagcctg agaacaacta caagaccacc cctcctgtgc tggactccga cggctccttc   1620
ttcctgtact ccaaactgac cgtggacaag tcccggtggc agcagggcaa cgtgttctcc   1680
tgctccgtga tgcacgaggc cctgcacaac cactacaccc agaagtccct gtccctgtct   1740
cccggcaag                                                           1749
```

<210> SEQ ID NO 24
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 24

Lys Ala Gln Leu Ser Val Gly Tyr Met His
1               5                   10

<210> SEQ ID NO 25
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 25

Asp Thr Ser Lys Leu Ala Ser
1               5

<210> SEQ ID NO 26
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:

Synthetic peptide"

<400> SEQUENCE: 26

Phe Gln Gly Ser Gly Tyr Pro Phe Thr
1               5

<210> SEQ ID NO 27
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 27

Lys Ala Gln Leu Ser Val Gly Tyr Met His
1               5                   10

<210> SEQ ID NO 28
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 28

Asp Thr Ser Lys Leu Ala Ser
1               5

<210> SEQ ID NO 29
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 29

Phe Gln Gly Ser Gly Tyr Pro Phe Thr
1               5

<210> SEQ ID NO 30
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 30

Gln Leu Ser Val Gly Tyr
1               5

<210> SEQ ID NO 31
<211> LENGTH: 3
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 31

Asp Thr Ser
1

<210> SEQ ID NO 32
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 32

Gly Ser Gly Tyr Pro Phe
1               5

<210> SEQ ID NO 33
<211> LENGTH: 106
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 33

Asp Ile Gln Met Thr Gln Ser Pro Ser Thr Leu Ser Ala Ser Val Gly
1               5                   10                  15

Asp Arg Val Thr Ile Thr Cys Lys Ala Gln Leu Ser Val Gly Tyr Met
            20                  25                  30

His Trp Tyr Gln Gln Lys Pro Gly Lys Ala Pro Lys Leu Leu Ile Tyr
        35                  40                  45

Asp Thr Ser Lys Leu Ala Ser Gly Val Pro Ser Arg Phe Ser Gly Ser
    50                  55                  60

Gly Ser Gly Thr Glu Phe Thr Leu Thr Ile Ser Ser Leu Gln Pro Asp
65                  70                  75                  80

Asp Phe Ala Thr Tyr Tyr Cys Phe Gln Gly Ser Gly Tyr Pro Phe Thr
                85                  90                  95

Phe Gly Gly Gly Thr Lys Leu Glu Ile Lys
            100                 105

<210> SEQ ID NO 34
<211> LENGTH: 318
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 34
gacatccaga tgacccagag cccctccacc ctgtccgcct ccgtgggcga cagagtgacc      60
atcacttgca aggcccagct gtccgtgggc tacatgcact ggtatcagca gaagcccggc     120
aaggccccta agctgctgat ctacgacacc tccaagctgg cctccggcgt gccctccaga     180
ttctccggct ctggctccgg caccgagttc accctgacca tctccagcct gcagcccgac     240
gacttcgcca cctactactg ttttcaaggc tccggctacc ccttcacctt cggcggaggc     300
accaagctgg aaatcaag                                                  318

<210> SEQ ID NO 35
<211> LENGTH: 213
<212> TYPE: PRT

<213> ORGANISM: Artificial Sequence
<220> FEATURE:
<221> NAME/KEY: source
<223> OTHER INFORMATION: /note="Description of Artificial Sequence:
    Synthetic polypeptide"

<400> SEQUENCE: 35

```
Asp Ile Gln Met Thr Gln Ser Pro Ser Thr Leu Ser Ala Ser Val Gly
1               5                   10                  15

Asp Arg Val Thr Ile Thr Cys Lys Ala Gln Leu Ser Val Gly Tyr Met
            20                  25                  30

His Trp Tyr Gln Gln Lys Pro Gly Lys Ala Pro Lys Leu Leu Ile Tyr
        35                  40                  45

Asp Thr Ser Lys Leu Ala Ser Gly Val Pro Ser Arg Phe Ser Gly Ser
    50                  55                  60

Gly Ser Gly Thr Glu Phe Thr Leu Thr Ile Ser Ser Leu Gln Pro Asp
65                  70                  75                  80

Asp Phe Ala Thr Tyr Tyr Cys Phe Gln Gly Ser Gly Tyr Pro Phe Thr
                85                  90                  95

Phe Gly Gly Gly Thr Lys Leu Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210
```

<210> SEQ ID NO 36
<211> LENGTH: 639
<212> TYPE: DNA
<213> ORGANISM: Artificial Sequence
<220> FEATURE:
<221> NAME/KEY: source
<223> OTHER INFORMATION: /note="Description of Artificial Sequence:
    Synthetic polynucleotide"

<400> SEQUENCE: 36

```
gacatccaga tgacccagag ccctccacc  ctgtccgcct ccgtgggcga cagagtgacc      60
atcacttgca aggcccagct gtccgtgggc tacatgcact ggtatcagca gaagcccggc     120
aaggccccta agctgctgat ctacgacacc tccaagctgg cctccggcgt gccctccaga     180
ttctccggct ctggctccgg caccgagttc accctgacca tctccagcct gcagcccgac     240
gacttcgcca cctactactg ttttcaaggc tccggctacc ccttcacctt cggcggaggc     300
accaagctgg aaatcaagcg tacggtggcc gctcccagcg tgttcatctt cccccccagc     360
gacgagcagc tgaagagcgg caccgccagc gtggtgtgcc tgctgaacaa cttctacccc     420
cgggaggcca aggtgcagtg gaaggtggac aacgccctgc agagcggcaa cagccaggag     480
agcgtcaccg agcaggacag caaggactcc acctacagcc tgagcagcac cctgaccctg     540
```

```
agcaaggccg actacgagaa gcataaggtg tacgcctgcg aggtgaccca ccagggcctg    600
tccagccccg tgaccaagag cttcaacagg ggcgagtgc                          639
```

<210> SEQ ID NO 37
<211> LENGTH: 145
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 37

```
Gly Phe Ser Leu Ala Pro Thr Ser Ser Thr Lys Lys Thr Gln Leu
1               5                   10                  15

Gln Leu Glu His Leu Leu Leu Ala Leu Gln Met Ile Leu Asn Gly Ile
            20                  25                  30

Asn Asn Tyr Lys Asn Pro Lys Leu Thr Arg Met Leu Thr Phe Lys Phe
        35                  40                  45

Tyr Met Pro Lys Lys Ala Thr Glu Leu Lys His Leu Gln Cys Leu Glu
    50                  55                  60

Glu Glu Leu Lys Pro Leu Glu Glu Val Leu Asn Leu Ala Gln Ser Lys
65                  70                  75                  80

Asn Phe His Leu Arg Pro Arg Asp Leu Ile Ser Asn Ile Asn Val Ile
                85                  90                  95

Val Leu Glu Leu Lys Gly Ser Glu Thr Thr Phe Met Cys Glu Tyr Ala
            100                 105                 110

Asp Glu Thr Ala Thr Ile Val Glu Phe Leu Asn Arg Trp Ile Thr Phe
        115                 120                 125

Ser Gln Ser Ile Ile Ser Thr Leu Thr Ser Thr Ser Gly Met Ser Val
    130                 135                 140

Gly
145
```

<210> SEQ ID NO 38
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 38

```
Asp Ile Trp Trp Asp Asp Lys Lys Asp Tyr Asn Pro Ser Leu Lys Ser
1               5                   10                  15
```

<210> SEQ ID NO 39
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 39

```
Ser Met Ile Thr Asn Trp Tyr Phe Asp Val
1               5                   10
```

<210> SEQ ID NO 40

```
<211> LENGTH: 141
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 40

Ala Pro Thr Ser Ser Ser Thr Lys Lys Thr Gln Leu Gln Leu Glu His
1               5                   10                  15

Leu Leu Leu Ala Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Ser Gln Ser Ile
        115                 120                 125

Ile Ser Thr Leu Thr Ser Thr Ser Gly Met Ser Val Gly
            130                 135                 140

<210> SEQ ID NO 41
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 41

Asp Ile Trp Trp Asp Asp Lys Lys Asp Tyr Asn Pro Ser Leu Lys Ser
1               5                   10                  15

<210> SEQ ID NO 42
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 42

Ser Met Ile Thr Asn Trp Tyr Phe Asp Val
1               5                   10

<210> SEQ ID NO 43
<211> LENGTH: 142
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 43
```

```
Gly Phe Ser Leu Ala Pro Thr Ser Ser Thr Lys Lys Thr Gln Leu
1               5                   10                  15

Gln Leu Glu His Leu Leu Ala Leu Gln Met Ile Leu Asn Gly Ile
            20                  25                  30

Asn Asn Tyr Lys Asn Pro Lys Leu Thr Arg Met Leu Thr Phe Lys Phe
            35                  40                  45

Tyr Met Pro Lys Lys Ala Thr Glu Leu Lys His Leu Gln Cys Leu Glu
        50                  55                  60

Glu Glu Leu Lys Pro Leu Glu Glu Val Leu Asn Leu Ala Gln Ser Lys
65                  70                  75                  80

Asn Phe His Leu Arg Pro Arg Asp Leu Ile Ser Asn Ile Asn Val Ile
                85                  90                  95

Val Leu Glu Leu Lys Gly Ser Glu Thr Thr Phe Met Cys Glu Tyr Ala
                100                 105                 110

Asp Glu Thr Ala Thr Ile Val Glu Phe Leu Asn Arg Trp Ile Thr Phe
            115                 120                 125

Ser Gln Ser Ile Ile Ser Thr Leu Thr Ser Thr Ser Gly Met
    130                 135                 140
```

```
<210> SEQ ID NO 44
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 44

Trp Trp Asp Asp Lys
1               5
```

```
<210> SEQ ID NO 45
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 45

Ser Met Ile Thr Asn Trp Tyr Phe Asp Val
1               5                   10
```

```
<210> SEQ ID NO 46
<211> LENGTH: 253
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 46

Gln Val Thr Leu Arg Glu Ser Gly Pro Ala Leu Val Lys Pro Thr Gln
1               5                   10                  15

Thr Leu Thr Leu Thr Cys Thr Phe Ser Gly Phe Ser Leu Ala Pro Thr
            20                  25                  30

Ser Ser Ser Thr Lys Lys Thr Gln Leu Gln Leu Glu His Leu Leu Leu
        35                  40                  45

Ala Leu Gln Met Ile Leu Asn Gly Ile Asn Asn Tyr Lys Asn Pro Lys
```

```
            50                  55                  60
Leu Thr Arg Met Leu Thr Phe Lys Phe Tyr Met Pro Lys Lys Ala Thr
 65                  70                  75                  80

Glu Leu Lys His Leu Gln Cys Leu Glu Glu Glu Leu Lys Pro Leu Glu
                 85                  90                  95

Glu Val Leu Asn Leu Ala Gln Ser Lys Asn Phe His Leu Arg Pro Arg
                100                 105                 110

Asp Leu Ile Ser Asn Ile Asn Val Ile Val Leu Glu Leu Lys Gly Ser
                115                 120                 125

Glu Thr Thr Phe Met Cys Glu Tyr Ala Asp Glu Thr Ala Thr Ile Val
                130                 135                 140

Glu Phe Leu Asn Arg Trp Ile Thr Phe Ser Gln Ser Ile Ile Ser Thr
145                 150                 155                 160

Leu Thr Ser Thr Ser Gly Met Ser Val Gly Trp Ile Arg Gln Pro Pro
                165                 170                 175

Gly Lys Ala Leu Glu Trp Leu Ala Asp Ile Trp Trp Asp Asp Lys Lys
                180                 185                 190

Asp Tyr Asn Pro Ser Leu Lys Ser Arg Leu Thr Ile Ser Lys Asp Thr
                195                 200                 205

Ser Lys Asn Gln Val Val Leu Lys Val Thr Asn Met Asp Pro Ala Asp
                210                 215                 220

Thr Ala Thr Tyr Tyr Cys Ala Arg Ser Met Ile Thr Asn Trp Tyr Phe
225                 230                 235                 240

Asp Val Trp Gly Ala Gly Thr Thr Val Thr Val Ser Ser
                245                 250

<210> SEQ ID NO 47
<211> LENGTH: 759
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 47
caagtcacac tgcgtgaaag cggccctgcc ctggtcaagc ccacccagac cctgaccctg      60
acctgcacct tctccggctt cagcctggcc cctacctcct ccagcaccaa gaaaacccag     120
ctgcagctcg aacatctgct gctggccctg cagatgatcc tgaacggcat caacaactac     180
aagaacccca gcctgacccg gatgctgacc ttcaagttct acatgcccaa gaaggccacc     240
gagctgaaac atctgcagtg cctggaagag gaactgaagc ccctggaaga gtgctgaac      300 ctggcccagt ccaagaactt ccacctgagg cctcgggacc tgatctccaa catcaacgtg     360
atcgtgctgg aactgaaggg ctccgagaca accttcatgt gcgagtacgc cgacgagaca     420
gccaccatcg tggaatttct gaaccggtgg atcaccttct cccagtccat catctccacc     480
ctgacctcca cctccggcat gtccgtgggc tggatccggc agcctcctgg caaggccctg     540
gagtggctgg ccgacatttg tgggacgac aagaaggact acaacccag cctgaagtcc      600 cggctgacca tctccaagga cacctccaag aaccaagtgg tgctgaaagt gaccaacatg     660
gaccccgccg acaccgccac ctactactgc gcccggtcca tgatcaccaa ctggtacttc     720
gacgtgtggg gcgctggcac caccgtgacc gtgtcctct                            759

<210> SEQ ID NO 48
<211> LENGTH: 583
```

<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 48

```
Gln Val Thr Leu Arg Glu Ser Gly Pro Ala Leu Val Lys Pro Thr Gln
1               5                   10                  15

Thr Leu Thr Leu Thr Cys Thr Phe Ser Gly Phe Ser Leu Ala Pro Thr
            20                  25                  30

Ser Ser Ser Thr Lys Lys Thr Gln Leu Gln Leu Glu His Leu Leu Leu
        35                  40                  45

Ala Leu Gln Met Ile Leu Asn Gly Ile Asn Asn Tyr Lys Asn Pro Lys
    50                  55                  60

Leu Thr Arg Met Leu Thr Phe Lys Phe Tyr Met Pro Lys Lys Ala Thr
65                  70                  75                  80

Glu Leu Lys His Leu Gln Cys Leu Glu Glu Leu Lys Pro Leu Glu
                85                  90                  95

Glu Val Leu Asn Leu Ala Gln Ser Lys Asn Phe His Leu Arg Pro Arg
            100                 105                 110

Asp Leu Ile Ser Asn Ile Asn Val Ile Val Leu Glu Leu Lys Gly Ser
        115                 120                 125

Glu Thr Thr Phe Met Cys Glu Tyr Ala Asp Glu Thr Ala Thr Ile Val
    130                 135                 140

Glu Phe Leu Asn Arg Trp Ile Thr Phe Ser Gln Ser Ile Ile Ser Thr
145                 150                 155                 160

Leu Thr Ser Thr Ser Gly Met Ser Val Gly Trp Ile Arg Gln Pro Pro
                165                 170                 175

Gly Lys Ala Leu Glu Trp Leu Ala Asp Ile Trp Trp Asp Asp Lys Lys
            180                 185                 190

Asp Tyr Asn Pro Ser Leu Lys Ser Arg Leu Thr Ile Ser Lys Asp Thr
        195                 200                 205

Ser Lys Asn Gln Val Val Leu Lys Val Thr Asn Met Asp Pro Ala Asp
    210                 215                 220

Thr Ala Thr Tyr Tyr Cys Ala Arg Ser Met Ile Thr Asn Trp Tyr Phe
225                 230                 235                 240

Asp Val Trp Gly Ala Gly Thr Thr Val Thr Val Ser Ser Ala Ser Thr
                245                 250                 255

Lys Gly Pro Ser Val Phe Pro Leu Ala Pro Ser Ser Lys Ser Thr Ser
            260                 265                 270

Gly Gly Thr Ala Ala Leu Gly Cys Leu Val Lys Asp Tyr Phe Pro Glu
        275                 280                 285

Pro Val Thr Val Ser Trp Asn Ser Gly Ala Leu Thr Ser Gly Val His
    290                 295                 300

Thr Phe Pro Ala Val Leu Gln Ser Ser Gly Leu Tyr Ser Leu Ser Ser
305                 310                 315                 320

Val Val Thr Val Pro Ser Ser Ser Leu Gly Thr Gln Thr Tyr Ile Cys
                325                 330                 335

Asn Val Asn His Lys Pro Ser Asn Thr Lys Val Asp Lys Arg Val Glu
            340                 345                 350

Pro Lys Ser Cys Asp Lys Thr His Thr Cys Pro Pro Cys Pro Ala Pro
        355                 360                 365

Glu Leu Leu Gly Gly Pro Ser Val Phe Leu Phe Pro Pro Lys Pro Lys
```

```
                370             375              380
Asp Thr Leu Met Ile Ser Arg Thr Pro Glu Val Thr Cys Val Val
385                 390                 395                 400

Ala Val Ser His Glu Asp Pro Glu Val Lys Phe Asn Trp Tyr Val Asp
                405                 410                 415

Gly Val Glu Val His Asn Ala Lys Thr Lys Pro Arg Glu Glu Gln Tyr
                420                 425                 430

Asn Ser Thr Tyr Arg Val Val Ser Val Leu Thr Val Leu His Gln Asp
            435                 440                 445

Trp Leu Asn Gly Lys Glu Tyr Lys Cys Lys Val Ser Asn Lys Ala Leu
    450                 455                 460

Ala Ala Pro Ile Glu Lys Thr Ile Ser Lys Ala Lys Gly Gln Pro Arg
465                 470                 475                 480

Glu Pro Gln Val Tyr Thr Leu Pro Pro Ser Arg Glu Glu Met Thr Lys
                485                 490                 495

Asn Gln Val Ser Leu Thr Cys Leu Val Lys Gly Phe Tyr Pro Ser Asp
                500                 505                 510

Ile Ala Val Glu Trp Glu Ser Asn Gly Gln Pro Glu Asn Asn Tyr Lys
            515                 520                 525

Thr Thr Pro Pro Val Leu Asp Ser Asp Gly Ser Phe Phe Leu Tyr Ser
    530                 535                 540

Lys Leu Thr Val Asp Lys Ser Arg Trp Gln Gln Gly Asn Val Phe Ser
545                 550                 555                 560

Cys Ser Val Met His Glu Ala Leu His Asn His Tyr Thr Gln Lys Ser
                565                 570                 575

Leu Ser Leu Ser Pro Gly Lys
            580

<210> SEQ ID NO 49
<211> LENGTH: 1749
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 49
caagtcacac tgcgtgaaag cggccctgcc ctggtcaagc ccacccagac cctgaccctg      60
acctgcacct tctccggctt cagcctggcc cctacctcct ccagcaccaa gaaaacccag     120
ctgcagctcg aacatctgct gctggccctg cagatgatcc tgaacggcat caacaactac     180
aagaacccca gctgacccg gatgctgacc ttcaagttct acatgcccaa gaaggccacc     240
gagctgaaac atctgcagtg cctggaagag gaactgaagc ccctggaaga agtgctgaac     300
ctggcccagt ccaagaactt ccacctgagg cctcgggacc tgatctccaa catcaacgtg     360
atcgtgctgg aactgaaggg ctccgagaca accttcatgt gcgagtacgc cgacgagaca     420
gccaccatcg tggaatttct gaaccggtgg atcaccttct cccagtccat catctccacc     480
ctgacctcca cctccggcat gtccgtgggc tggatccggc agcctcctgg caaggccctg     540
gagtggctgg ccgacatttg gtgggacgac aagaaggact acaacccag cctgaagtcc     600 cggctgacca tctccaagga cacctccaag aaccaagtgg tgctgaaagt gaccaacatg     660
gaccccgccg acaccgccac ctactactgc gcccggtcca tgatcaccaa ctggtacttc     720
gacgtgtggg gcgctggcac caccgtgacc gtgtcctctg ctagcaccaa gggcccctcc     780
```

```
gtgttccctc tggccccttc cagcaagtct acctccggcg gcacagctgc tctgggctgc    840
ctggtcaagg actacttccc tgagcctgtg acagtgtcct ggaactctgg cgccctgacc    900
tctggcgtgc acaccttccc tgccgtgctg cagtcctccg gcctgtactc cctgtcctcc    960
gtggtcacag tgccttcaag cagcctgggc acccagacct atatctgcaa cgtgaaccac   1020
aagccttcca acaccaaggt ggacaagcgg gtggagccta agtcctgcga caagacccac   1080
acctgtcctc cctgccctgc tcctgaactg ctgggcggcc cttctgtgtt cctgttccct   1140
ccaaagccca aggacaccct gatgatctcc cggacccctg aagtgacctg cgtggtggtg   1200
gccgtgtccc acgaggatcc tgaagtgaag ttcaattggt acgtggacgg cgtggaggtg   1260
cacaacgcca agaccaagcc tcgggaggaa cagtacaact ccacctaccg ggtggtgtcc   1320
gtgctgaccg tgctgcacca ggactggctg aacggcaaag agtacaagtg caaagtctcc   1380
aacaaggccc tggccgcccc tatcgaaaag acaatctcca aggccaaggg ccagcctagg   1440
gaacccagg  tgtacaccct gccacccagc cgggaggaaa tgaccaagaa ccaggtgtcc   1500
ctgacctgtc tggtcaaggg cttctaccct tccgatatcg ccgtggagtg ggagtctaac   1560
ggccagcctg agaacaacta caagaccacc cctcctgtgc tggactccga cggctccttc   1620
ttcctgtact ccaaactgac cgtggacaag tcccggtggc agcagggcaa cgtgttctcc   1680
tgctccgtga tgcacgaggc cctgcacaac cactacaccc agaagtccct gtccctgtct   1740
cccggcaag                                                           1749
```

```
<210> SEQ ID NO 50
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 50

Lys Ala Gln Leu Ser Val Gly Tyr Met His
1               5                   10

<210> SEQ ID NO 51
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 51

Asp Thr Ser Lys Leu Ala Ser
1               5

<210> SEQ ID NO 52
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 52

Phe Gln Gly Ser Gly Tyr Pro Phe Thr
1               5
```

<210> SEQ ID NO 53
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 53

Lys Ala Gln Leu Ser Val Gly Tyr Met His
1               5                   10

<210> SEQ ID NO 54
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 54

Asp Thr Ser Lys Leu Ala Ser
1               5

<210> SEQ ID NO 55
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 55

Phe Gln Gly Ser Gly Tyr Pro Phe Thr
1               5

<210> SEQ ID NO 56
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 56

Gln Leu Ser Val Gly Tyr
1               5

<210> SEQ ID NO 57
<211> LENGTH: 3
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 57

Asp Thr Ser
1

<210> SEQ ID NO 58
<211> LENGTH: 6
<212> TYPE: PRT

<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 58

Gly Ser Gly Tyr Pro Phe
1               5

<210> SEQ ID NO 59
<211> LENGTH: 106
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 59

Asp Ile Gln Met Thr Gln Ser Pro Ser Thr Leu Ser Ala Ser Val Gly
1               5                   10                  15

Asp Arg Val Thr Ile Thr Cys Lys Ala Gln Leu Ser Val Gly Tyr Met
            20                  25                  30

His Trp Tyr Gln Gln Lys Pro Gly Lys Ala Pro Lys Leu Leu Ile Tyr
        35                  40                  45

Asp Thr Ser Lys Leu Ala Ser Gly Val Pro Ser Arg Phe Ser Gly Ser
    50                  55                  60

Gly Ser Gly Thr Glu Phe Thr Leu Thr Ile Ser Ser Leu Gln Pro Asp
65                  70                  75                  80

Asp Phe Ala Thr Tyr Tyr Cys Phe Gln Gly Ser Gly Tyr Pro Phe Thr
                85                  90                  95

Phe Gly Gly Gly Thr Lys Leu Glu Ile Lys
            100                 105

<210> SEQ ID NO 60
<211> LENGTH: 318
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 60
gacatccaga tgacccagag cccctccacc ctgtccgcct ccgtgggcga cagagtgacc      60
atcacttgca aggcccagct gtccgtgggc tacatgcact ggtatcagca gaagcccggc     120
aaggccccta gctgctgat ctacgacacc tccaagctgg cctccggcgt gccctccaga      180
ttctccggct ctggctccgg caccgagttc accctgacca tctccagcct gcagcccgac     240
gacttcgcca cctactactg tttccaaggc tccggctacc ccttcaccct cggcggaggc     300
accaagctgg aaatcaag                                                   318

<210> SEQ ID NO 61
<211> LENGTH: 213
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 61

```
Asp Ile Gln Met Thr Gln Ser Pro Ser Thr Leu Ser Ala Ser Val Gly
1               5                   10                  15

Asp Arg Val Thr Ile Thr Cys Lys Ala Gln Leu Ser Val Gly Tyr Met
            20                  25                  30

His Trp Tyr Gln Gln Lys Pro Gly Lys Ala Pro Lys Leu Leu Ile Tyr
                35                  40                  45

Asp Thr Ser Lys Leu Ala Ser Gly Val Pro Ser Arg Phe Ser Gly Ser
        50                  55                  60

Gly Ser Gly Thr Glu Phe Thr Leu Thr Ile Ser Ser Leu Gln Pro Asp
65                  70                  75                  80

Asp Phe Ala Thr Tyr Tyr Cys Phe Gln Gly Ser Gly Tyr Pro Phe Thr
                85                  90                  95

Phe Gly Gly Gly Thr Lys Leu Glu Ile Lys Arg Thr Val Ala Ala Pro
                100                 105                 110

Ser Val Phe Ile Phe Pro Pro Ser Asp Glu Gln Leu Lys Ser Gly Thr
                115                 120                 125

Ala Ser Val Val Cys Leu Leu Asn Asn Phe Tyr Pro Arg Glu Ala Lys
        130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
                180                 185                 190

Cys Glu Val Thr His Gln Gly Leu Ser Ser Pro Val Thr Lys Ser Phe
                195                 200                 205

Asn Arg Gly Glu Cys
    210
```

<210> SEQ ID NO 62
<211> LENGTH: 639
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 62

```
gacatccaga tgacccagag cccctccacc ctgtccgcct ccgtgggcga cagagtgacc      60
atcacttgca aggcccagct gtccgtgggc tacatgcact ggtatcagca gaagcccggc     120
aaggccccta agctgctgat ctacgacacc tccaagctgg cctccggcgt gccctccaga     180
ttctccggct ctggctccgg caccgagttc accctgacca tctccagcct gcagcccgac     240
gacttcgcca cctactactg ttttcaaggc tccggctacc ccttcacctt cggcggaggc     300
accaagctgg aaatcaagcg tacggtggcc gctcccagcg tgttcatctt cccccccagc     360
gacgagcagc tgaagagcgg caccgccagc gtggtgtgcc tgctgaacaa cttctacccc     420
cgggaggcca aggtgcagtg gaaggtggac aacgccctgc agagcggcaa cagccaggag     480
agcgtcaccg agcaggacag caaggactcc acctacagcc tgagcagcac cctgaccctg     540
agcaaggccg actacgagaa gcataaggtg tacgcctgcg aggtgaccca ccagggcctg     600
tccagccccg tgaccaagag cttcaacagg ggcgagtgc                            639
```

<210> SEQ ID NO 63

<210> SEQ ID NO 63
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 63

Gly Phe Ser Leu Ser Thr Ser Gly Met Ser Val Gly
1               5                   10

<210> SEQ ID NO 64
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 64

Asp Ile Trp Trp Asp Asp Lys Lys Asp Tyr Asn Pro Ser Leu Lys Ser
1               5                   10                  15

<210> SEQ ID NO 65
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 65

Ser Met Ile Thr Asn Trp Tyr Phe Asp Val
1               5                   10

<210> SEQ ID NO 66
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 66

Thr Ser Gly Met Ser Val Gly
1               5

<210> SEQ ID NO 67
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 67

Asp Ile Trp Trp Asp Asp Lys Lys Asp Tyr Asn Pro Ser Leu Lys Ser
1               5                   10                  15

<210> SEQ ID NO 68
<211> LENGTH: 10
<212> TYPE: PRT
<213> ORGANISM: Artificial Sequence
<220> FEATURE:

```
<221> NAME/KEY: source
<223> OTHER INFORMATION: /note="Description of Artificial Sequence:
      Synthetic peptide"

<400> SEQUENCE: 68

Ser Met Ile Thr Asn Trp Tyr Phe Asp Val
1               5                   10

<210> SEQ ID NO 69
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 69

Gly Phe Ser Leu Ser Thr Ser Gly Met
1               5

<210> SEQ ID NO 70
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 70

Trp Trp Asp Asp Lys
1               5

<210> SEQ ID NO 71
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 71

Ser Met Ile Thr Asn Trp Tyr Phe Asp Val
1               5                   10

<210> SEQ ID NO 72
<211> LENGTH: 120
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 72

Gln Val Thr Leu Arg Glu Ser Gly Pro Ala Leu Val Lys Pro Thr Gln
1               5                   10                  15

Thr Leu Thr Leu Thr Cys Thr Phe Ser Gly Phe Ser Leu Ser Thr Ser
            20                  25                  30

Gly Met Ser Val Gly Trp Ile Arg Gln Pro Pro Gly Lys Ala Leu Glu
        35                  40                  45

Trp Leu Ala Asp Ile Trp Trp Asp Asp Lys Asp Tyr Asn Pro Ser
    50                  55                  60

Leu Lys Ser Arg Leu Thr Ile Ser Lys Asp Thr Ser Lys Asn Gln Val
```

```
                65                  70                  75                  80
Val Leu Lys Val Thr Asn Met Asp Pro Ala Asp Thr Ala Thr Tyr Tyr
                    85                  90                  95

Cys Ala Arg Ser Met Ile Thr Asn Trp Tyr Phe Asp Val Trp Gly Ala
                    100                 105                 110

Gly Thr Thr Val Thr Val Ser Ser
            115                 120
```

```
<210> SEQ ID NO 73
<211> LENGTH: 360
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 73
caagtcaccc tgcgtgaaag cggccctgcc ctggtcaagc ccacccagac cctgaccctg      60
acctgcacct tctccggctt ctccctgtcc acctccggca tgtccgtggg ctggatccgg     120
cagcctcctg gcaaggccct ggagtggctg gccgacattt ggtgggacga caagaaggac     180
tacaacccca gcctgaagtc ccggctgacc atctccaagg acacctccaa gaaccaagtg     240
gtgctgaaag tgaccaacat ggaccccgcc gacaccgcca cctactactg cgcccggtcc     300
atgatcacca actggtactt cgacgtgtgg ggcgctggca ccaccgtgac cgtgtcctct     360
```

```
<210> SEQ ID NO 74
<211> LENGTH: 450
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 74

Gln Val Thr Leu Arg Glu Ser Gly Pro Ala Leu Val Lys Pro Thr Gln
1               5                   10                  15

Thr Leu Thr Leu Thr Cys Thr Phe Ser Gly Phe Ser Leu Ser Thr Ser
                20                  25                  30

Gly Met Ser Val Gly Trp Ile Arg Gln Pro Pro Gly Lys Ala Leu Glu
            35                  40                  45

Trp Leu Ala Asp Ile Trp Trp Asp Asp Lys Lys Asp Tyr Asn Pro Ser
        50                  55                  60

Leu Lys Ser Arg Leu Thr Ile Ser Lys Asp Thr Ser Lys Asn Gln Val
65                  70                  75                  80

Val Leu Lys Val Thr Asn Met Asp Pro Ala Asp Thr Ala Thr Tyr Tyr
                    85                  90                  95

Cys Ala Arg Ser Met Ile Thr Asn Trp Tyr Phe Asp Val Trp Gly Ala
                    100                 105                 110

Gly Thr Thr Val Thr Val Ser Ser Ala Ser Thr Lys Gly Pro Ser Val
            115                 120                 125

Phe Pro Leu Ala Pro Ser Ser Lys Ser Thr Ser Gly Gly Thr Ala Ala
        130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                    165                 170                 175
```

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
            195                 200                 205

Pro Ser Asn Thr Lys Val Asp Lys Arg Val Glu Pro Lys Ser Cys Asp
            210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Ala Val Ser His Glu
            260                 265                 270

Asp Pro Glu Val Lys Phe Asn Trp Tyr Val Asp Gly Val Glu Val His
            275                 280                 285

Asn Ala Lys Thr Lys Pro Arg Glu Glu Gln Tyr Asn Ser Thr Tyr Arg
            290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Ala Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
            355                 360                 365

Thr Cys Leu Val Lys Gly Phe Tyr Pro Ser Asp Ile Ala Val Glu Trp
            370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
            435                 440                 445

Gly Lys
    450

<210> SEQ ID NO 75
<211> LENGTH: 1350
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 75
caagtcaccc tgcgtgaaag cggccctgcc ctggtcaagc ccacccagac cctgaccctg     60
acctgcacct tctccggctt ctccctgtcc acctccggca tgtccgtggg ctggatccgg    120
cagcctcctg caaggccct ggagtggctg gccgacattt ggtgggacga caagaaggac    180 tacaaccca gcctgaagtc ccggctgacc atctccaagg acacctccaa gaaccaagtg    240
gtgctgaaag tgaccaacat ggaccccgcc gacaccgcca cctactactg cgcccggtcc    300
atgatcacca actggtactt cgacgtgtgg ggcgctggca ccaccgtgac cgtgtcctct    360

-continued

```
gctagcacca agggcccctc cgtgttccct ctggccccett ccagcaagtc tacctccgge     420 ggcacagctg ctctgggctg cctggtcaag gactacttcc ctgagcctgt gacagtgtcc     480
tggaactctg gcgccctgac ctctggcgtg cacaccttcc ctgccgtgct gcagtcctcc     540
ggcctgtact ccctgtcctc cgtggtcaca gtgccttcaa gcagcctggg cacccagacc     600
tatatctgca acgtgaacca caagccttcc aacaccaagg tggacaagcg ggtggagcct     660
aagtcctgcg acaagaccca cacctgtcct ccctgccctg ctcctgaact gctgggcggc     720
ccttctgtgt tcctgttccc tccaaagccc aaggacaccc tgatgatctc ccggacccct     780
gaagtgacct gcgtggtggt ggccgtgtcc cacgaggatc ctgaagtgaa gttcaattgg     840
tacgtggacg gcgtggaggt gcacaacgcc aagaccaagc ctcgggagga acagtacaac     900
tccacctacc gggtggtgtc cgtgctgacc gtgctgcacc aggactggct gaacggcaaa     960
gagtacaagt gcaaagtctc caacaaggcc ctggccgccc tatcgaaaa gacaatctcc    1020 aaggccaagg gccagcctag ggaaccccag gtgtacaccc tgccacccag ccgggaggaa    1080
atgaccaaga accaggtgtc cctgacctgt ctggtcaagg gcttctaccc ttccgatatc    1140
gccgtggagt gggagtctaa cggccagcct gagaacaact acaagaccac ccctcctgtg    1200
ctggactccg acggctcctt cttcctgtac tccaaactga ccgtggacaa gtcccggtgg    1260
cagcagggca acgtgttctc ctgctccgtg atgcacgagg ccctgcacaa ccactacacc    1320
cagaagtccc tgtccctgtc tcccggcaag                                    1350
```

<210> SEQ ID NO 76
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 76

```
Lys Ala Gln Leu Ser Val Gly Tyr Met His
1               5                   10
```

<210> SEQ ID NO 77
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 77

```
Asp Thr Ser Lys Leu Ala Ser
1               5
```

<210> SEQ ID NO 78
<211> LENGTH: 142
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 78

```
Phe Gln Gly Ser Gly Ala Pro Thr Ser Ser Ser Thr Lys Lys Thr Gln
1               5                   10                  15
```

```
Leu Gln Leu Glu His Leu Leu Leu Asp Leu Gln Met Ile Leu Asn Gly
            20                  25                  30

Ile Asn Asn Tyr Lys Asn Pro Lys Leu Thr Arg Met Leu Thr Phe Lys
        35                  40                  45

Phe Tyr Met Pro Lys Lys Ala Thr Glu Leu Lys His Leu Gln Cys Leu
    50                  55                  60

Glu Glu Glu Leu Lys Pro Leu Glu Glu Val Leu Asn Leu Ala Gln Ser
65                  70                  75                  80

Lys Asn Phe His Leu Arg Pro Arg Asp Leu Ile Ser Asn Ile Asn Val
                85                  90                  95

Ile Val Leu Glu Leu Lys Gly Ser Glu Thr Thr Phe Met Cys Glu Tyr
            100                 105                 110

Ala Asp Glu Thr Ala Thr Ile Val Glu Phe Leu Asn Arg Trp Ile Thr
        115                 120                 125

Phe Cys Gln Ser Ile Ile Ser Thr Leu Thr Tyr Pro Phe Thr
    130                 135                 140
```

```
<210> SEQ ID NO 79
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 79

Lys Ala Gln Leu Ser Val Gly Tyr Met His
1               5                   10

<210> SEQ ID NO 80
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 80

Asp Thr Ser Lys Leu Ala Ser
1               5

<210> SEQ ID NO 81
<211> LENGTH: 142
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 81

Phe Gln Gly Ser Gly Ala Pro Thr Ser Ser Thr Lys Lys Thr Gln
1               5                   10                  15

Leu Gln Leu Glu His Leu Leu Leu Asp Leu Gln Met Ile Leu Asn Gly
            20                  25                  30

Ile Asn Asn Tyr Lys Asn Pro Lys Leu Thr Arg Met Leu Thr Phe Lys
        35                  40                  45

Phe Tyr Met Pro Lys Lys Ala Thr Glu Leu Lys His Leu Gln Cys Leu
    50                  55                  60

Glu Glu Glu Leu Lys Pro Leu Glu Glu Val Leu Asn Leu Ala Gln Ser
```

```
                65                  70                  75                  80
Lys Asn Phe His Leu Arg Pro Arg Asp Leu Ile Ser Asn Ile Asn Val
                    85                  90                  95

Ile Val Leu Glu Leu Lys Gly Ser Glu Thr Thr Phe Met Cys Glu Tyr
                100                 105                 110

Ala Asp Glu Thr Ala Thr Ile Val Glu Phe Leu Asn Arg Trp Ile Thr
                115                 120                 125

Phe Cys Gln Ser Ile Ile Ser Thr Leu Thr Tyr Pro Phe Thr
            130                 135                 140
```

<210> SEQ ID NO 82
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 82

```
Gln Leu Ser Val Gly Tyr
1               5
```

<210> SEQ ID NO 83
<211> LENGTH: 3
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 83

```
Asp Thr Ser
1
```

<210> SEQ ID NO 84
<211> LENGTH: 139
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 84

```
Gly Ser Gly Ala Pro Thr Ser Ser Ser Thr Lys Lys Thr Gln Leu Gln
1               5                   10                  15

Leu Glu His Leu Leu Leu Asp Leu Gln Met Ile Leu Asn Gly Ile Asn
                20                  25                  30

Asn Tyr Lys Asn Pro Lys Leu Thr Arg Met Leu Thr Phe Lys Phe Tyr
            35                  40                  45

Met Pro Lys Lys Ala Thr Glu Leu Lys His Leu Gln Cys Leu Glu Glu
        50                  55                  60

Glu Leu Lys Pro Leu Glu Glu Val Leu Asn Leu Ala Gln Ser Lys Asn
65                  70                  75                  80

Phe His Leu Arg Pro Arg Asp Leu Ile Ser Asn Ile Asn Val Ile Val
                85                  90                  95

Leu Glu Leu Lys Gly Ser Glu Thr Thr Phe Met Cys Glu Tyr Ala Asp
                100                 105                 110

Glu Thr Ala Thr Ile Val Glu Phe Leu Asn Arg Trp Ile Thr Phe Cys
            115                 120                 125
```

```
Gln Ser Ile Ile Ser Thr Leu Thr Tyr Pro Phe
    130                 135
```

<210> SEQ ID NO 85
<211> LENGTH: 239
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 85

```
Asp Ile Gln Met Thr Gln Ser Pro Ser Thr Leu Ser Ala Ser Val Gly
1               5                   10                  15

Asp Arg Val Thr Ile Thr Cys Lys Ala Gln Leu Ser Val Gly Tyr Met
            20                  25                  30

His Trp Tyr Gln Gln Lys Pro Gly Lys Ala Pro Lys Leu Leu Ile Tyr
        35                  40                  45

Asp Thr Ser Lys Leu Ala Ser Gly Val Pro Ser Arg Phe Ser Gly Ser
    50                  55                  60

Gly Ser Gly Thr Glu Phe Thr Leu Thr Ile Ser Ser Leu Gln Pro Asp
65                  70                  75                  80

Asp Phe Ala Thr Tyr Tyr Cys Phe Gln Gly Ser Gly Ala Pro Thr Ser
                85                  90                  95

Ser Ser Thr Lys Lys Thr Gln Leu Gln Leu Glu His Leu Leu Leu Asp
            100                 105                 110

Leu Gln Met Ile Leu Asn Gly Ile Asn Asn Tyr Lys Asn Pro Lys Leu
        115                 120                 125

Thr Arg Met Leu Thr Phe Lys Phe Tyr Met Pro Lys Lys Ala Thr Glu
    130                 135                 140

Leu Lys His Leu Gln Cys Leu Glu Glu Glu Leu Lys Pro Leu Glu Glu
145                 150                 155                 160

Val Leu Asn Leu Ala Gln Ser Lys Asn Phe His Leu Arg Pro Arg Asp
                165                 170                 175

Leu Ile Ser Asn Ile Asn Val Ile Val Leu Glu Leu Lys Gly Ser Glu
            180                 185                 190

Thr Thr Phe Met Cys Glu Tyr Ala Asp Glu Thr Ala Thr Ile Val Glu
        195                 200                 205

Phe Leu Asn Arg Trp Ile Thr Phe Cys Gln Ser Ile Ile Ser Thr Leu
    210                 215                 220

Thr Tyr Pro Phe Thr Phe Gly Gly Gly Thr Lys Leu Glu Ile Lys
225                 230                 235
```

<210> SEQ ID NO 86
<211> LENGTH: 717
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 86

```
gacatccaga tgacccagag cccctccacc ctgtccgcct ccgtgggcga cagagtgacc      60
atcacttgca aggcccagct gtccgtgggc tacatgcact ggtatcagca gaagcccggc     120
aaggccccta agctgctgat ctacgacacc tccaagctgg cctccggcgt gccctccaga     180
```

```
ttctccggct ctggctccgg caccgagttc accctgacca tctccagcct gcagcccgac    240
gacttcgcca cctactactg ttttcaaggc tctggcgccc ctacctcctc agcaccaag    300 aaaacccagc tgcagctcga acatctgctg ctggacctgc agatgatcct gaacggcatc    360
aacaactaca agaaccccaa gctgacccgg atgctgacct tcaagttcta catgcccaag    420
aaggccaccg agctgaaaca tctgcagtgc ctggaagagg aactgaagcc cctggaagaa    480
gtgctgaacc tggcccagtc caagaacttc cacctgaggc ctcgggacct gatctccaac    540
atcaacgtga tcgtgctgga actgaagggc tccgagacaa ccttcatgtg cgagtacgcc    600
gacgagacag ccaccatcgt ggaatttctg aaccggtgga tcaccttctg ccagtccatc    660
atctccaccc tgacctaccc cttcaccttc ggcggaggca ccaagctgga aatcaag     717
```

<210> SEQ ID NO 87
<211> LENGTH: 346
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 87

```
Asp Ile Gln Met Thr Gln Ser Pro Ser Thr Leu Ser Ala Ser Val Gly
1               5                   10                  15

Asp Arg Val Thr Ile Thr Cys Lys Ala Gln Leu Ser Val Gly Tyr Met
                20                  25                  30

His Trp Tyr Gln Gln Lys Pro Gly Lys Ala Pro Lys Leu Leu Ile Tyr
            35                  40                  45

Asp Thr Ser Lys Leu Ala Ser Gly Val Pro Ser Arg Phe Ser Gly Ser
        50                  55                  60

Gly Ser Gly Thr Glu Phe Thr Leu Thr Ile Ser Ser Leu Gln Pro Asp
65                  70                  75                  80

Asp Phe Ala Thr Tyr Tyr Cys Phe Gln Gly Ser Gly Ala Pro Thr Ser
                85                  90                  95

Ser Ser Thr Lys Lys Thr Gln Leu Gln Leu Glu His Leu Leu Leu Asp
            100                 105                 110

Leu Gln Met Ile Leu Asn Gly Ile Asn Asn Tyr Lys Asn Pro Lys Leu
        115                 120                 125

Thr Arg Met Leu Thr Phe Lys Phe Tyr Met Pro Lys Lys Ala Thr Glu
    130                 135                 140

Leu Lys His Leu Gln Cys Leu Glu Glu Glu Leu Lys Pro Leu Glu Glu
145                 150                 155                 160

Val Leu Asn Leu Ala Gln Ser Lys Asn Phe His Leu Arg Pro Arg Asp
                165                 170                 175

Leu Ile Ser Asn Ile Asn Val Ile Val Leu Glu Leu Lys Gly Ser Glu
            180                 185                 190

Thr Thr Phe Met Cys Glu Tyr Ala Asp Glu Thr Ala Thr Ile Val Glu
        195                 200                 205

Phe Leu Asn Arg Trp Ile Thr Phe Cys Gln Ser Ile Ile Ser Thr Leu
    210                 215                 220

Thr Tyr Pro Phe Thr Phe Gly Gly Gly Thr Lys Leu Glu Ile Lys Arg
225                 230                 235                 240

Thr Val Ala Ala Pro Ser Val Phe Ile Phe Pro Pro Ser Asp Glu Gln
                245                 250                 255

Leu Lys Ser Gly Thr Ala Ser Val Val Cys Leu Leu Asn Asn Phe Tyr
```

```
              260                 265                 270
Pro Arg Glu Ala Lys Val Gln Trp Lys Val Asp Asn Ala Leu Gln Ser
            275                 280                 285
Gly Asn Ser Gln Glu Ser Val Thr Glu Gln Asp Ser Lys Asp Ser Thr
            290                 295                 300
Tyr Ser Leu Ser Ser Thr Leu Thr Leu Ser Lys Ala Asp Tyr Glu Lys
305                 310                 315                 320
His Lys Val Tyr Ala Cys Glu Val Thr His Gln Gly Leu Ser Ser Pro
                325                 330                 335
Val Thr Lys Ser Phe Asn Arg Gly Glu Cys
                340                 345

<210> SEQ ID NO 88
<211> LENGTH: 1038
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 88
gacatccaga tgacccagag cccctccacc ctgtccgcct ccgtgggcga cagagtgacc      60
atcacttgca aggcccagct gtccgtgggc tacatgcact ggtatcagca gaagcccggc     120
aaggccccta agctgctgat ctacgacacc tccaagctgg cctccggcgt gccctccaga     180
ttctccggct ctggctccgg caccgagttc accctgacca tctccagcct gcagcccgac     240
gacttcgcca cctactactg ttttcaaggc tctggcgccc ctacctcctc cagcaccaag     300
aaaacccagc tgcagctcga acatctgctg ctggacctgc agatgatcct gaacggcatc     360
aacaactaca gaaccccaa gctgacccgg atgctgacct tcaagttcta catgcccaag     420
aaggccaccg agctgaaaca tctgcagtgc ctggaagagg aactgaagcc cctggaagaa     480
gtgctgaacc tggcccagtc caagaacttc cacctgaggc ctcgggacct gatctccaac     540
atcaacgtga tcgtgctgga actgaagggc tccagagaca ccttcatgtg cgagtacgcc     600
gacgagacag ccaccatcgt ggaatttctg aaccggtgga tcaccttctg ccagtccatc     660
atctccaccc tgacctaccc cttcaccttc ggcggaggca ccaagctgga aatcaagcgt     720
acggtggccg ctcccagcgt gttcatcttc ccccccagcg acgagcagct gaagagcggc     780
accgccagcg tggtgtgcct gctgaacaac ttctaccccc gggaggccaa ggtgcagtgg     840
aaggtggaca acgccctgca gagcggcaac agccaggaga cgtcaccga gcaggacagc     900
aaggactcca cctacagcct gagcagcacc ctgaccctga gcaaggccga ctacgagaag     960
cataaggtgt acgcctgcga ggtgacccac cagggcctgt ccagccccgt gaccaagagc    1020
ttcaacaggg gcgagtgc                                                  1038

<210> SEQ ID NO 89
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 89

Gly Phe Ser Leu Ser Thr Ser Gly Met Ser Val Gly
1               5                   10
```

```
<210> SEQ ID NO 90
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 90

Asp Ile Trp Trp Asp Asp Lys Lys Asp Tyr Asn Pro Ser Leu Lys Ser
1               5                   10                  15

<210> SEQ ID NO 91
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 91

Ser Met Ile Thr Asn Trp Tyr Phe Asp Val
1               5                   10

<210> SEQ ID NO 92
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 92

Thr Ser Gly Met Ser Val Gly
1               5

<210> SEQ ID NO 93
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 93

Asp Ile Trp Trp Asp Asp Lys Lys Asp Tyr Asn Pro Ser Leu Lys Ser
1               5                   10                  15

<210> SEQ ID NO 94
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 94

Ser Met Ile Thr Asn Trp Tyr Phe Asp Val
1               5                   10

<210> SEQ ID NO 95
<211> LENGTH: 9
```

```
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 95

Gly Phe Ser Leu Ser Thr Ser Gly Met
1               5

<210> SEQ ID NO 96
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 96

Trp Trp Asp Asp Lys
1               5

<210> SEQ ID NO 97
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 97

Ser Met Ile Thr Asn Trp Tyr Phe Asp Val
1               5                   10

<210> SEQ ID NO 98
<211> LENGTH: 120
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 98

Gln Val Thr Leu Arg Glu Ser Gly Pro Ala Leu Val Lys Pro Thr Gln
1               5                   10                  15

Thr Leu Thr Leu Thr Cys Thr Phe Ser Gly Phe Ser Leu Ser Thr Ser
            20                  25                  30

Gly Met Ser Val Gly Trp Ile Arg Gln Pro Pro Gly Lys Ala Leu Glu
        35                  40                  45

Trp Leu Ala Asp Ile Trp Trp Asp Asp Lys Lys Asp Tyr Asn Pro Ser
    50                  55                  60

Leu Lys Ser Arg Leu Thr Ile Ser Lys Asp Thr Ser Lys Asn Gln Val
65                  70                  75                  80

Val Leu Lys Val Thr Asn Met Asp Pro Ala Asp Thr Ala Thr Tyr Tyr
                85                  90                  95

Cys Ala Arg Ser Met Ile Thr Asn Trp Tyr Phe Asp Val Trp Gly Ala
            100                 105                 110

Gly Thr Thr Val Thr Val Ser Ser
        115                 120
```

<210> SEQ ID NO 99
<211> LENGTH: 360
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 99

```
caagtcaccc tgcgtgaaag cggccctgcc ctggtcaagc ccacccagac cctgaccctg      60
acctgcacct tctccggctt ctccctgtcc acctccggca tgtccgtggg ctggatccgg     120
cagcctcctg gcaaggccct ggagtggctg gccgacattt ggtgggacga caagaaggac     180
tacaacccca gcctgaagtc ccggctgacc atctccaagg acacctccaa gaaccaagtg     240
gtgctgaaag tgaccaacat ggaccccgcc gacaccgcca cctactactg cgcccggtcc     300
atgatcacca actggtactt cgacgtgtgg ggcgctggca ccaccgtgac cgtgtcctct     360
```

<210> SEQ ID NO 100
<211> LENGTH: 450
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 100

```
Gln Val Thr Leu Arg Glu Ser Gly Pro Ala Leu Val Lys Pro Thr Gln
1               5                   10                  15

Thr Leu Thr Leu Thr Cys Thr Phe Ser Gly Phe Ser Leu Ser Thr Ser
            20                  25                  30

Gly Met Ser Val Gly Trp Ile Arg Gln Pro Pro Gly Lys Ala Leu Glu
        35                  40                  45

Trp Leu Ala Asp Ile Trp Trp Asp Asp Lys Lys Asp Tyr Asn Pro Ser
    50                  55                  60

Leu Lys Ser Arg Leu Thr Ile Ser Lys Asp Thr Ser Lys Asn Gln Val
65                  70                  75                  80

Val Leu Lys Val Thr Asn Met Asp Pro Ala Asp Thr Ala Thr Tyr Tyr
                85                  90                  95

Cys Ala Arg Ser Met Ile Thr Asn Trp Tyr Phe Asp Val Trp Gly Ala
            100                 105                 110

Gly Thr Thr Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Arg Val Glu Pro Lys Ser Cys Asp
    210                 215                 220

Lys Thr His Thr Cys Pro Pro Cys Pro Ala Pro Glu Leu Leu Gly Gly
225                 230                 235                 240
```

```
Pro Ser Val Phe Leu Phe Pro Pro Lys Pro Lys Asp Thr Leu Met Ile
            245                 250                 255

Ser Arg Thr Pro Glu Val Thr Cys Val Val Ala Val Ser His Glu
        260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Ala Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450

<210> SEQ ID NO 101
<211> LENGTH: 1350
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 101
caagtcaccc tgcgtgaaag cggccctgcc ctggtcaagc ccacccagac cctgaccctg      60
acctgcacct tctccggctt ctccctgtcc acctccggca tgtccgtggg ctggatccgg     120
cagcctcctg gcaaggccct ggagtggctg gccgacattt ggtgggacga caagaaggac     180
tacaacccca gcctgaagtc ccggctgacc atctccaagg acacctccaa gaaccaagtg     240
gtgctgaaag tgaccaacat ggaccccgcc gacaccgcca cctactactg cgcccggtcc     300
atgatcacca actggtactt cgacgtgtgg ggcgctggca ccaccgtgac cgtgtcctct     360
gctagcacca agggcccctc cgtgttccct ctggcccctt ccagcaagtc tacctccggc     420
ggcacagctg ctctgggctg cctggtcaag gactacttcc ctgagcctgt gacagtgtcc     480
tggaactctg gcgccctgac ctctggcgtg cacaccttcc ctgccgtgct gcagtcctcc     540
ggcctgtact ccctgtcctc cgtggtcaca gtgccttcaa gcagcctggg cacccagacc     600
tatatctgca acgtgaacca caagccttcc aacaccaagg tggacaagcg ggtggagcct     660
aagtcctgcg acaagaccca cacctgtcct cctgccctg ctcctgaact gctgggcggc     720
```

```
ccttctgtgt tcctgttccc tccaaagccc aaggacaccc tgatgatctc ccggacccct    780
gaagtgacct gcgtggtggt ggccgtgtcc cacgaggatc ctgaagtgaa gttcaattgg    840
tacgtggacg gcgtggaggt gcacaacgcc aagaccaagc ctcgggagga acagtacaac    900
tccacctacc gggtggtgtc cgtgctgacc gtgctgcacc aggactggct gaacggcaaa    960
gagtacaagt gcaaagtctc caacaaggcc ctggccgccc tatcgaaaa gacaatctcc    1020 aaggccaagg gccagcctag ggaaccccag gtgtacaccc tgccacccag ccgggaggaa    1080
atgaccaaga accaggtgtc cctgacctgt ctggtcaagg gcttctaccc ttccgatatc    1140
gccgtggagt gggagtctaa cggccagcct gagaacaact acaagaccac ccctcctgtg    1200
ctggactccg acggctcctt cttcctgtac tccaaactga ccgtggacaa gtcccggtgg    1260
cagcagggca acgtgttctc ctgctccgtg atgcacgagg ccctgcacaa ccactacacc    1320
cagaagtccc tgtccctgtc tcccggcaag                                    1350
```

<210> SEQ ID NO 102
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 102

Lys Ala Gln Leu Ser Val Gly Tyr Met His
1               5                   10

<210> SEQ ID NO 103
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 103

Asp Thr Ser Lys Leu Ala Ser
1               5

<210> SEQ ID NO 104
<211> LENGTH: 142
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 104

Phe Gln Gly Ser Gly Ala Pro Thr Ser Ser Thr Lys Lys Thr Gln
1               5                   10                  15

Leu Gln Leu Glu His Leu Leu Leu Asp Leu Gln Met Ile Leu Asn Gly
                20                  25                  30

Ile Asn Asn Tyr Lys Asn Pro Lys Leu Thr Arg Met Leu Thr Phe Lys
            35                  40                  45

Phe Tyr Met Pro Lys Lys Ala Thr Glu Leu Lys His Leu Gln Cys Leu
        50                  55                  60

Glu Glu Glu Leu Lys Pro Leu Glu Glu Val Leu Asn Leu Ala Gln Ser
65                  70                  75                  80

```
Lys Asn Phe His Leu Arg Pro Arg Asp Leu Ile Ser Asn Ile Asn Val
                85                  90                  95

Ile Val Leu Glu Leu Lys Gly Ser Glu Thr Thr Phe Met Cys Glu Tyr
            100                 105                 110

Ala Asp Glu Thr Ala Thr Ile Val Glu Phe Leu Asn Arg Trp Ile Thr
        115                 120                 125

Phe Ser Gln Ser Ile Ile Ser Thr Leu Thr Tyr Pro Phe Thr
    130                 135                 140
```

<210> SEQ ID NO 105
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 105

```
Lys Ala Gln Leu Ser Val Gly Tyr Met His
1               5                   10
```

<210> SEQ ID NO 106
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 106

```
Asp Thr Ser Lys Leu Ala Ser
1               5
```

<210> SEQ ID NO 107
<211> LENGTH: 142
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 107

```
Phe Gln Gly Ser Gly Ala Pro Thr Ser Ser Thr Lys Lys Thr Gln
1               5                   10                  15

Leu Gln Leu Glu His Leu Leu Leu Asp Leu Gln Met Ile Leu Asn Gly
            20                  25                  30

Ile Asn Asn Tyr Lys Asn Pro Lys Leu Thr Arg Met Leu Thr Phe Lys
        35                  40                  45

Phe Tyr Met Pro Lys Lys Ala Thr Glu Leu Lys His Leu Gln Cys Leu
    50                  55                  60

Glu Glu Glu Leu Lys Pro Leu Glu Glu Val Leu Asn Leu Ala Gln Ser
65                  70                  75                  80

Lys Asn Phe His Leu Arg Pro Arg Asp Leu Ile Ser Asn Ile Asn Val
                85                  90                  95

Ile Val Leu Glu Leu Lys Gly Ser Glu Thr Thr Phe Met Cys Glu Tyr
            100                 105                 110

Ala Asp Glu Thr Ala Thr Ile Val Glu Phe Leu Asn Arg Trp Ile Thr
        115                 120                 125

Phe Ser Gln Ser Ile Ile Ser Thr Leu Thr Tyr Pro Phe Thr
```

```
                130             135             140

<210> SEQ ID NO 108
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 108

Gln Leu Ser Val Gly Tyr
1               5

<210> SEQ ID NO 109
<211> LENGTH: 3
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 109

Asp Thr Ser
1

<210> SEQ ID NO 110
<211> LENGTH: 139
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 110

Gly Ser Gly Ala Pro Thr Ser Ser Thr Lys Lys Thr Gln Leu Gln
1               5                   10                  15

Leu Glu His Leu Leu Leu Asp Leu Gln Met Ile Leu Asn Gly Ile Asn
                20                  25                  30

Asn Tyr Lys Asn Pro Lys Leu Thr Arg Met Leu Thr Phe Lys Phe Tyr
            35                  40                  45

Met Pro Lys Lys Ala Thr Glu Leu Lys His Leu Gln Cys Leu Glu Glu
    50                  55                  60

Glu Leu Lys Pro Leu Glu Glu Val Leu Asn Leu Ala Gln Ser Lys Asn
65                  70                  75                  80

Phe His Leu Arg Pro Arg Asp Leu Ile Ser Asn Ile Asn Val Ile Val
                85                  90                  95

Leu Glu Leu Lys Gly Ser Glu Thr Thr Phe Met Cys Glu Tyr Ala Asp
            100                 105                 110

Glu Thr Ala Thr Ile Val Glu Phe Leu Asn Arg Trp Ile Thr Phe Ser
        115                 120                 125

Gln Ser Ile Ile Ser Thr Leu Thr Tyr Pro Phe
    130                 135

<210> SEQ ID NO 111
<211> LENGTH: 239
<212> TYPE: PRT
<213> ORGANISM: Artificial Sequence
<220> FEATURE:
<221> NAME/KEY: source
<223> OTHER INFORMATION: /note="Description of Artificial Sequence:
```

Synthetic polypeptide"

<400> SEQUENCE: 111

Asp Ile Gln Met Thr Gln Ser Pro Ser Thr Leu Ser Ala Ser Val Gly
1               5                   10                  15

Asp Arg Val Thr Ile Thr Cys Lys Ala Gln Leu Ser Val Gly Tyr Met
            20                  25                  30

His Trp Tyr Gln Gln Lys Pro Gly Lys Ala Pro Lys Leu Leu Ile Tyr
        35                  40                  45

Asp Thr Ser Lys Leu Ala Ser Gly Val Pro Ser Arg Phe Ser Gly Ser
    50                  55                  60

Gly Ser Gly Thr Glu Phe Thr Leu Thr Ile Ser Leu Gln Pro Asp
65                  70                  75                  80

Asp Phe Ala Thr Tyr Tyr Cys Phe Gln Gly Ser Gly Ala Pro Thr Ser
                85                  90                  95

Ser Ser Thr Lys Lys Thr Gln Leu Gln Leu Glu His Leu Leu Leu Asp
            100                 105                 110

Leu Gln Met Ile Leu Asn Gly Ile Asn Asn Tyr Lys Asn Pro Lys Leu
        115                 120                 125

Thr Arg Met Leu Thr Phe Lys Phe Tyr Met Pro Lys Lys Ala Thr Glu
    130                 135                 140

Leu Lys His Leu Gln Cys Leu Glu Glu Glu Leu Lys Pro Leu Glu Glu
145                 150                 155                 160

Val Leu Asn Leu Ala Gln Ser Lys Asn Phe His Leu Arg Pro Arg Asp
                165                 170                 175

Leu Ile Ser Asn Ile Asn Val Ile Val Leu Glu Leu Lys Gly Ser Glu
            180                 185                 190

Thr Thr Phe Met Cys Glu Tyr Ala Asp Glu Thr Ala Thr Ile Val Glu
        195                 200                 205

Phe Leu Asn Arg Trp Ile Thr Phe Ser Gln Ser Ile Ile Ser Thr Leu
    210                 215                 220

Thr Tyr Pro Phe Thr Phe Gly Gly Gly Thr Lys Leu Glu Ile Lys
225                 230                 235

<210> SEQ ID NO 112
<211> LENGTH: 717
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 112
gacatccaga tgacccagag ccctccacc ctgtccgcct ccgtgggcga cagagtgacc      60
atcacttgca aggcccagct gtccgtgggc tacatgcact ggtatcagca gaagcccggc    120
aaggccccta gctgctgat ctacgacacc tccaagctgg cctccggcgt gccctccaga    180
ttctccggct ctggctccgg caccgagttc accctgacca tctccagcct gcagcccgac    240
gacttcgcca cctactactg ttttcaaggc tctggcgccc ctacctcctc cagcaccaag    300
aaaacccagc tgcagctcga acatctgctg ctggacctgc agatgatcct gaacggcatc    360
aacaactaca agaaccccaa gctgacccgg atgctgacct tcaagttcta catgcccaag    420
aaggccaccg agctgaaaca tctgcagtgc ctggaagagg aactgaagcc cctggaagaa    480
gtgctgaacc tggcccagtc caagaacttc cacctgaggc ctcgggacct gatctccaac    540

```
atcaacgtga tcgtgctgga actgaagggc tccgagacaa ccttcatgtg cgagtacgcc    600
gacgagacag ccaccatcgt ggaatttctg aaccggtgga tcaccttctc ccagtccatc    660
atctccaccc tgacctaccc cttcaccttc ggcggaggca ccaagctgga aatcaag       717
```

<210> SEQ ID NO 113
<211> LENGTH: 346
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 113

```
Asp Ile Gln Met Thr Gln Ser Pro Ser Thr Leu Ser Ala Ser Val Gly
1               5                   10                  15

Asp Arg Val Thr Ile Thr Cys Lys Ala Gln Leu Ser Val Gly Tyr Met
            20                  25                  30

His Trp Tyr Gln Gln Lys Pro Gly Lys Ala Pro Lys Leu Leu Ile Tyr
        35                  40                  45

Asp Thr Ser Lys Leu Ala Ser Gly Val Pro Ser Arg Phe Ser Gly Ser
    50                  55                  60

Gly Ser Gly Thr Glu Phe Thr Leu Thr Ile Ser Ser Leu Gln Pro Asp
65                  70                  75                  80

Asp Phe Ala Thr Tyr Tyr Cys Phe Gln Gly Ser Gly Ala Pro Thr Ser
                85                  90                  95

Ser Ser Thr Lys Lys Thr Gln Leu Gln Leu Glu His Leu Leu Leu Asp
            100                 105                 110

Leu Gln Met Ile Leu Asn Gly Ile Asn Asn Tyr Lys Asn Pro Lys Leu
        115                 120                 125

Thr Arg Met Leu Thr Phe Lys Phe Tyr Met Pro Lys Lys Ala Thr Glu
    130                 135                 140

Leu Lys His Leu Gln Cys Leu Glu Glu Glu Leu Lys Pro Leu Glu Glu
145                 150                 155                 160

Val Leu Asn Leu Ala Gln Ser Lys Asn Phe His Leu Arg Pro Arg Asp
                165                 170                 175

Leu Ile Ser Asn Ile Asn Val Ile Val Leu Glu Leu Lys Gly Ser Glu
            180                 185                 190

Thr Thr Phe Met Cys Glu Tyr Ala Asp Glu Thr Ala Thr Ile Val Glu
        195                 200                 205

Phe Leu Asn Arg Trp Ile Thr Phe Ser Gln Ser Ile Ile Ser Thr Leu
    210                 215                 220

Thr Tyr Pro Phe Thr Phe Gly Gly Gly Thr Lys Leu Glu Ile Lys Arg
225                 230                 235                 240

Thr Val Ala Ala Pro Ser Val Phe Ile Phe Pro Pro Ser Asp Glu Gln
                245                 250                 255

Leu Lys Ser Gly Thr Ala Ser Val Val Cys Leu Leu Asn Asn Phe Tyr
            260                 265                 270

Pro Arg Glu Ala Lys Val Gln Trp Lys Val Asp Asn Ala Leu Gln Ser
        275                 280                 285

Gly Asn Ser Gln Glu Ser Val Thr Glu Gln Asp Ser Lys Asp Ser Thr
    290                 295                 300

Tyr Ser Leu Ser Ser Thr Leu Thr Leu Ser Lys Ala Asp Tyr Glu Lys
305                 310                 315                 320

His Lys Val Tyr Ala Cys Glu Val Thr His Gln Gly Leu Ser Ser Pro
```

Val Thr Lys Ser Phe Asn Arg Gly Glu Cys
            340                 345

<210> SEQ ID NO 114
<211> LENGTH: 1038
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 114
gacatccaga tgacccagag cccctccacc ctgtccgcct ccgtgggcga cagagtgacc      60
atcacttgca aggcccagct gtccgtgggc tacatgcact ggtatcagca gaagcccggc     120
aaggccccta agctgctgat ctacgacacc tccaagctgg cctccggcgt gccctccaga     180
ttctccggct ctggctccgg caccgagttc accctgacca tctccagcct gcagcccgac     240
gacttcgcca cctactactg ttttcaaggc tctggcgccc tacctcctc cagcaccaag     300
aaaacccagc tgcagctcga acatctgctg ctggacctgc agatgatcct gaacggcatc     360
aacaactaca gaaccccaa gctgacccgg atgctgacct tcaagttcta catgcccaag     420
aaggccaccg agctgaaaca tctgcagtgc ctggaagagg aactgaagcc cctggaagaa     480
gtgctgaacc tggcccagtc caagaacttc acctgaggc ctcgggacct gatctccaac     540
atcaacgtga tcgtgctgga actgaaggc tccgagacaa ccttcatgtg cgagtacgcc     600
gacgagacag ccaccatcgt ggaatttctg aaccggtgga tcaccttctc ccagtccatc     660
atctccaccc tgacctaccc cttcaccttc ggcggaggca ccaagctgga aatcaagcgt     720
acggtggccg ctcccagcgt gttcatcttc ccccccagcg acgagcagct gaagagcggc     780
accgccagcg tggtgtgcct gctgaacaac ttctacccccc ggaggccaa ggtgcagtgg     840
aaggtggaca cgccctgca gagcggcaac agccaggaga gcgtcaccga gcaggacagc     900
aaggactcca cctacagcct gagcagcacc ctgaccctga caaggccga ctacgagaag     960
cataaggtgt acgcctgcga ggtgacccac cagggcctgt ccagcccgt gaccaagagc    1020
ttcaacaggg gcgagtgc                                                  1038

<210> SEQ ID NO 115
<211> LENGTH: 60
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: MISC_FEATURE
<222> LOCATION: (1)..(5)
<223> OTHER INFORMATION: /note="This region may encompass 1-5 residues"
<220> FEATURE:
<221> NAME/KEY: MISC_FEATURE
<222> LOCATION: (7)..(11)
<223> OTHER INFORMATION: /note="This region may encompass 1-5 residues"
<220> FEATURE:
<221> NAME/KEY: MISC_FEATURE
<222> LOCATION: (13)..(17)
<223> OTHER INFORMATION: /note="This region may encompass 1-5 residues"
<220> FEATURE:
<221> NAME/KEY: MISC_FEATURE
<222> LOCATION: (19)..(23)
<223> OTHER INFORMATION: /note="This region may encompass 1-5 residues"
<220> FEATURE:

```
<221> NAME/KEY: MISC_FEATURE
<222> LOCATION: (25)..(29)
<223> OTHER INFORMATION: /note="This region may encompass 1-5 residues"
<220> FEATURE:
<221> NAME/KEY: MISC_FEATURE
<222> LOCATION: (31)..(35)
<223> OTHER INFORMATION: /note="This region may encompass 1-5 residues"
<220> FEATURE:
<221> NAME/KEY: MISC_FEATURE
<222> LOCATION: (37)..(41)
<223> OTHER INFORMATION: /note="This region may encompass 1-5 residues"
<220> FEATURE:
<221> NAME/KEY: MISC_FEATURE
<222> LOCATION: (43)..(47)
<223> OTHER INFORMATION: /note="This region may encompass 1-5 residues"
<220> FEATURE:
<221> NAME/KEY: MISC_FEATURE
<222> LOCATION: (49)..(53)
<223> OTHER INFORMATION: /note="This region may encompass 1-5 residues"
<220> FEATURE:
<221> NAME/KEY: MISC_FEATURE
<222> LOCATION: (55)..(59)
<223> OTHER INFORMATION: /note="This region may encompass 1-5 residues"
<220> FEATURE:
<221> NAME/KEY: MISC_FEATURE
<222> LOCATION: (1)..(60)
<223> OTHER INFORMATION: /note="This sequence may encompass 0-10 '(Gly)
      n-Ser' repeating units where n=1-5"

<400> SEQUENCE: 115

Gly Gly Gly Gly Gly Ser Gly Gly Gly Gly Ser Gly Gly Gly Gly
1               5                   10                  15

Gly Ser Gly Gly Gly Gly Gly Ser Gly Gly Gly Gly Gly Ser Gly Gly
                20                  25                  30

Gly Gly Gly Ser Gly Gly Gly Gly Ser Gly Gly Gly Gly Gly Ser
            35                  40                  45

Gly Gly Gly Gly Gly Ser Gly Gly Gly Gly Gly Ser
    50                  55                  60

<210> SEQ ID NO 116
<211> LENGTH: 60
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: MISC_FEATURE
<222> LOCATION: (1)..(5)
<223> OTHER INFORMATION: /note="This region may encompass 1-5 residues"
<220> FEATURE:
<221> NAME/KEY: MISC_FEATURE
<222> LOCATION: (7)..(11)
<223> OTHER INFORMATION: /note="This region may encompass 1-5 residues"
<220> FEATURE:
<221> NAME/KEY: MISC_FEATURE
<222> LOCATION: (13)..(17)
<223> OTHER INFORMATION: /note="This region may encompass 1-5 residues"
<220> FEATURE:
<221> NAME/KEY: MISC_FEATURE
<222> LOCATION: (19)..(23)
<223> OTHER INFORMATION: /note="This region may encompass 1-5 residues"
<220> FEATURE:
<221> NAME/KEY: MISC_FEATURE
<222> LOCATION: (25)..(29)
<223> OTHER INFORMATION: /note="This region may encompass 1-5 residues"
<220> FEATURE:
<221> NAME/KEY: MISC_FEATURE
<222> LOCATION: (31)..(35)
<223> OTHER INFORMATION: /note="This region may encompass 1-5 residues"
<220> FEATURE:
<221> NAME/KEY: MISC_FEATURE
<222> LOCATION: (37)..(41)
```

```
<223> OTHER INFORMATION: /note="This region may encompass 1-5 residues"
<220> FEATURE:
<221> NAME/KEY: MISC_FEATURE
<222> LOCATION: (43)..(47)
<223> OTHER INFORMATION: /note="This region may encompass 1-5 residues"
<220> FEATURE:
<221> NAME/KEY: MISC_FEATURE
<222> LOCATION: (49)..(53)
<223> OTHER INFORMATION: /note="This region may encompass 1-5 residues"
<220> FEATURE:
<221> NAME/KEY: MISC_FEATURE
<222> LOCATION: (55)..(59)
<223> OTHER INFORMATION: /note="This region may encompass 1-5 residues"
<220> FEATURE:
<221> NAME/KEY: MISC_FEATURE
<222> LOCATION: (1)..(60)
<223> OTHER INFORMATION: /note="This sequence may encompass 0-10 '(Gly)
     n-Ala' repeating units where n=1-5"

<400> SEQUENCE: 116

Gly Gly Gly Gly Gly Ala Gly Gly Gly Gly Ala Gly Gly Gly Gly
1               5                   10                  15

Gly Ala Gly Gly Gly Gly Gly Ala Gly Gly Gly Gly Ala Gly Gly
            20                  25                  30

Gly Gly Gly Ala Gly Gly Gly Gly Ala Gly Gly Gly Gly Ala
        35                  40                  45

Gly Gly Gly Gly Gly Ala Gly Gly Gly Gly Ala
    50                  55                  60

<210> SEQ ID NO 117
<211> LENGTH: 110
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: MISC_FEATURE
<222> LOCATION: (1)..(10)
<223> OTHER INFORMATION: /note="This region may encompass 0-10 residues"
<220> FEATURE:
<221> NAME/KEY: MISC_FEATURE
<222> LOCATION: (12)..(21)
<223> OTHER INFORMATION: /note="This region may encompass 0-10 residues"
<220> FEATURE:
<221> NAME/KEY: MISC_FEATURE
<222> LOCATION: (23)..(32)
<223> OTHER INFORMATION: /note="This region may encompass 0-10 residues"
<220> FEATURE:
<221> NAME/KEY: MISC_FEATURE
<222> LOCATION: (34)..(43)
<223> OTHER INFORMATION: /note="This region may encompass 0-10 residues"
<220> FEATURE:
<221> NAME/KEY: MISC_FEATURE
<222> LOCATION: (45)..(54)
<223> OTHER INFORMATION: /note="This region may encompass 0-10 residues"
<220> FEATURE:
<221> NAME/KEY: MISC_FEATURE
<222> LOCATION: (56)..(65)
<223> OTHER INFORMATION: /note="This region may encompass 0-10 residues"
<220> FEATURE:
<221> NAME/KEY: MISC_FEATURE
<222> LOCATION: (67)..(76)
<223> OTHER INFORMATION: /note="This region may encompass 0-10 residues"
<220> FEATURE:
<221> NAME/KEY: MISC_FEATURE
<222> LOCATION: (78)..(87)
<223> OTHER INFORMATION: /note="This region may encompass 0-10 residues"
<220> FEATURE:
<221> NAME/KEY: MISC_FEATURE
<222> LOCATION: (89)..(98)
<223> OTHER INFORMATION: /note="This region may encompass 0-10 residues"
<220> FEATURE:
```

-continued

<221> NAME/KEY: MISC_FEATURE
<222> LOCATION: (100)..(109)
<223> OTHER INFORMATION: /note="This region may encompass 0-10 residues"
<220> FEATURE:
<221> NAME/KEY: MISC_FEATURE
<222> LOCATION: (1)..(110)
<223> OTHER INFORMATION: /note="This sequence may encompass 1-10 '(Gly)n-Ser' repeating units where n=0-10"

<400> SEQUENCE: 117

Gly Gly Gly Gly Gly Gly Gly Gly Gly Ser Gly Gly Gly Gly Gly
1               5                   10                  15

Gly Gly Gly Gly Gly Ser Gly Gly Gly Gly Gly Gly Gly Gly Gly
                20                  25                  30

Ser Gly Gly Gly Gly Gly Gly Gly Gly Ser Gly Gly Gly Gly Gly
        35                  40                  45

Gly Gly Gly Gly Gly Gly Ser Gly Gly Gly Gly Gly Gly Gly Gly
    50                  55                  60

Gly Ser Gly Gly Gly Gly Gly Gly Gly Gly Ser Gly Gly Gly Gly
65                  70                  75                  80

Gly Gly Gly Gly Gly Gly Ser Gly Gly Gly Gly Gly Gly Gly Gly
            85                  90                  95

Gly Gly Ser Gly Gly Gly Gly Gly Gly Gly Gly Ser
        100                 105                 110

<210> SEQ ID NO 118
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"
<220> FEATURE:
<221> NAME/KEY: source
<223> OTHER INFORMATION: /note="See specification as filed for detailed description of substitutions and preferred embodiments"

<400> SEQUENCE: 118

Gly Gly Gly Gly Ser
1               5

<210> SEQ ID NO 119
<211> LENGTH: 110
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"
<220> FEATURE:
<221> NAME/KEY: MISC_FEATURE
<222> LOCATION: (1)..(10)
<223> OTHER INFORMATION: /note="This region may encompass 0-10 residues"
<220> FEATURE:
<221> NAME/KEY: MISC_FEATURE
<222> LOCATION: (12)..(21)
<223> OTHER INFORMATION: /note="This region may encompass 0-10 residues"
<220> FEATURE:
<221> NAME/KEY: MISC_FEATURE
<222> LOCATION: (23)..(32)
<223> OTHER INFORMATION: /note="This region may encompass 0-10 residues"
<220> FEATURE:
<221> NAME/KEY: MISC_FEATURE
<222> LOCATION: (34)..(43)
<223> OTHER INFORMATION: /note="This region may encompass 0-10 residues"
<220> FEATURE:
<221> NAME/KEY: MISC_FEATURE
<222> LOCATION: (45)..(54)

```
<223> OTHER INFORMATION: /note="This region may encompass 0-10 residues"
<220> FEATURE:
<221> NAME/KEY: MISC_FEATURE
<222> LOCATION: (56)..(65)
<223> OTHER INFORMATION: /note="This region may encompass 0-10 residues"
<220> FEATURE:
<221> NAME/KEY: MISC_FEATURE
<222> LOCATION: (67)..(76)
<223> OTHER INFORMATION: /note="This region may encompass 0-10 residues"
<220> FEATURE:
<221> NAME/KEY: MISC_FEATURE
<222> LOCATION: (78)..(87)
<223> OTHER INFORMATION: /note="This region may encompass 0-10 residues"
<220> FEATURE:
<221> NAME/KEY: MISC_FEATURE
<222> LOCATION: (89)..(98)
<223> OTHER INFORMATION: /note="This region may encompass 0-10 residues"
<220> FEATURE:
<221> NAME/KEY: MISC_FEATURE
<222> LOCATION: (100)..(109)
<223> OTHER INFORMATION: /note="This region may encompass 0-10 residues"
<220> FEATURE:
<221> NAME/KEY: MISC_FEATURE
<222> LOCATION: (1)..(110)
<223> OTHER INFORMATION: /note="This sequence may encompass 1-10 '(Gly)
     n-Ala' repeating units where n=0-10"

<400> SEQUENCE: 119

Gly Gly Gly Gly Gly Gly Gly Gly Gly Ala Gly Gly Gly Gly Gly
1               5                   10                  15

Gly Gly Gly Gly Gly Ala Gly Gly Gly Gly Gly Gly Gly Gly Gly
                20                  25                  30

Ala Gly Gly Gly Gly Gly Gly Gly Gly Ala Gly Gly Gly Gly Gly
            35                  40                  45

Gly Gly Gly Gly Gly Ala Gly Gly Gly Gly Gly Gly Gly Gly Gly
        50                  55                  60

Gly Ala Gly Gly Gly Gly Gly Gly Gly Gly Ala Gly Gly Gly Gly
65                  70                  75                  80

Gly Gly Gly Gly Gly Gly Gly Ala Gly Gly Gly Gly Gly Gly Gly
                85                  90                  95

Gly Gly Ala Gly Gly Gly Gly Gly Gly Gly Gly Gly Ala
            100                 105                 110

<210> SEQ ID NO 120
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
     Synthetic peptide"
<220> FEATURE:
<221> NAME/KEY: source
<223> OTHER INFORMATION: /note="See specification as filed for detailed
     description of substitutions and preferred embodiments"

<400> SEQUENCE: 120

Gly Gly Gly Gly Ala
1               5

<210> SEQ ID NO 121
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
     Synthetic 6xHis tag"
```

```
<400> SEQUENCE: 121

His His His His His His
1               5
```